US008691502B2

(12) United States Patent
Kupper et al.

(10) Patent No.: US 8,691,502 B2
(45) Date of Patent: Apr. 8, 2014

(54) T-CELL VACCINATION WITH VIRAL VECTORS VIA MECHANICAL EPIDERMAL DISRUPTION

(75) Inventors: Thomas S. Kupper, Weston, MA (US); Luzheng Liu, Vernon Hills, IL (US); Rachael A. Clark, Belmont, MA (US)

(73) Assignee: TremRx, Inc., Boston, MA (US)

( * ) Notice: Subject to any disclaimer, the term of this patent is extended or adjusted under 35 U.S.C. 154(b) by 0 days.

(21) Appl. No.: 13/099,235

(22) Filed: May 2, 2011

(65) Prior Publication Data

US 2011/0274649 A1  Nov. 10, 2011

Related U.S. Application Data

(63) Continuation-in-part of application No. PCT/US2008/012345, filed on Oct. 31, 2008.

(51) Int. Cl.
 C12Q 1/70 (2006.01)
 A61K 39/275 (2006.01)
 A61K 39/285 (2006.01)
 C12N 15/00 (2006.01)

(52) U.S. Cl.
 USPC ........ 435/5; 435/320.1; 424/232.1; 424/184.1

(58) Field of Classification Search
 USPC .......................................................... 424/93
 See application file for complete search history.

(56) References Cited

U.S. PATENT DOCUMENTS

| | | | |
|---|---|---|---|
| 2,378,237 A | 6/1945 | Morris | |
| 3,604,249 A | 9/1971 | Wilson | |
| 3,815,407 A | 6/1974 | Lavery | |
| 3,871,407 A | 3/1975 | Bykov | |
| 4,603,112 A | 7/1986 | Paoletti | |
| 5,185,146 A | 2/1993 | Altenburger | |
| 5,487,726 A * | 1/1996 | Rabenau et al. | 604/46 |
| 5,641,972 A | 6/1997 | Breda | |
| 5,942,235 A | 8/1999 | Paoletti | |
| 6,045,802 A * | 4/2000 | Schlom et al. | 424/199.1 |
| 6,381,547 B1 | 4/2002 | Heirtzler | |
| 6,440,422 B1 | 8/2002 | Sutter | |
| 6,924,137 B2 | 8/2005 | Howley | |
| 7,097,842 B2 | 8/2006 | Suter | |
| 7,118,738 B2 | 10/2006 | Schlom | |
| 7,378,101 B2 | 5/2008 | Hardham et al. | |
| 2003/0013190 A1 | 1/2003 | Mayr | |
| 2003/0108555 A1* | 6/2003 | Marinkovich | 424/178.1 |
| 2003/0138454 A1 | 7/2003 | Hill | |
| 2004/0064087 A1 | 4/2004 | Lastovich | |
| 2004/0131594 A1 | 7/2004 | McMichael | |
| 2005/0106123 A1 | 5/2005 | Emini | |
| 2005/0171047 A1 | 8/2005 | Krieg | |
| 2005/0214323 A1 | 9/2005 | Chaplin | |
| 2005/0255121 A1 | 11/2005 | Campbell | |
| 2006/0159706 A1 | 7/2006 | Panicali | |
| 2007/0088248 A1 | 4/2007 | Glenn | |
| 2008/0009785 A1 | 1/2008 | Mikszta | |

FOREIGN PATENT DOCUMENTS

| | | |
|---|---|---|
| EP | 0180490 | 5/1986 |
| EP | 0308220 | 3/1989 |
| GB | 2034323 | 6/1980 |
| GB | 2322130 | 8/1998 |
| WO | 8903429 | 4/1989 |
| WO | 9703203 | 1/1997 |
| WO | 0034494 | 6/2000 |
| WO | 0195919 | 12/2001 |
| WO | WO2005103303 A2 * | 11/2003 |
| WO | 2004058278 | 7/2004 |
| WO | 2005103303 | 11/2005 |
| WO | 2006072787 | 7/2006 |

OTHER PUBLICATIONS

Kantor et al., Immunogenecity and Safety of a Recombinant Vaccinia Virus Vaccine Expressing the Carcinoembryonic Antigen Gene in a Nonhuman Primate, 1992, Cancer Research, 52:6917-6925.*
Athale, et al, "Skin scarification with modified vaccinia Ankara virus provides superior and safer protective immunization strategy against poxvirus challenge", J Inv. Derma., 128 (1):S192 (2008).
Bansal-Pakal, et al. "Signaling through OX40 (CD134) breaks peripheral T-cell cell tolerance", Nature Med., 7: 907-12 (2001).
Bernhard, et al., "Monoclonal Antibody-Mediated Tumor Regression by Induction of Apoptosis", Science, 245:301-304 (1989).
Bhattacharya-Chatterjee, et al., "Idiotype vaccines against human T cell leukemia. II. Generation and characterization of a monoclonal idiotype cascade (Ab1, Ab2, and Ab3)", J. Immuno, 141:1398-1403 (1988).
Binns, et al., "Comparison of a conserved region in fowlpox virus and vaccinia virus genomes and the translocation of the fowlpox virus thymidine kinase gene", J. Gen. Virol. 69:1275 (1988).
Boon, et al., "Tumor antigens recognized by T lymphocytes", Annu. Rev. Immunol., 12:337-365 (1994).

(Continued)

*Primary Examiner* — Stacy B. Chen
(74) *Attorney, Agent, or Firm* — Pabst Patent Group LLP

(57) ABSTRACT

Attenuated, replication-deficient viruses such as vaccinia viruses are used to deliver an exogenous viral, bacterial, parasitic or tumor antigen to an epidermal tissue such as the skin, lungs or gastrointestinal tract, which has been mechanically disrupted, in an amount effective to elicit or stimulate a cell mediated immune response. The epidermal tissue may be mechanically disrupted by a device such as a scarification needle or an abrader device. The epidermis may be mechanically disrupted prior to, at the same time, or immediately after the administration of the vaccine. The vaccine can be used to induce immunity against a pathogen, such as a virus, bacteria, or parasite, or against a cancer in a subject that has or is at risk of developing cancer. In some embodiments a co-stimulatory molecule, a growth factor, an adjuvant and/or a cytokine is administered before, with or after the viral vaccine. In some embodiments, the co-stimulatory molecule is co-expressed with the antigen by the virus.

14 Claims, 20 Drawing Sheets

(56) References Cited

OTHER PUBLICATIONS

Boursnell, et al., "Insertion of the fusion gene from Newcastle disease virus into a non-essential region in the terminal repeats of fowlpox virus and demonstration of protective immunity induced by the recombinant", J. of Gen. Virol., 71:621-628 (1990).

Boyle, et al., "Fowlpox virus thymidine kinase: nucleotide sequence and relationships to other thymidine kinases", Virology, 156:355 (1987).

Brichard, et al., "The tyrosinase gene codes for an antigen recognized by autologous cytolytic T lymphocytes on HLA-A2 melanomas", J. Exp. Med. 178:489-95 (1993).

Bronte, et al., "Antigen expressions by dendritic cells correlates with the therapeutic effectiveness of a model recombinant poxvirus tumor vaccine", PNAS, 94:3183-8 (1997).

Brown, et al., "lac repressor can regulate expression from a hybrid SV40 early promoter containing a lac operator in animal cells", Cell, 49:603-612 (1987).

Bumol, et al., "Characterization of the human tumor and normal tissue reactivity of the KS1/4 monoclonal antibody", Hybridoma, 7(4):407-15 (1988).

Calvert, et al., "Fowlpox virus recombinants expressing the envelope glycoprotein of an avian reticuloendotheliosis retrovirus induce neutralizing antibodies and reduce viremia in chickens", J. of Virol. 67:3069-3076 (1993).

Cepko, et al., "Construction and applications of a highly transmissible murine retrovirus shuttle vector", Cell, 37:1053-62 (1984).

Connor, et al., "A key role for lung-resident memory lymphocytes in protective immune responses after BCG vaccination", Eur J Immunol., 40(9):2482-92 (2010).

Cooney, et al., "Safety of and immunological response to a recombinant vaccinia virus vaccine expressing HIV envelope glycoprotein", Lancet, 337:567-72 (1991).

Cox, et al., "Identification of a peptide recognized by five melanoma-specific human cytotoxic T cell lines", Science, 264:716-719 (1994).

Edelson, "Cutaneous T-cell lymphoma: a model for selective immunotherapy", Cancer J. Sci. Am., 4:62-71 (1998).

Emini, et al., "Priming for and induction of anti-poliovirus neutralizing antibodies by synthetic peptides", Nature, 304:699-703 (1983).

Esposito and Knight, "Nucleotide sequence of the thymidine kinase gene region of monkeypox and variola viruses", Virology, 135:561-67 (1984).

Estin, et al., "Transfected mouse melanoma lines that express various levels of human melanoma-associated antigen p97", J. Natl. Cancer Instit., 81(6):445-446 (1989).

Feizi, "Demonstration by monoclonal antibodies that carbohydrate structures of glycoproteins and glycolipids are onco-developmental antigens", Nature, 314:53-57 (1985).

Foon, et al., "Murine antiidiotype monoclonal antibody induces specific humoral responses to carcinoembryonic antigen (CEA) in colorectal cancer patients", Proc. Am. Soc. Clin. Oncol. 13:294 (1994).

Fox, et al., "In vitro and in vivo antitumor properties of a T-cell clone generated from murine tumor-infiltrating lymphocytes", J. Biol. Response Mod., 9:499-511 (1990).

Ganem and Varmus, "The molecular biology of the hepatitis B viruses", Ann. Rev. Biochem. 56:651-693 (1987).

Gershon, et al., "The nucleotide sequence around the capripoxvirus thymidine kinase gene reveals a gene shared specifically with leporipoxvirus", J. Gen. Virol., 70:525-33 (1989).

Ghetie, et al., "Anti-CD19 inhibits the growth of human B-cell tumor lines in vitro and of Daudi cells in SCID mice by inducing cell cycle arrest", Blood, 83:1329-36 (1994).

Gonzales-Scarano, et al., << Characterization of monoclonal antibodies against the G1 and N proteins of LaCrosse and Tahyna, two California serogroup bunyaviruses, Virology, 120:42-53 (1982).

Hellstrom, et al., "Monoclonal antibodies to cell surface antigens shared by chemically induced mouse bladder carcinomas", Cancer. Res., 45:2210-18 (1985).

Hellstrom, et al., "Monoclonal mouse antibodies raised against human lung carcinoma", Cancer Res., 46:3917-23 (1986).

Hellstrom, et al., "Cellular immunity against tumor antigens", Adv. Cancer Res., 12:167-223 (1969).

Henttu and Vihko, "cDNA coding for the entire human prostate specific antigen shows high homologies to the human tissue kallikrein genes", Biochem. Biophys. Res. Comm., 160(2):903-910 (1989).

Herlyn, et al., "Monoclonal antibody detection of a circulating tumor-associated antigen. I. Presence of antigen in sera of patients with colorectal, gastric, and pancreatic carcinoma", J. Clin. Immunol. 2:135-40 (1982).

Hilkens, et al., "Cell membrane-associated mucins and their adhesion-modulating modulating property", Trends in Bio. Chem. Sci., 17:359-63 (1992).

HIV Vaccines from Bangkok—2, big news day: HIV vaccine conference, Tuesday Sep. 13, 2011.

Hoon, et al., "Molecular cloning of a human monoclonal antibody reactive to ganglioside GM3 antigen on human cancers", Cancer Res., 53:5244-50 (1993).

Hooper, et al., "Smallpox DNA vaccine delivered by novel skin electroporation device protects mice against intranasal poxvirus challenge", Vaccine, 25:1814-23 (2007).

Hörig and Kaufman, "Local delivery of poxvirus vaccines for melanoma", Semin Cancer Biol., 13(6):417-22 (2003) Abstract only.

Houghton, "Cancer Antigens: Immune Recognition of Self and Altered Self", J. Exp. Med., 180:1-4 (1994).

Hruby, et al., "Fine structure analysis and nucleotide sequence of the vaccinia virus thymidine kinase gene", PNAS, 80:3411-15 (1983).

Hu, et al., "Yaba-like disease virus: an alternative replicating poxvirus vector for cancer gene therapy", J Virol., 75(21):10300-8 (2011).

Israeli, et al., "Molecular cloning of a complementary DNA encoding a prostate-specific membrane antigen", Cancer Res., 53:227-230 (1993).

Itoh, et al., "Synthesis in yeast of hepatitis B virus surface antigen modified P31 particles by gene modification", Biochem Biophys Res Commun. 141(3):942-8 (1986).

Jenkins, et al., "Formation of lentivirus particles by mammalian cells infected with recombinant fowlpox virus", AIDS Res. Human-Retroviruses, 7:991-998 (1991).

Kantor, et al., "Immunogenicity and safety of a recombinant vaccinia virus vaccine expressing the carcinoembryonic antigen gene in a nonhuman primate", Cancer Res., 52:6917-25 (1992A).

Kantor, et al., "Antitumor activity and immune responses induced by a recombinant carcinoembryonic antigen-vaccinia virus vaccine", J. Natl. Cancer Inst. 84:1084-91(1992B).

Kawakami, et al., "Cloning of the gene coding for a shared human melanoma antigen recognized by autologous T cells infiltrating into tumor", PNAS, 91:3515-19 (1994A).

Kawakami, et al., "Identification of the immunodominant peptides of the MART-1 human melanoma antigen recognized by the majority of HLA-A2-restricted tumor infiltrating lymphocytes", J. Exp. Med., 180:347-52 (1994B).

Kawakami, et al., "Identification of a human melanoma antigen recognized by tumor-infiltrating lymphocytes associated with in vivo tumor rejection", PNAS, 91:6458-62 (1994C).

Kieny, et al., "Expression of rabies virus glycoprotein from a recombinant vaccinia virus", Nature, 312:163-6 (1984).

Kilpatrick, et al., "Cloning and physical mapping of Yaba monkey tumor virus DNA", Virology, 143:399 (1985).

Liu, et al., "Dendritic cells are preferentially targeted among hematolymphocytes by modified vaccine virus Ankara and play a key role in the induction of virus-specific T cell responses in vivo", BMC Immunol., 9:15 (2008).

Liu et al, "Dynamic programming of CD8+ T cell trafficking after live viral immunization", Immunity, 25(3):511-20 (2006).

Liu, et al., "Vaccinia virus induces strong immunoregulatory cytokine production in healthy human epidermal keratinocytes: a novel strategy for immune evasion", J.Virol., 79 (12):7363-70 (2005).

Liu, et al., "Epidermal injury and infection during poxvirus immunization is crucial for the generation of highly protective T cell-mediated immunity", Nature Med.,;16(2):224-7 (2010).

(56) References Cited

OTHER PUBLICATIONS

Livingston, et al., "Improved survival in stage III melanoma patients with GM2 antibodies: a randomized trial of adjuvant vaccination with GM2 ganglioside", J. Clin. Oncol. 12:1036-44 (1994).
Lowe, et al., "Varicella-zoster virus as a live vector for the expression of foreign genes", PNAS, 84:3896-3900 (1987).
Lytvyn, et al., "Comparison of the thymidine kinase genes from three entomopoxviruses", J. Gen. Virol. 73:3235-40 (1992).
Mackett, et al., "Vaccinia virus: a selectable eukaryotic cloning and expression vector", PNAS, 79:7415-19 (1982).
Masopust, et al., "Dynamic T cell migration program provides resident memory within intestinal epithelium", J Exp Med., 207(3):553-64 (2010).
Mathews and Roehrig, "Determination of the protective epitopes on the glycoproteins of Venezuelan equine encephalomyelitis virus by passive transfer of monoclonal antibodies", J. Immunol., 129:2763-67 (1982).
Mayr, et al., "The smallpox vaccination strain MVA: marker, genetic structure, experience gained with the parenteral vaccination and behavior in organisms with a debilitated defence mechanism", Zbl. Bakt. Hyg. I, Abt. Org. B 167, 375-390 (1978) Article in German with English abstract.
Mayr and Danner, "Vaccination against pox diseases under immunosuppressive conditions", Dev. Biol. Stand., 41:225-34 (1978).
Mayr, et al., "Passage history, properties and applicability of the attenuated vaccine virus strainM AV", Infection, 3:6-14 (1975). Article in German with English abstract.
Meyer, et al., "Mapping of deletions in the genome of the highly attenuated vaccinia virus MVA and their influence on virulence", J. Gen. Virol. 72, 1031-38 (1991).
Mittleman, et al., "Active specific Immunotherapy in patients with melanoma. A clinical trial with mouse antiidiotypic monoclonal antibodies elicited with syngeneic anti-high-molecular-weight-melanoma-associated antigen monoclonal antibodies", J. Clin. Invest., 86:2136-44 (1990).
Morin, et al., "Recombinant adenovirus induces antibody response to hepatitis B virus surface antigen in hamsters", PNAS, 84:4626-30 (1987).
Muraro, et al., "Definition by monoclonal antibodies of a repertoire of epitopes on carcinoembryonic antigen differentially expressed in human colon carcinomas versus normal adult tissues", Cancer Res., 45:5769-80 (1985).
Natali, et al.,"Immunohistochemical detection of antigen in human primary and metastatic melanomas by the monoclonal antibody 140. 240 and its possible prognostic significance", Cancer, 59:55-63 (1987).
Neurath, et al., "Antibodies to a synthetic peptide from the preS 120-145 region of the hepatitis B virus envelope are virus neutralizing", Vaccine, 4:35-7 (1986).
Newton, et al., "Sequence of the hemagglutinin gene of influenza virus A/Memphis/1/71 and previously uncharacterized monoclonal antibody-derived variants", Virology, 128:495-501 (1993).
Panicali and Paoletti, "Construction of poxviruses as cloning vectors: insertion of the thymidine kinase gene from herpes simplex virus into the DNA of infectious vaccinia virus", PNAS, 79:4927-31(1982).
Panicali, et al., "Vaccinia virus vectors utilizing the beta-galactosidase assay for rapid selection of recombinant viruses and measurement of gene expression", Gene, 47:193-9 (1986).
Pardoll, "Tumour antigens. A new look for the 1990s", Nature, 369:357-8 (1994).
Perez and Walker, "Isolation and characterization of a cDNA encoding the KS1/4 epithelial carcinoma marker", J. Immunol., 142:3662-67 (1990).
Perreau, et al., "DNA/NYVAC vaccine regimen induces HIV-specific CD4 and CD8 T-cell responses in intestinal mucosa", J Virol., 85(19):9854-62 (2011).
Putney, et al., "HTLV-III/LAV-neutralizing antibodies to an *E. coli*-produced fragment of the virus envelope", Science, 234:1392-5 (1986).
Ragnhammar, et al., "Effect of monoclonal antibody 17-1A and GM-CSF in patients with advanced colorectal carcinoma—long-lasting, complete remissions can be induced", Int. J. Cancer, 53:751-8 (1993).
Reff, et al., "Depletion of B cells in vivo by a chimeric mouse human monoclonal antibody to CD20", Blood, 83:435-45 (1994).
Riffault, et al., "Transient IFN-gamma synthesis in the lymph node draining a dermal site loaded with UV-irradiated herpes simplex virus 1; an NK- and CD3-dependent process regulated by IL-12 but not by IFN-alpha/beta", J Gen. Virol., 81:2365-73 (2000).
Robbins, et al., "Transduction and expression of the human carcinoembryonic antigen gene in a murine colon carcinoma cell line", Cancer Res., 51:3657-62 (1991).
Saleh, et al., "Generation of a human anti-idiotypic antibody that mimics the GD2 antigen", J. Immunol., 151:3390-98 (1993).
Scheiflinger, et al., "Construction of chimeric vaccinia viruses by molecular cloning and packaging", PNAS, 89:9977-81(1992).
Schnitzlein, et al., "A rapid method for identifying the thymidine kinase genes of avipoxviruses", J. Virological Methods, 20:341-52 (1988).
Sgouros, et al., "Modeling and dosimetry of monoclonal antibody M195 (anti-CD33) in acute myelogenous leukemia", J. Nucl. Med., 34:422-30 (1993).
Shitara, et al., "A mouse/human chimeric anti-(ganglioside GD3) antibody with enhanced antitumor activities", Cancer Immunol. Immunother. 36:373-80 (1993).
Smith, et al., "Infectious vaccinia virus recombinants that express hepatitis B virus surface antigen", Nature, 302:490-5 (1983).
Smith, et al., "Construction and characterization of an Infectious vaccinia virus recombinant that expresses the influenza hemagglutinin gene and induces resistance to influenza virus infection in hamsters", PNAS, 80;7155-9 (1983).
Spehner, et al., "Construction of fowlpox virus vectors with intergenic insertions: expression of the beta-galactosidase gene and the measles virus fusion gene", J.Virol., 64:527-33 (1990).
Stickl, et al., "[MVA vaccination against smallpox: clinical tests with an attenuated live vaccinia virus strain (MVA) (author's transl)]", Dtsch. med. Wschr. 99:2386-92 (1974).Article in German with English abstract.
Sutter, et al., "A recombinant vector derived from the host range-restricted and highly attenuated MVA strain of vaccinia virus stimulates protective immunity in mice to influenza virus", Vaccine, 12(11):1032-40 (1994).
Tailor, et al., "Nucleotide sequence of human prostatic acid phosphatase determined from a full-length cDNA clone", Nucl. Acids Res., 18(16):4928 (1990).
Taylor, et al., "Recombinant fowlpox virus inducing protective immunity in non-avian species", Vaccine, 6:497-503 (1988).
Tian, et al., "Overexpression of IL-1 a in skin differentially modulates the immune response to scasrification with vaccinia virus", J. Invest. Dermatol, 129(1):70-78 (2008).
Tiollais, et al., "The hepatitis B virus", Nature, 317:489-95 (1985).
Upton, et al., "Identification and nucleotide sequence of the thymidine kinase gene of Shope fibroma virus", J. Virology, 60:920-27 (1986).
Vijayasardahl, et al., "The melanoma antigen gp75 is the human homologue of the mouse b (brown) locus gene product", J. Exp. Med. 171(4):1375-80 (1990).
Weir, et al., "Nucleotide sequence of the vaccinia virus thymidine kinase gene and the nature of spontaneous frameshift mutations", J. Virol., 46:530-37 (1983).
Wikipedia,"Vaccinia",definition retrieved on line, Jul. 25, 2007.
Yokata, et al., "Rapid tumor penetration of a single-chain Fv and comparison with other immunoglobulin forms", Cancer Res., 52:3402-08 (1992).
Yu, et al., "Coexpression of different antigenic markers on moieties that bear CA 125 determinants", Cancer Res. 51(2):468-75 (1991).
Zagury, et al., "Immunization against AIDS in humans", Nature, 326:249-50 (1987).
International Search Report for PCT/US2012/036114 mailed Oct. 29, 2012.

(56) References Cited

OTHER PUBLICATIONS

Athle, et al., "Skin scarification with modified vaccinia Ankara virus provides superior and sadder protective immunization strategy against poxvirus challenge", J Invest. Dermatology, 128(4):S192 (2008) Abstract only.

Ennis, et al., "Primary induction of human CD8+cytotoxic T lymphocytes and interferon-gamma-producing T cells after smallpox vaccination", J Infect Diseases, 185(11):1657-9 (2002).

Hodge, et al., "Triad of costimulatory molecules synergize to amplify T-cell activation", Cancer Res., 59(1):5800-7 (1999).

* cited by examiner

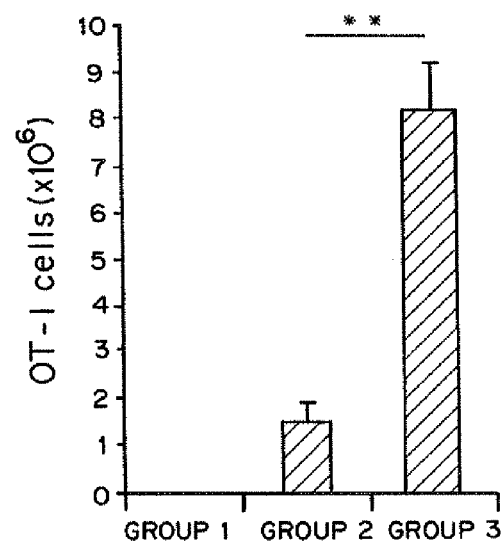
FIG. 14C
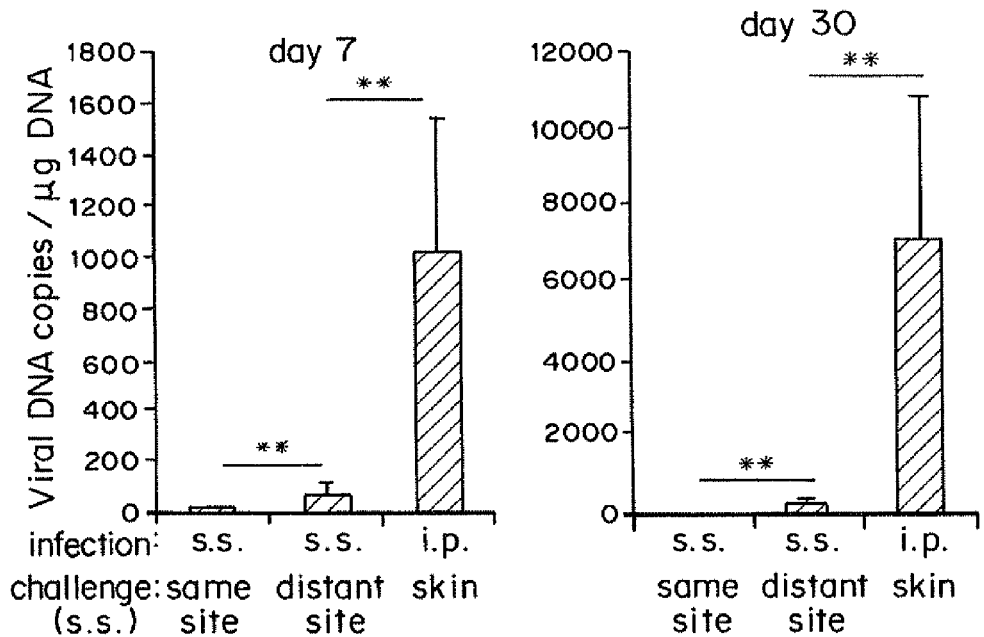
FIG. 15A
FIG. 15B

T-CELL VACCINATION WITH VIRAL VECTORS VIA MECHANICAL EPIDERMAL DISRUPTION

FEDERALLY SPONSORED RESEARCH

This invention was made in part with government support under grant numbers U19 AI057330, and 5U54AI057159-05 from the National Institute of Allergy and Infectious Diseases (NIAID) of the National Institute of Health (NIH). The United States government has certain rights to this invention.

CROSS-REFERENCE TO RELATED APPLICATIONS

This application claims priority under 35 U.S.c. 371 to PCT/US2008/012345 filed Oct. 31, 2008, the teachings of which are incorporated herein.

BACKGROUND OF INVENTION

Vaccines have traditionally consisted of live attenuated pathogens, whole inactivated organisms or inactivated toxins. In many cases these approaches have been successful at inducing immune protection based on antibody mediated responses. Virtually all current vaccines are tested for the capacity to induce a robust antibody response as a surrogate for efficacy. However, certain pathogens, e.g., HIV, HCV, TB, malaria, dengue fever, and cancer, require the induction of T cell-mediated immunity (TCMI). Killed vaccines have generally proven ineffective in producing TCMI. In addition, although live vaccines may induce TCMI, some live attenuated vaccines may cause disease in immunosuppressed subjects.

Therefore, there is an unmet need for more effective vaccines and more effective means of delivering them to result in an enhanced therapeutic efficacy and protective immune response.

SUMMARY OF INVENTION

Attenuated, replication-deficient viruses such as vaccinia viruses are used to deliver an exogenous viral, bacterial, parasitic or tumor antigen to an epidermal tissue such as the skin, lungs or gastrointestinal tract, which has been mechanically disrupted, in an amount effective to elicit or stimulate a cell mediated immune response. The epidermal tissue may be mechanically disrupted by a device such as a scarification needle or an abrader device. The epidermis may be mechanically disrupted prior to, at the same time, or immediately after the administration of the vaccine. The vaccine can be used to induce immunity against a pathogen, such as a virus, bacteria, or parasite, or against a cancer in a subject that has or is at risk of developing cancer.

In some embodiments a co-stimulatory molecule, a growth factor, an adjuvant and/or a cytokine is administered before, with or after the viral vaccine. In some embodiments, the co-stimulatory molecule is co-expressed with the antigen by the virus.

The vaccine will typically be administered to induce a primary response. In some cases, this response will be boosted by one or more subsequent administrations. Examples demonstrate that mice immunized with MVA via skin scarification developed characteristic pox lesions in a dose-dependent manner and generated dose-dependent cellular and humoral immune responses against vaccinia virus (VV) antigens. MVA skin scarification provided complete protection against mortality and illness in mice challenged with intranasal Western Reserve vaccinia virus (WR-VV) infection at a dose at which replicative VV immunization via the conventional injection routes failed to protect mice from the lethal challenge. At a comparable dose of MVA immunization, the conventional injection routes only elicited weakly detectable T cell and antibody responses, even after secondary viral challenge and offered poor protection against the WR-VV intranasal challenge, whereas strong immune protection was afforded by skin scarification with either MVA or VV. Thus, epidermal immunization with live viral vaccines, such as replication-deficient poxviruses (e.g., MVA), using mechanical disruption of the skin, generates a stronger immune response and stronger protection of the immunized host at a much lower dose compared to the injection routes currently used in the clinic, which require high doses and multiple injection regimes.

The vaccine is typically provided as a lyophylized powder in a sterile sealed vial. This may be rehydrated at the time of administration using sterile saline or water. In some embodiments, a kit comprises a device for disrupting a subject's epidermis and the live, modified, non-replicating or replication-impaired virus.

BRIEF DESCRIPTION OF DRAWINGS

(FIG. 1A) Primary T cell response: splenocytes harvested on day 7 following immunization (p.i.) were restimulated with VV-infected target cells (splenocytes from naïve mice) for 6 hours in the presence of brefelding A to measure the frequency of IFN-γ producing CD8 T cells by intracellular cytokine staining UI: unimmunized mice. (FIG. 1B). Memory VV-specific T cell activity was assessed at 5 week p.i. Splenocytes from immunized mice were restimulated with VV-infected target cells for 48 h and supernatant were harvested. IFN-γ production in supernatant was measured by ELISA. (FIG. 1C-1D). Serum VV-specific IgG level was determined at the indicated time points p.i. by ELISA.

(FIG. 3A-3B) B6 mice were immunized by VV via various routes at $2 c 10^6$ pfu dose Immune mice were lethally challenged with intranasal infection of WR-VV at 6 weeks p.i. The survival (FIG. 1A) and change of bodyweight (BW) (FIG. 3B) were monitored daily after challenge. (FIG. 3C-3D) B6 mice were immunized by VV via skin scarification at the indicated doses, and lethally challenged with intranasal WR-VV infection at 6 weeks p.i. The survival (FIG. 3C) and change of BW (FIG. 3D) were monitored daily after challenge. Unimmunized mice were included as controls.

(FIG. 5A) Viral load at the challenged sites were determined on day 6 after challenge. In some groups of wt mice, both CD4$^+$ and CD8$^+$ T cells were depleted before the challenge. (FIG. 5B-5C) Secondary T cell response in challenged wt and mMt immune mice was assessed in skin-draining inguinal lymph nodes and spleen on day 6 following challenged. Skin samples were harvested from the challenged site at 4 days after challenge. Skin-infiltrating CD3$^+$ T cells were identified by immunohistochemistry.

(FIG. 7A) 60 hours after the infection, proliferation of OT-1 cells in ILN, and MLN were shown by Histograms gated on Thy1.1$^+$ donor cells. (b-c) ILN of skin scarified mice (FIG. 7B) and MLN of i.p.-infected mice (FIG. 7C) were analyzed at 60 h after rVV-ova infection for OT-1 tissue-homing phenotype. Dot plots were gated on Thy1.1$^+$ cells. The numbers in quadrant indicate the percentages in Thy1.1$^+$ population. (FIG. 7D) The geometric mean fluorescence intensities (GMF1) of the indicated markers on OT-1 cells were plotted with the cell division cycles.

(FIG. 9A), the expression of E-Lig and (FIG. 9B) α4β7 (FIG. 9C) on OT-1 cells in ILN were measured.

(FIG. 11A) B6 mice were immunized with MVA or VV by s.s. at the indicated doses (pfu/mouse) 7 days post-immunization, primary vaccinia-specific T cell response was measured in spleens. (FIG. 11A) Serum vaccinia—specific IgG was measured at 6 weeks post-immunization. (FIG. 11B) mice were challenged with lethal i.n. infection with WR-VV at 6 weeks after immunization. Survival (FIG. 11C) and change of BW (FIG. 11D) were monitored daily.

(FIG. 12A) primary T cell response was measured on day 7 p.i. (FIG. 12B) VV-specific IgG was measured at 6 weeks p.i. Memory mice were intranasally challenged with lethal dose of WR-VV at 6 weeks p.i. Secondary T cell response (FIG. 12C) and post-challenge VV-specific IgG (FIG. 12D) were measured on day 6 challenge. Survival (FIG. 12E) and BW change (FIG. 12F) were monitored daily after challenge. VV skin scarified mice (2×10$^6$ pfu) mice were included as controls.

FIG. 14C is a graph of the results for all infection routes are s.s. 30 days after challenge. Thy1.1+ OT-I cells were examined by analyzing their absolute numbers in uninfected right ears. Group 1: only Thy1.1+ OT-I cells. Group 2: Thy1.1 OT-I cells+left ear infection. Group 3: OT-I cells+left ear/tail/flank infections. n=5 per group. **: P<0.01. Results are representative of three independent experiments.

FIGS. 15A and 15B are graphs of the results for B-cell-deficient μMT mice infected with 2×10⁶ PFU VACV by s.s. on the left ears or i.p. injection route. 7 or 30 days later, the immunized mice were challenged with 2×10⁶ PFU VACV on both ears by s.s. route. 1 mg/kg FTY720 were intraperitoneally injected each day. 6 days after challenge, virus titers in both ears were examined (B). n=5 per group. **: P<0.01. Results are representative of two independent experiments.

DETAILED DESCRIPTION OF THE INVENTION

Figure 1A:
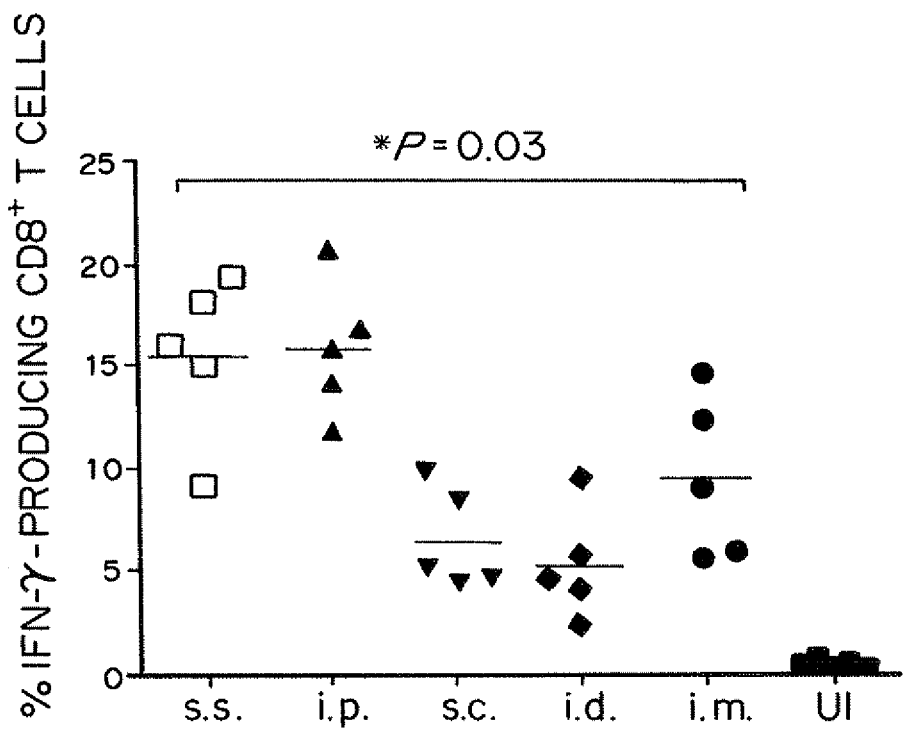
FIG. 1A-D. Vaccinia virus inoculation via skin scarification is superiorly immunogenic compared to other immunization routes. C57BL/6 (B6) mice were immunized by VV at $2 \times 10^6$ pfu dose by the indicated routes. s.s.: skin scarification; i.p.: intraperitoneal injections; s.c.: subcutaneous injections; i.d.: interdermal injection; i.m.: intramuscular injection.
Figure 1B:
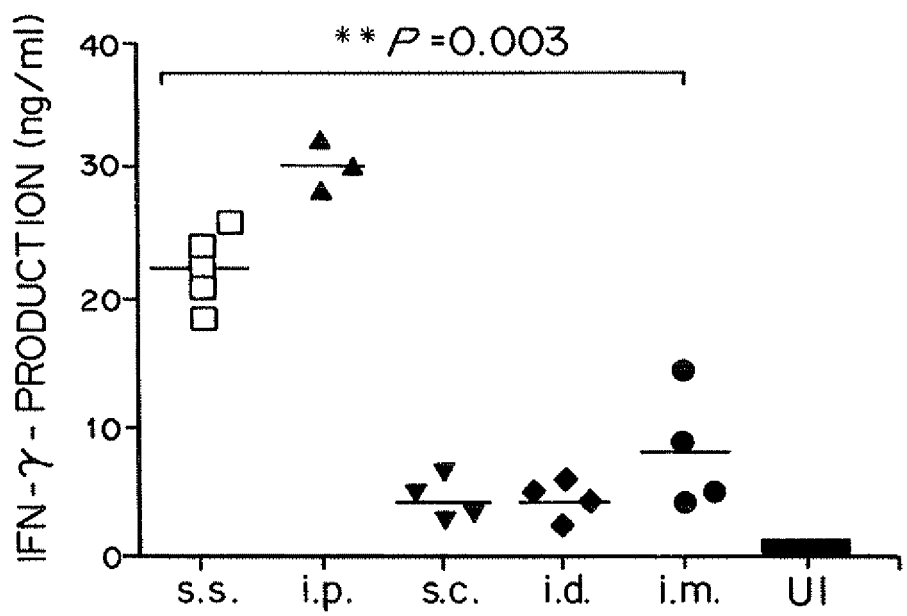
Figure 1C:
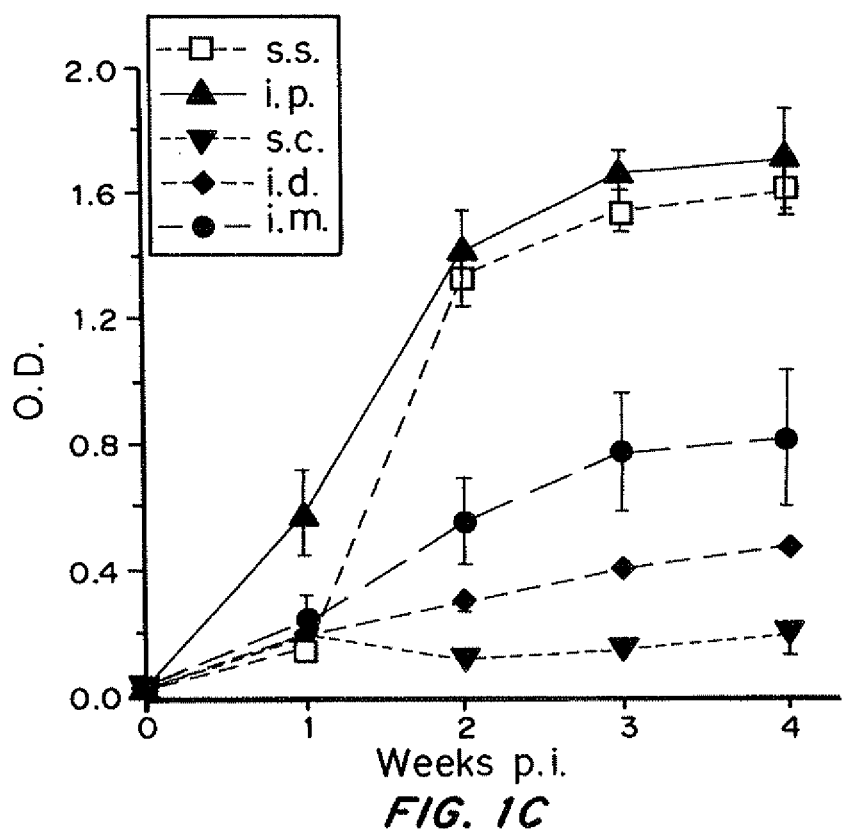
Figure 1D:
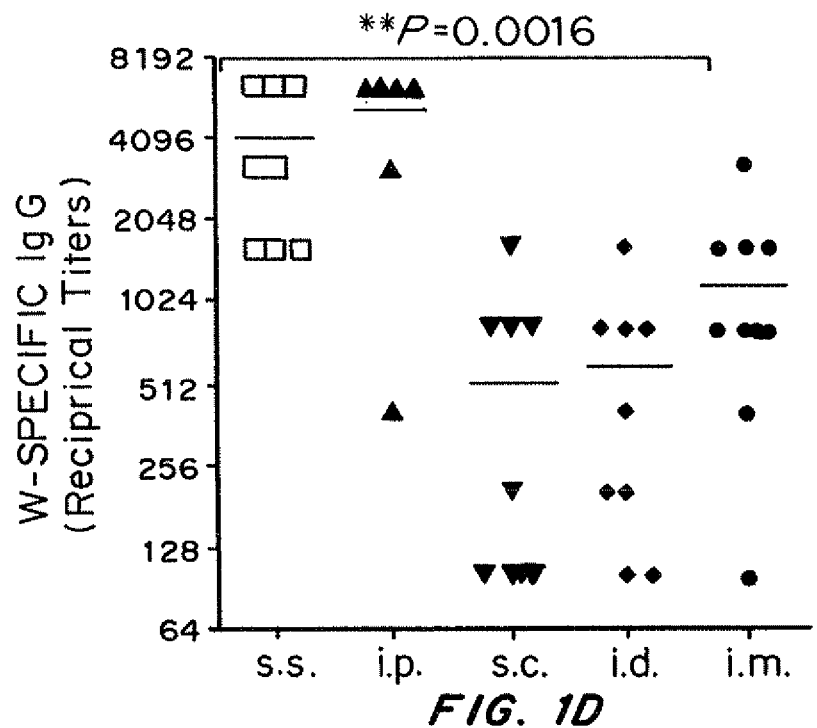

Adaptive immune memory that protects against microbial infection is traditionally thought to be mediated by T cells circulating in blood and through secondary lymphoid tissues. According to this view, while memory T cells can be readily mobilized from blood to peripheral epithelial tissues to fight infection, they would return to blood and lymph nodes once the infection was resolved. Very recently, it has been demonstrated that memory T cells can be found in abundance in the peripheral tissues of both humans and mice, with the majority of this work being done in skin. Under normal conditions, twice as many T cells reside in normal human skin as in blood. Skin-homing memory T cells are 20-fold more abundant in normal skin than in blood. These skin resident memory T cells (TRM) have a diverse T cell receptor repertoire, can be readily activated through the TCR or by cytokines, are polyfunctional, and have great proliferative potential. TRM are not simply memory T cells in an unexpected location. Rather, they are an unique and incompletely characterized population, having many functional and phenotypic qualities that differentiate them from memory T cells that circulate in blood. Similar populations of TRM exist in lung and GI tract, as well as reproductive mucosa.

There is a growing body of evidence in murine models suggesting that T cells are recruited to skin and other epithelial tissues after pathogen challenge, and then can persist there long term as TRM. At least two separate studies examining viral infection of skin have demonstrated that these TRM, rather than antibody or TCM recruited from blood, provide principal protection against viral challenge, even many months after resolution of the initial infection. Similar populations of T cells are identified after infection in lung, GI tract, and CNS. These TRM consist largely of T cells that were originally (as naïve T cells) activated in lymph nodes draining that tissue, and thus represent a resident armada of tissue specific T cells specific for tissue selective pathogens.

A method has been developed based on the discovery that protective immune memory is mediated largely by TRM that have accumulated over time in epithelial tissues. The body has several epithelial surfaces that interface with the environment. The most accessible is skin, but continuous with skin is the oropharyngeal mucosal epithelium, the female reproductive epithelium, and the large and complex epithelial tissues that line the respiratory and gastrointestinal tracts. For pathogens to gain access to blood and internal tissues, they must infect and then breach one or more of these epithelial barriers. While each of these epithelial tissues is structurally different and employs different innate immune defenses, the adaptive immune system mediates lifelong protection against pathogen attack, through T cell memory and B cell antibody production. Twice as many T cells reside in normal, non-inflamed human skin as in blood, and for skin homing memory T cells, there are more than 20-fold more of such T cells in normal skin than in blood. These skin resident T cells ($T_{RM}$) have a diverse T cell receptor repertoire, can be readily activated through the TCR or by cytokines, and have great proliferative potential. Moreover, they are polyfunctional with regard to cytokine production, suggesting their authentic role as memory T cells that protect against infection. Evidence is accumulating that similar populations of $T_{RM}$ exist in lung and GI tract, as well as reproductive mucosa. The vaccination strategies against pathogens and tumors are designed specifically to enhance the generation of these peripheral epithelial TRM.

Protective memory T cells have previously been thought to reside in blood and lymph nodes. However, most pathogens are not encountered through blood, but rather through epithelial-environmental interfaces, including skin, gut, lung and the reproductive tract. $T_{RM}$ are not simply memory T cells in an unexpected location; rather, they have many distinct functional and phenotypic qualities that differentiate them from conventional memory T cells In murine models of viral challenge in previously immunized mice, it has been demonstrated that both antibodies and circulating central memory T cells ($T_{CM}$) are dispensable, and TRM play the major role in protecting the host from infection. The data demonstrates that in the same organism, TRM are much more effective than TCM at fighting off infection.

T cell recruitment into extranodal peripheral tissues is a highly regulated process controlled by the sequential interactions of adhesion molecules and chemokine receptors that are differentially expressed on various T cell subsets and their target. Human skin-homing T cells express cutaneous lymphocyte antigen (CLA) which binds to skin microvasculature-expressed E-selectin, typically in combination with CCR4 whose ligand CCL17 (TARC) is constitutively expressed on skin endothelium. Gut-homing T cells express α4β7 integrin and chemokine receptor CCR9, to which the corresponding ligands MadCAM-1 and CCL25 (TECK) are expressed on the endothelium and epithelium of the small intestine Following VACV skin scarification, the skin homing molecules E- and P-selectin ligands (E-lig and P-lig, the functional murine equivalents of human CLA) are strongly upregulated on antigen-specific CD8 T cells between the $3^{rd}$ and $10^{th}$ cell divisions in the regional LN draining the scarified site. Subsets of proliferating VV specific CD8 T cells leave the draining inguinal node after as few as three cell divisions and migrate through blood to skin ($T_{EM}$), or to other LN ($T_{CM}$), respectively. In these distant LN, vaccinia-specific $T_{CM}$ cells continue to proliferate, in the absence of continued antigen receptor stimulation, and acquire homing receptors consistent with the regional drainage of the LN they have migrated to; e.g., β-integrin in mesenteric LN. Thus, generalized CD8 T cell mediated immunity to a local challenge is acquired by systemic dissemination of activated T cells from the local draining LN. The tissue homing properties of these cells then are imprinted in the respective LN environments to which they disseminate.

I. DEFINITIONS

As used herein, an immune response is

As used herein, a T cell antigen is a protein or fragement thereof which can be processed into a peptide that can bind to either Class I MHC, Class II MHC, non-classical MHC, or CD1 family molecules (collectively antigen presenting molecules), and in this combination can engage a T cell receptor on a T cell.

As used herein, a B cell antigen is a protein, glycoprotein, carbohydrate, or lipid that can bind to cell surface antibody and can generate the production of soluble antibodies.

As used herein, a T cell mediated immune response is a response that occurs as a result of recognition of a T cell antigen bound to an antigen presenting molecule on the cell surface of an antigen presenting cell, coupled with other interactions between costimulatory molecules on the T cell and APC. This response serves to induce T cell proliferation, anatomic migration, and production of effector molecules, including cytokines and other factors that can injure cells.

As used herein, a humoral immune response is the generation of an immune response that leads to high and sustained levels of circulating antibodies.

"To treat" or "treatment" of a disease as used herein refers to improving one or more symptoms or the general condition of a subject having the disease. In the case of cancer, "treating" the cancer refers to inhibiting proliferation or metastasis of a cancer or tumor cells. Treatment may lead to stasis, partial or complete remission of a tumor or may inhibit metastatic spreading of the tumor.

In the case of an infectious disease, "treating" the infectious disease means reducing the load of the infections agent in the subject. The load may be viral load, and reducing the viral load means, for example, reducing the number of cells infected with the virus, reducing the rate of replication of the virus, reducing the number of new virions produced, or reducing the number of total viral genome copies in a cell, as compared to an untreated subject. The load may be bacterial, yeast, fungi, protozoa, helminths, or parasite load, and reducing such load means, for example, reducing the number of bacteria, fungi, protozoa, helminths, yeast or parasites in a host, reducing the rate of population growth, reducing the spread throughout the subject's body, reducing the amount of toxic products produced by the bacteria, yeast, fungi, protozoa, helminths or parasites, as compared to an untreated subject.

"To protect" or "protection of" a subject from developing a disease or from becoming susceptible to an infection as referred herein means to partially or fully protect a subject. As used herein, to "fully protect" means that a treated subject does not develop a disease or infection caused by an agent such as a virus, bacterium, fungus, protozoa, helminth, and parasites, or caused by a cancer cell. To "partially protect" as used herein means that a certain subset of subjects may be fully protected from developing a disease or infection after treatment, or that the subject does not develop a disease or infection with the same severity as an untreated subject.

As used herein, the term "non-replicating" or "replication-impaired" poxvirus refers to a poxvirus that is not capable of replication to any significant extent in the majority of normal mammalian cells or normal primary human cells.

As used herein "significant extent" means a replication capability of 75% or less as compared to wild-type vaccinia virus in standardized assays.

In some embodiments, the poxvirus has a replication capability of 65%, 55%, 45%, 35%, 25%, or 15% compared to wild-type vaccinia virus.

As used herein a "modified" virus refers to a poxvirus that has been altered in some way that changes one or more characteristics of the modified virus compared to the wild-type virus. These changes may have occurred naturally or through engineering. In some embodiments, the modified virus is altered to include an antigen(s) that are immunogenic (i.e., induce an immune response in a host). Antigens include, for example, cancer antigens or microbial antigens.

II. FORMULATIONS

A. Viral Vectors

Several different replication deficient or live, modified, non-replicating or replication-impaired vectors can be used. Because poxviruses have a large genome, they can readily be used to deliver a wide range of genetic material including multiple genes (i.e., act as a multivalent vector). The sizes of the poxvirus genomes ranges between about 130-300 kbp with up to 300 genes, depending on the strain of the virus. Therefore, it is possible to insert large fragments of foreign DNA into these viruses and yet maintain stability of the viral genome.

Poxviruses are useful vectors for a range of uses, for example vaccines to generate immune responses, for the development of new vaccines, for delivery of desired proteins and for gene therapy. The advantages of poxvirus vectors include: (i) ease of generation and production, (ii) the large size of the genome permitting insertion of multiple genes (i.e., as a multivalent vector), (iii) efficient delivery of genes to multiple cell types, including antigen-presenting cells, (iv) high levels of protein expression, (v) optimal presentation of antigens to the immune system, and (vi) the ability to elicit cell-mediated immune responses as well as antibody responses, (vii) the ability to use combinations of poxviruses from different genera, as they are not immunologically cross-reactive and (viii) the long-term experience gained with using this vector in humans as a smallpox vaccine.

Poxviruses can be genetically engineered to contain and express foreign DNA with or without impairing the ability of the virus to replicate. Such foreign DNA can encode a wide range of proteins, such as antigens that induce protection against one or more infectious agents, immune modulating proteins such as co-stimulatory molecules, or enzymatic proteins. For example, recombinant vaccinia viruses have been engineered to express antigens of herpesvirus, hepatitis B, rabies, influenza, human immunodeficiency virus (HIV), and other viruses (Kieny et al., Nature 312:163-6 (1984); Smith et al., Nature 302: 490-5 (1983); Smith et al., Proc. Natl. Acad. Sci. USA 80:7155-9 (1983); Zagury et al., Nature 326:249-50 (1987); Cooney et al., Lancet 337:567-72 (1991); Graham et al., J. Infect. Dis. 166:244-52 (1992), and have been shown to elicit immune responses against influenza virus, dengue virus, respiratory syncytial virus, and human immunodeficiency virus (HIV) when injected. Poxviruses have also been injected to generate immune reactions against tumor-associated antigens such as CEA, PSA and MUC.

Poxviruses are well known cytoplasmic viruses. The genetic material expressed by such viral vectors typically remains in the cytoplasm and does not have the potential for inadvertent integration of the genetic material into host cell genes, unless specific steps are taken. As a result of the non-integrative cytoplasmic nature of the poxvirus, the poxvirus vector system will not result in having long term persistence in other cells. Thus, the vector and the transformed cells will not adversely affect cells in the host animal at locations distant from the target cell. Compared to other systems such as retrovirus vectors (including lentiviral vectors), adenoviral vectors, and adeno-associated virus vectors, the large genome of poxviruses enables large genes to be inserted into pox-based vectors.

A number of poxviruses have been developed as live viral vectors for the expression of heterologous proteins, e.g. attenuated vaccinia virus strains Modified Vaccinia Ankara (MVA) and Wyeth (Cepko et al., Cell 37:1053 1062 (1984); Morin et al., Proc. Natl. Acad. Sci. USA 84:4626 4630 (1987); Lowe et al., Proc. Natl. Acad. Sci. USA, 84:3896 3900 (1987); Panicali & Paoletti, Proc. Natl. Acad. Sci. USA, 79:4927 4931 (1982); Mackett et al., Proc. Natl. Acad. Sci. USA, 79:7415 7419 (1982)). Other attenuated vaccinia virus strains include WR strain, NYCBH strain, ACAM2000, Lister strain, LC16 m8, Elstree-BNm, Copenhagen strain, and Tiantan strain.

Vaccinia virus is the prototype of the genus *Orthopoxvirus*. It is a double-stranded DNA (deoxyribonucleic acid) virus that has a broad host range under experimental conditions (Fenner et al. Orthopoxviruses. San Diego, Calif.: Academic Press, Inc., 1989; Damaso et al., Virology 277:439-49 (2000)). Modified vaccinia virus Ankara (MVA) or derivatives thereof have been generated by long-term serial passages of the Ankara strain of vaccinia virus (CVA) on chicken embryo fibroblasts (for review see Mayr, A., et al., Infection, 3:6-14 (1975). The MVA virus itself may be obtained from a number of public repository sources. For example, MVA was deposited in compliance with the requirements of the Budapest Treaty at CNCM (Institut Pasteur, Collection Nationale de Cultures Microorganisms, 25, rue du Docteur Roux, 75724 Paris Cedex 15) on Dec. 15, 1987 under Depositary No. 1-721 (U.S. Pat. No. 5,185,146); MVA virus was deposited in compliance with the Budapest Treaty at the European Collection of Cell Cultures (ECACC) (CAMR, Porton Down, Salisbury, SP4 OJG, UK) on Jan. 27, 1994, under Depository No. V94012707) (U.S. Pat. No. 6,440,422 and United States patent publication number 2003/0013190). Also, United States patent publication number 2003/0013190 further discloses particular MVA strains deposited at the ECACC under Depository No. 99101431, and ECACC provisional accession number 01021411. Commercially available are THERION-MVA, THERION PRIFREE vectors and THERION M-SERIES vectors (Therion Biologics Corporation, MA).

MVA was generated by 516 serial passages on chicken embryo fibroblasts of the Ankara strain of vaccinia virus (CVA) (Mayr, A., et al. Infection 3, 6-14 [1975]). As a consequence of these long-term passages, about 31 kilobases of the genomic sequence were deleted from the virus (deletion I, II, III, IV, V, and VI) and, therefore, the resulting MVA virus was described as being highly host cell restricted to avian cells (Meyer, H. et al., J. Gen. Virol. 72, 1031-1038 [1991]). It was shown in a variety of animal models that the resulting MVA was significantly avirulent (Mayr, A. & Danner, K. [1978] Dev. Biol. Stand. 41: 225-34). Additionally, this MVA strain has been tested in clinical trials as a vaccine to immunize against the human smallpox disease (Mayr et al., Zbl. Bakt. Hyg. I, Abt. Org. B 167, 375-390 [1987], Stickl et al., Dtsch. med. Wschr. 99, 2386-2392 [1974]). These studies involved over 120,000 humans, including high-risk patients, and proved that compared to vaccinia based vaccines, MVA had diminished virulence or infectiousness while it induced a good specific immune response. Generally, a virus strain is regarded as attenuated if it has lost its capacity or only has reduced capacity to reproductively replicate in host cells.

Because the genome of both wild type VV and MVA have both been sequenced, it is possible to clone viruses that bear some resemblence to MVA with regard to replication properties, but are genetically distinct from MVA. These may serve the same purpose, or may be more immunogenic than MVA while being just as safe by virtue of their replicaton deficiency.

In some embodiments, the virus has a replication capability 5% or less, or 1% or less compared to wild-type virus. Non-replicating viruses are 100% replication deficient in normal primary human cells.

Viral replication assays are known in the art, and can be performed for vaccinia viruses on e.g. primary keratinocytes, and are described in Liu et al. J. Virol. 2005, 79:12, 7363-70. Viruses which are non-replicating or replication-impaired may have become so naturally (i.e. they may be isolated as such from nature) or artificially e.g. by breeding in vitro or by genetic manipulation, for example deletion of a gene which is critical for replication. There will generally be one or a few cell types in which the viruses can be grown, such as CEF cells for MVA.

In some embodiments, changes in the virus include, for example, alterations in the gene expression profile of the virus. In some embodiments, the modified virus may express genes or portions of genes that encode peptides or polypeptides that are foreign to the poxvirus, i.e. would not be found in a wild-type virus. These foreign, heterologous or exogenous peptides or polypeptides can include sequences that are immunogenic such as, for example, tumor-specific antigens (TSAs), bacterial, viral, fungal, and protozoal antigens, or antigenic sequences derived from viruses other than the viral vector. The genetic material may be inserted at an appropriate site within the virus genome for the recombinant virus to remain viable, i.e. the genetic material may be inserted at a site in the viral DNA (e.g., non-essential site in the viral DNA) to ensure that the recombinant virus retains the ability to infect foreign cells and to express DNA, while maintaining the desired immunogenicity and diminished virulence. For example, as described above, MVA contains 6 natural deletion sites which have been demonstrated to serve as insertion sites. See, for example, U.S. Pat. No. 5,185,146, and U.S. Pat. No. 6,440,422. In some embodiments, genes that code for desired antigens are inserted into the genome of a poxvirus in such a manner as to allow them to be expressed by that virus along with the expression of the normal complement of parent virus proteins.

The viruses have a low replicative efficiency in the target cell, which prevents sustained replication and infection of other cells. In some embodiments, the modified poxvirus may also have altered characteristics concerning aspects of the viral life cycle, such as target cell specificity, route of infection, rate of infection, rate of replication, rate of virion assembly and/or rate of viral spreading.

In some embodiments, the inserted gene(s) encoding antigens may be operably linked to a promoter to express the inserted gene. Promoters are well known in the art and can readily be selected depending on the host and the cell type one wishes to target. For example in poxviruses, poxyiral promoters may be used, such as the vaccinia 7.5K, 40K, fowlpox. In certain embodiments, enhancer elements can also be used in combination to increase the level of expression. In certain embodiments, inducible promoters, which are also well known in the art, may be used. Representative poxvirus promoters include an entomopox promoter, an avipox promoter, or an orthopox promoter such as a vaccinia promoter, e.g., HH, 11K or Pi. For example, the Pi promoter, from the Ava I H region of vaccinia, is described in Wachsman et al., J. of Inf. Dis. 155, 1188-1197 (1987). This promoter is derived from the Ava I H (Xho I G) fragment of the L-variant WR vaccinia strain, in which the promoter directs transcription from right to left. The map location of the promoter is approximately 1.3 Kbp (kilobase pair) from the 5' end of Ava IH, approximately 12.5 Kbp from the 5' end of the vaccinia genome, and about 8.5 Kbp 5' of the Hind III C/N junction. The Hind III H promoter (also "HH" and "H6" herein) sequence is an upstream of open reading frame H6 by Rosel et al., J. Virol. 60, 436-449 (1986). The 11K promoter is as described by Wittek, J. Virol. 49, 371-378 (1984) and Bertholet, C. et al., Proc. Natl. Acad. Sci. USA 82, 2096-2100 (1985). One can take advantage of whether the promoter is an early or late promoter to time expression of particular genes.

In some embodiments, the promoter is modulated by an external factor or cue, allowing control of the level of polypeptide being produced by the vectors by activating that external factor or cue. For example, heat shock proteins are proteins encoded by genes in which the promoter is regulated by temperature. The promoter of the gene which encodes the metal-containing protein metallothionine is responsive to $Cd^+$ ions. Incorporation of this promoter or another promoter influenced by external cues also makes it possible to regulate the production of the polypeptides comprising antigen.

In some embodiments, the nucleic acid encoding at least one gene of interest encoding, e.g. an antigen, is operably linked to an "inducible" promoter. Inducible systems allow careful regulation of gene expression. See, Miller and Whelan, Human Gene Therapy, 8:803-815 (1997). The phrase "inducible promoter" or "inducible system" as used herein includes systems wherein promoter activity can be regulated using an externally delivered agent. Such systems include, for example, systems using the lac repressor from *E. coli* as a transcription modulator to regulate transcription from lac operator-bearing mammalian cell promoters (Brown et al. Cell, 49:603-612, 1987); systems using the tetracycline repressor (tetR)(Gossen and Bujard, Proc. Natl. Acad. Sci. USA 89: 5547-5551, 1992; Yao et al., Human Gene Ther. 9:1939-1950, 1998; Shokelt et al., Proc. Natl. Acad. Sci. USA 92.6522-6526, 1995). Other such systems include FK506 dimer, VP16 or p65 using castradiol, RU486/mifepristone, diphenol muristerone or rapamycin. Another example is an ecdysone inducible system (see, e.g. Karns et al, MBC Biotechnology 1:11, 2001). Inducible systems are available, e.g., from Invitrogen, Clontech, and Ariad. Systems using a repressor with the operon are preferred. These promoters may be adapted by substituting portions of pox promoters for the mammalian promoter.

In some embodiments, a "transcriptional regulatory element" or "TRE" is introduced for regulation of the gene of interest. A TRE is a polynucleotide sequence, preferably a DNA sequence, that regulates transcription of an operably-linked polynucleotide sequence by an RNA polymerase to form RNA. A TRE increases transcription of an operably linked polynucleotide sequence in a host cell that allows the TRE to function. The TRE comprises an enhancer element and/or viral promoter element, which may or may not be derived from the same gene. The promoter and enhancer components of a TRE may be in any orientation and/or distance from the coding sequence of interest, and comprise multimers of the foregoing, as long as the desired, transcriptional activity is obtained.

In some embodiments, an "enhancer" for regulation of the gene of interest is provided. An enhancer is a polynucleotide sequence derived from a gene which increases transcription of a gene which is operably-linked to a promoter to an extent which is greater than the transcription activation effected by the promoter itself when operably-linked to the gene, i.e. it increases transcription from the promoter.

The activity of a regulatory element such as a TRE or an enhancer generally depends upon the presence of transcriptional regulatory factors and/or the absence of transcriptional regulatory inhibitors. Transcriptional activation can be measured in a number of ways known in the art, but is generally measured by detection and/or quantification of mRNA or the protein product of the coding sequence under control of (i.e., operatively linked to) the regulatory element. The regulatory element can be of varying lengths, and of varying sequence composition. By transcriptional activation, it is intended that transcription will be increased above basal levels in the target cell by at least about 2-fold, preferably at least about 5-fold, preferably at least about 10-fold, more preferably at least about 20-fold. More preferably at least about 50-fold, more preferably at least about 100-fold, even more preferably at least about 200-fold, even more preferably at least about 400- to about 500-fold, even more preferably, at least about 1000-fold. Basal levels are generally the level of activity, if any, in a non-target cell, or the level of activity (if any) of a reporter construct lacking the TRE or enhancer of interest as tested in a target cell type.

Certain point mutations within sequences of TREs decrease transcription factor binding and gene activation. One of skill in the art would recognize that some alterations of bases in and around known the transcription factor binding sites are more likely to negatively affect gene activation and cell-specificity, while alterations in bases which are not involved in transcription factor binding are not as likely to have such effects. Certain mutations also increase TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription.

B. Antigens

Any DNA of interest can be inserted into the viral vector described herein. Foreign genes for insertion into the genome of a virus in expressible form can be obtained using conventional techniques for isolating a desired gene. For organisms which contain a DNA genome, the genes encoding an antigen of interest may be isolated from the genomic DNA; for organisms with RNA genomes, the desired gene may be isolated from cDNA copies of the genome. If restriction maps of the genome are available, strategies can be designed for cleaving genomic DNA by restriction endonuclease digestion to yield DNA fragments that contain the gene of interest. In some cases, desired genes have been previously. Alternatively, if the DNA sequence of the gene is known, the gene can be synthesized by any of the conventional techniques for polymerase chain reaction or synthesis of deoxyribonucleic acids (e.g., the phosphate or phosphite triester techniques). In some embodiments, nucleic acids are provided that express antigenic domains rather than the entire protein. These fragments may be of any length sufficient to be immunogenic or antigenic. Fragments may be at least four amino acids long, preferably 5-9 amino acids, but may be longer, such as e.g. 10, 11, 12, 13, 14, 15, 16, 17, 18, 19, 20, 30, 40, 50, 60, 70, 80, 90, 100, 500 amino acids long or more, or any length in between. Epitopes that induce a protective immune response to a pathogen such as bacteria, viruses, fungi or protozoae or to a cancer antigen may be combined with heterologous gene sequences that encode proteins with immunomodulating activities, such as cytokines, interferon type 1, gamma interferon, colony stimulating factors, interleukin-1, -2, -4, -5, -6, -12.

In some embodiments, at least one nucleic acid fragment encoding a gene is inserted into a viral vector. In another embodiment at least two and up to about ten different nucleic acids encoding different genes are inserted into the viral vector. In some embodiments, multiple immunogenic fragments or subunits of various proteins may be used. For example, several different epitopes from different sites of a single protein or from different proteins of the same species, or from a protein ortholog from different species may be expressed.

1. Cancer Antigens

In some embodiments, genes of interest are those which encode tumor-associated antigens (TAAs), tumor specific antigens (TSAs), tissue-specific antigens, viral tumor antigens, cellular oncogene proteins, and/or tumor-associated differentiation antigens. These antigens can serve as targets for the host immune system and elicit responses which result in tumor destruction. This immune response is mediated primarily by lymphocytes; T cells in general and class I MHC-restricted cytotoxic T lymphocytes in particular play a central role in tumor rejection. Hellstrom, K. E., et al., (1969) Adv. Cancer Res. 12:167 223; Greenberg, P. D. (1991) in Advances in Immunology, vol. 49 (Dixon, D. J., ed.), pp. 281 355, Academic Press, Inc., Orlando, Fla. The cloning of TAAs for cancer immunotherapy is described e.g. in Boon, T., et al., (1994) Annu. Rev. Immunol. 12:337 365; Brithcard, V., et al., (1993) J. Exp. Med. 178:489 495; Cox, A. L., et al., (1994) Science 264:716 719; Houghton, A. N. (1994) J. Exp. Med. 180:1 4; Pardoll, D. M. (1994) Nature 369:357 358; Kawakami, Y., et al., (1994) Proc. Natl. Acad. Sci. U.S.A. 91:3515 3519; Kawakami, Y., et al., (1994) Proc. Natl. Acad. Sci. U.S.A. 91:6458 6462.

In general, viral vaccines are believed to mediate tumor rejection by activating class I MHC-restricted T-cells, particularly cytotoxic T lymphocytes (CTLs). T-cell activation is often potentiated by providing a suitable immunomodulator, for example a T-cell co-stimulatory factor such as those of the B7 gene family. See e.g., Greenberg, P. D. (1991) in Advances in Immunology, Vol. 49 (Dixon, D. J., ed.), pp. 281 355, Academic Press, Inc., Orlando, Fla.; Fox B. A. et al. (1990) J. Biol. Response Mod. 9:499 511. The use of vaccinia viruses for anti-tumor immunotherapy has been described in Hu, S. L., Hellstrom, I., and Hellstrom K. E. (1992) in Vaccines: New Approaches to Immunological Problems (R. W. Ellis, ed) pp. 327 343, Butterworth-Heinemann, Boston. Anti-tumor responses have been elicited using recombinant pox viruses expressing TAAs such as carcinoembryonic antigen (CEA) and prostrate specific antigen (PSA). (Muraro, R., et al., (1985) Cancer Res. 4S:5769 5780); (Kantor, 3., et al. (1992) J. Natl. Cancer Inst. 84:1084 1091); (Robbins, P. F., et al. (1991) Cancer Res. 51:3657 3662) (Kantor, 3., et al. (1992) Cancer Res. 52:6917 6925.) No toxicity with these vectors was observed. However, in all cases the vaccines were injected.

These antigens include, but are not limited to, melanoma TAAs such as MART-1 (Kawakami et al. J. Exp. Med. 180: 347-352, 1994), MAGE-1, MAGE-3, GP-100, (Kawakami et al. Proc. Nat'l. Acad. Sci. U.S.A. 91:6458-6462, 1994), tyrosinase (Brichard et al. J. Exp. Med. 178:489, 1993), TAAs such as MUC-1, MUC-2, MUC-3, MUC-4, MUC-18, the point mutated ras oncogene and the point mutated p53 oncogenes (pancreatic cancer), PSA (prostate cancer), c-erb/B2 (breast cancer), KS ¼ pan-carcinoma antigen (Perez and Walker, 1990, J. Immunol. 142:3662-3667; Bumal, 1988, Hybridoma 7(4):407-415), ovarian carcinoma antigen (CA125) (Yu et al., 1991, Cancer Res. 51(2):468-475), prostatic acid phosphate (Tailor et al., 1990, Nucl. Acids Res. 18(16):4928), prostate specific antigen (PSA) (Henttu and Vihko, 1989, Biochem. Biophys. Res. Comm. 160(2):903-910; Israeli et al., 1993, Cancer Res. 53:227-230), melanoma-associated antigen p97 (Estin et al., 1989, J. Natl. Cancer Instit. 81(6):445-446), melanoma antigen gp75 (Vijayasardahl et al., 1990, J. Exp. Med. 171(4):1375-1380), high molecular weight melanoma antigen (HMW-MAA) (Natali et al., 1987, Cancer 59:55-63; Mittelman et al., 1990, J. Clin. Invest. 86:2136-2144), prostate specific membrane antigen, carcinoembryonic antigen (CEA) (Foon et al., 1994, Proc. Am. Soc. Clin. Oncol. 13:294), polymorphic epithelial mucin antigen, human milk fat globule antigen, colorectal tumor-associated antigens such as TAG-72 (Yokata et al., 1992, Cancer Res. 52:3402-3408), C017-1A (Ragnhammar et al., 1993, Int. J. Cancer 53:751-758); GICA 19-9 (Herlyn et al., 1982, J. Clin. Immunol. 2:135), CTA-1 and LEA, Burkitt's lymphoma antigen-38.13, CD19 (Ghetie et al., 1994, Blood 83:1329-1336), human B-lymphoma antigen-CD20 (Reff et al., 1994, Blood 83:435-445), CD33 (Sgouros et al., 1993, J. Nucl. Med. 34:422-430), melanoma specific antigens such as ganglioside GD2 (Saleh et al., 1993, J. Immunol., 151, 3390-3398), ganglioside GD3 (shitara et al., 1993, Cancer Immunol. Immunother. 36:373-380), ganglioside GM2 (Livingston et al., 1994, J. Clin. Oncol. 12:1036-1044), ganglioside GM3 (Hoon et al., 1993, Cancer Res. 53:5244-5250), tumor-specific transplantation type of cell-surface antigen (TSTA) such as virally-induced tumor antigens including T-antigen DNA tumor viruses and Envelope antigens of RNA tumor viruses, bladder tumor oncofetal antigen (Hellstrom et al., 1985, Cancer. Res. 45:2210-2188), differentiation antigen such as human lung carcinoma antigen L6, L20 (Hellstrom et al., 1986, Cancer Res. 46:3917-3923), antigens of fibrosarcoma, human leukemia T cell antigen-Gp37 (Bhattacharya-Chatterjee et al., 1988, J. of Immuno specifically. 141:1398-1403), neoglycoprotein, sphingolipids, breast cancer antigen such as EGFR (Epidermal growth factor receptor), HER2 antigen (p185$^{HER2}$), polymorphic epithelial mucin (PEM) (Hilkens et al., 1992, Trends in Bio. Chem. Sci. 17:359), malignant human lymphocyte antigen-APO-1 (Bernhard et al., 1989, Science 245:301-304), differentiation antigen (Feizi, 1985, Nature 314:53-57) such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, $D_{156-22}$ found in colorectal cancer, TRA-1-85 (blood group H), C14 found in colonic adenocarcinoma, F3 found in lung adenocarcinoma, AH6 found in gastric cancer, Y hapten, Le$^y$ found in embryonal carcinoma cells, TL5 (blood group A), EGF receptor found in A431 cells, E$_1$ series (blood group B) found in pancreatic cancer, FC10.2 found in embryonic carcinoma cells, gastric adenocarcinoma antigen, CO-514 (blood group Le$^a$) found in Adenocarcinoma, NS-10 found in adenocarcinomas, CO-43 (blood group Le$^b$), G49 found in EGF receptor of A431 cells, MH2 (blood group ALe$^b$/Le$^y$) found in colonic adenocarcinoma, 19.9 found in colon cancer, gastric cancer mucins, $T_{5A7}$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA-4 found in 4 to 8-cell stage embryos T cell receptor derived peptides from Cutaneous T cell Lymphoma (Edelson, 1998, The Cancer Journal 4:62), IL-1, IL-2, IL-3, IL-4, IL-5, IL-6, IL-7, IL-8, IL-9, IL-10, IL-11, IL-12, IFN-α, IFN-β, IFN-β 17 mutants, IFN-65, CD2, CD3, CD4, CD5, CD8, CD11a, CD11, CD11c, CD16, CD18, CD21, CD28, CD32, CD34, CD35, CD40, CD44, CD45, CD54, CD56, OX40L, 4-1BBL, K2, K1, Pβ, Oα, Mα, Mβ2, Mβ1, Hepsin, Pim-1, LMP1, TAP2, LMP7, TAP1, TRP, Oβ, IAβ, IAα, IEβ, IEβ2, IEα, CYP21, C4B, CYP21P, C4A, Bf, C2, HSP, Gla/b, TNF-α, TNF-β, D, L, Qa, T1a, COL11A2, DPβ2, DPα2, DPβ1, DPα1, DNα, DMα, DMβ, LMP2, TAP1, LMP7, DOβ, DQβ2, DQα2, DQβ3, DQβ1, DQα1, DRP, DRα, G250, HSP-70, HLA-B, HLA-C, HLA-X, HLA-E, HLA-J, HLA-A, HLA-H, HLA-G, HLA-F, nerve growth factor, somatotropin, somatomedins, parathormone, FSH, LH, EGF, TSH, THS-releasing factor, HGH, GRHR, PDGF, IGF-I, IGF-II, TGF-β, GM-CSF, M-CSF, G-CSF1, erythropoietin, β-HCG, 4-N-acetylgalactosaminyltransferase, GM2, GD2, GD3, JADE, BAGE, GAGE, XAGE, MUC-3, MUC-4, MUC-18, ICAM-1, C-CAM, V-CAM, ELAM, NM23, EGFR, E-cadherin, N-CAM, LFA-3 (CD58), EpCAM, B7.1, DCC, UTAA, melanoma antigen p75, K19, HKer 8, pMel 17, TP10, tyrosinase related proteins 1 and 2, p97, p53, RB, APC, DCC, NF-1, NF-2, WT-1, MEN-I, MEN-II, BRCA1, VHL, FCC and MCC, ras, myc, neu, raf, erb, src, fms, jun, trk, ret, gsp, hst, bcl and abl, HRF, MIRL, CR1, CR2, CR3, CR4, C3a/C4a receptor, C5a receptor, Epstein-Barr Virus antigens (EBNA), BZLF-1, BXLF-1, and Nuclear Matrix Proteins, modified TAAs or TSAs, splice variants of TAAs or TSAs, functional epitopes, epitope agonists, and degenerate nucleic acid variations thereof.

2. Viral Antigens

It should be possible to immunize against a wide spectrum of viruses such as

Influenza: influenza virus hemagglutinin (Genbank accession no. JO2132; Air, 1981, Proc. Natl. Acad. Sci. USA 78:7639-7643; Newton et al., 1983, Virology 128:495-501), influenza virus neuraminidase, PB1, PB2, PA, NP, $M_1$, $M_2$, $NS_1$, $NS_2$)), Adenovirus: E1A, E1B, E2, E3, E4, E5, L1, L2, L3, L4, L5

Pneumonovirinae (e.g., pneumovirus, human respiratory syncytial virus):

Papovaviridae (polyomavirus and papillomavirus): E1, E2, E3, E4, E5a, E5b, E6, E7, E8, L1, L2

Human respiratory syncytial virus: human respiratory syncytial virus: G glycoprotein (Genbank accession no. Z33429; Garcia et al., 1994, J. Virol.; Collins et al., 1984, Proc. Natl. Acad. Sci. USA 81:7683), RSV-viral proteins, e.g., RSV F glycoprotein, Dengue virus: core protein, matrix protein or other protein of Dengue virus (Genbank accession no. M19197; Hahn et al., 1988, Virology 162:167-180), Measles: measles virus hemagglutinin (Genbank accession no. M81899; Rota et al., 1992, Virology 188:135-142), Herpesviridae (e.g., herpes simplex virus 1, herpes simplex virus 2, herpes simplex virus 5, and herpes simplex virus 6: herpes simplex virus type 2 glycoprotein gB (Genbank accession no. M14923; Bzik et al., 1986, Virology 155:322-333), gB, gC, gD, and gE, HIV (GP-120, p17, GP-160, gag, pol, qp41, gp120, vif, tat, rev, nef, vpr, vpu, vpx antigens), ribonucleotide reductase, α-TIF, ICP4, ICP8, 1CP35, LAT-related proteins, gB, gC, gD, gE, gH, gI, gJ, and dD antigens, Lentivirus (e.g. human immunodeficiency virus 1 and human immunodeficiency virus 2): envelope glycoproteins of HIV I (Putney et al., 1986, Science 234:1392-1395)

Picornaviridae (e.g., enterovirus, rhinovirus, hepatovirus (e.g., human hepatitis A virus)

Cardiovirus

Apthovirus

Reoviridae (orthoreovirus, orbivirus, rotavirus, cypovirus, fijivirus, phytoreovirus, and oryzavirus), Retroviridae (mammalian type B retroviruses, mammalian type C retroviruses, avian type C retroviruses, type D retrovirus group, BLV-HTLV retroviruses)

spumavirus, flaviviridae (e.g., hepatitis C virus), hepadnaviridae (e.g., hepatitis B virus), togaviridae (e.g., alphavirus (e.g., sindbis virus) and rubivirus (e.g., rubella virus), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

Poliovirus: I VP1 (Emini et al., 1983, Nature 304:699),

Hepatitis B virus: hepatitis B surface antigen (Itoh et al., 1986, Nature 308:19; Neurath et al., 1986, Vaccine 4:34), hepatitis B virus core protein and/or hepatitis B virus surface antigen or a fragment or derivative thereof (see, e.g., U.K. Patent Publication No. GB 2034323A published Jun. 4, 1980; Ganem and Varmus, 1987, Ann. Rev. Biochem. 56:651-693; Tiollais et al., 1985, Nature 317:489-495), hepatitis (Hep B Surface Antigen ($gp27_S$, $gp36_S$, $gp42_S$, $p22^c$, po1, x)).

Ebola

Marburg

Rabies

Hanta virus infection

West Nile virus

SARS-like Coronaviruses

Varicella-zoster virus

Epstein-Barr virus

Alpha viruse

St. Louis encephalitis.

Adenovirdiae (mastadenovirus and aviadenovirus)

Leviviridae (levivirus, enterobacteria phase MS2, allolevirus)

Poxyiridae (e.g., chordopoxyirinae, parapoxvirus, avipoxvirus, capripoxvirus, leporipoxvirus, suipoxvirus, molluscipoxvirus, and entomopoxyirinae)

Papovaviridae (polyomavirus and papillomavirus)

Paramyxoviridae (paramyxovirus, parainfluenza virus 1)

Mobillivirus (measles virus)

Rubulavirus (mumps virus)

metapneumovirus (e.g., avian pneumovirus and human metapneumovirus

Pseudorabies: pseudorabies virus g50 (gpD), pseudorabies virus II (gpB), pseudorabies virus gI11 (gpC), pseudorabies virus glycoprotein H, pseudorabies virus glycoprotein E, Transmissible gastroenteritis: transmissible gastroenteritis glycoprotein 195, transmissible gastroenteritis matrix protein, Newcastle virus: Newcastle disease virus hemagglutinin-neuraminidase, infectious laryngotracheitis virus: infectious laryngotracheitis virus glycoprotein G or glycoprotein 1, La Crosse virus: a glycoprotein of La Crosse virus (Gonzales-Scarano et al., 1982, Virology 120:42), Swine viruses including:

swine rotavirus glycoprotein 38, swine parvovirus capsid protein, Serpulina hydrodysenteriae protective antigen, bovine viral diarrhea glycoprotein 55, neonatal calf diarrhea virus (Matsuno and Inouye, 1983, Infection and Immunity 39:155), hog cholera virus, African swine fever virus, swine influenza: swine flu hemagglutinin and swine flu neuraminidase.

Equine viruses including:

equine influenza virus or equine herpesvirus: equine influenza virus type A/Alaska 91 neuraminidase, equine influenza virus type A/Miami 63 neuraminidase, equine influenza virus type A/Kentucky 81 neuraminidase, equine herpesvirus type 1 glycoprotein B, and equine herpesvirus type 1 glycoprotein D, Venezuelan equine encephalomyelitis virus (Mathews and Roehrig, 1982, J. Immunol. 129:2763), Cattle viruses including:

bovine respiratory syncytial virus or bovine parainfluenza virus: bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and bovine parainfluenza virus type 3 hemagglutinin neuraminidase), bovine viral diarrhea virus glycoprotein 48 or glycoprotein 53, infectious bovine rhinotracheitis virus: infectious bovine rhinotracheitis virus glycoprotein E or glycoprotein G, foot and mouth disease virus, punta toro virus (Dalrymple et al., 1981, in Replication of Negative Strand Viruses, Bishop and Compans (eds.), Elsevier, N.Y., p. 167),

3. Bacterial Antigens

In some embodiments, the antigenic or immunogenic protein fragment or epitope may be derived from a pathogenic bacteria such as Anthrax,

*Chlamydia*: *Chlamydia* protease-like activity factor (CPAF), major outer membrane protein (MOMP)

*Mycobacteria*,

*Legioniella*: *Legionella* peptidoglycan-associated lipoprotein (PAL), mip, flagella, OmpS, hsp60, major secretory protein (MSP)

*Diptheria*: *diptheria* toxin (Audibert et al., 1981, Nature 289:543)

*Streptococcus* 24M epitope (Beachey, 1985, Adv. Exp. Med. Biol. 185:193)

Gonococcus: gonococcal pilin (Rothbard and Schoolnik, 1985, Adv. Exp. Med. Biol. 185:247), Mycoplasm: *mycoplasma hyopneumoniae*.

*Mycobacterium tuberculosis*: *M. tuberculosis* antigen 85A, 85B, MPT51, PPE44, mycobacterial 65-kDa heat shock protein (DNA-hsp65), 6-kDa early secretary antigenic target (ESAT-6)

*Salmonella typhi*

*Bacillus anthracis B. anthracis* protective antigen (PA)

*Yersinia perstis*: *Y. pestis* low calcium response protein V (LcrV), F1 and F1-V fusion protein

*Francisella tularensis*

*Rickettsia typhi*

*Treponema pallidum*.

*Salmonella*: SpaO and H1a, outer membrane proteins (OMPs);

*Pseudomonas*: *P.aeruginosa* OMPs, PcrV, OprF, OprI, PilA and mutated ToxA

4. Fungal Antigens

In some embodiments, the antigenic or immunogenic protein fragment or epitope may be derived from a pathogenic fungus, including but not limited to:

*Coccidioides immitis*: *Coccidioides* Ag2/Pra106, Prp2, phospholipase (P1b), alpha-mannosidase (Amn1), aspartyl protease, Gel1

*Blastomyces dermatitidis*: *Blastomyces dermatitidis* surface adhesin WI-1

*Cryptococcus neoformans*: *Cryptococcus neoformans* GXM and its Peptide mimotopes, and mannoproteins, Cryptosporidiums surface proteins gp15 and gp40, Cp23 antigen, p23

*Candida albicans*,

*Aspergillus* species: *Aspergillus* Asp f 16, Asp f 2, Der p 1, and Fel d 1, rodlet A, PEP2, *Aspergillus* HSP90, 90-kDa catalase

5. Protozoan Antigens

In some embodiments, the antigenic or immunogenic protein fragment or epitope may be derived from a pathogenic protozoan, such as, for example:

*Plasmodium falciparum, Plasmodium vivax, Plasmodium ovale, Plasmodium malariae, Plasmodium* apical membrane antigen 1 (AMA1), 25-kDa sexual-stage protein (Pfs25), erythrocyte membrane protein 1 (PfEMP1) circumsporozoite protein (CSP), Merozoite Surface Protein-1 (MSP 1)

*Leishmania* species: *Leishmania* cysteine proteinase type III (CPC)

*Trypanosome* species (African and American): *T. pallidum* outer membrane lipoproteins, *Trypanosome* beta-tubulin (STIB 806), microtubule-associate protein (MAP p15), cysteine proteases (CPs)

cryptosporidiums,

*isospora* species,

*Naegleria fowleri,*

*Acanthamoeba* species,

*Balamuthia mandrillaris,*

*Toxoplasma gondii*, or

*Pneumocystis carinii*: *Pneumocystis carinii* major surface glycoprotein (MSG), p55 antigen

*Babesia*

Schistosomiasis: *Schistosomiasis mansoni* Sm14, 21.7 and SmFim antigen, Tegument Protein Sm29, 26 kDa GST, *Schistosoma japonicum*, SjCTPI, SjC23, Sj22.7, or SjGST-32

Toxoplasmosis: gondii surface antigen 1 (TgSAG1), protease inhibitor-1 (TgPI-1), surface-associated proteins MIC2, MIC3, ROP2, GRA1-GRA7.

3. Immunostimulatory Molecules

In certain embodiments the recombinant viruses express antigens to elicit an immune response in a subject as well as cytokines or co-stimulatory molecules. Alternatively or in combination, such as interleukin (IL) (e.g., IL-2, IL-4, IL-10, IL-12), an interferon (IFN) (e.g., IFN-γ), granulocyte macrophage colony stimulating factor (GM-CSF) or an accessory molecule (e.g. ICAM-1) or co-stimulatory molecules, e.g., B7.1, B7.2, may be used as adjuvants.

In certain embodiments, either cytokines, co-stimulatory or other immunomodulatory molecules can be co-administered via co-insertion of the genes encoding the molecules into the recombinant vector or a second recombinant virus which is admixed with the recombinant virus expressing the antigen. Alternatively, the cytokines can be administered separately, systemically to the host. It may be desirable to administer a substantially pure preparation of the immunomodulator to boost vaccine efficacy.

Examples of costimulatory molecules include, but are not limited to, B7-1, B7-2, ICAM-1, CD40, CD40L, LFA-3, CD72, OX40L (with or without OX40). Examples of cytokines and growth factors include but are not limited to: granulocyte macrophage-colony stimulating factor (GM-CSF), granulocyte-colony stimulating factor (G-CSF), macrophage-colony stimulating factor (M-CSF), tumor necrosis factors (TNFα and TNFβ), transforming growth factors (TGFα and TGFβ), insulin-like growth factors (IGF-I and IGF-II), growth hormone, interleukins 1 to 15 (IL-1 to IL-15), interferons α, β, γ (IFN-α IFN-β and IFN-γ), brain-derived neurotrophic factor, neurotrophins 3 and 4, hepatocyte growth factor, erythropoictin, EGF-like mitogens, TGF-like growth factors, PDGF-like growth factors, melanocyte growth factor, mammary-derived growth factor 1, prostate growth factors, cartilage-derived growth factor, chondrocyte growth factor, bone-derived growth factor, osteosarcoma-derived growth factor, glial growth-promoting factor, colostrum basic growth factor, endothelial cell growth factor, tumor angiogenesis factor, hematopoietic stem cell growth factor, B-cell stimulating factor 2, B-cell differentiation factor, leukemia-derived growth factor, myelomonocytic growth factor, macrophage-derived growth factor, macrophage-activating factor, erythroid-potentiating activity, keratinocyte growth factor, ciliary neurotrophic growth factor, Schwann cell-derived growth factor, vaccinia virus growth factor, bombyxin, neu differentiation factor, v-Sis, glial growth factor/acetylcholine receptor-inducing activity, transferrin, bombesin and bombesin-like peptides, angiotensin II, endothelin, atrial natriuretic factor (ANF) and ANF-like peptides, vasoactive intestinal peptide, RANTES, Bradykinin and related growth factors.

In some of the preferred embodiments, the co-stimulatory molecule, growth factor, adjuvant or cytokine is IL-1, IL-2, IL-4, IL-7, IL1-9, IL-12, IL-15, IL-18, IL-23, IL-27, IL-31, IL-33, B7-1, B7-2, B7-H3, LFA-3, B7-H3, CD40, CD40L, ICOS-ligand, OX-40L, 4-1BBL, GM-CSF, SCF, FGF, Flt3- ligand, CCR4, QS-7, QS-17, QS-21, CpG oligonucleotides, ST-246, AS-04, LT R192G mutant, Montanide ISA 720, heat shock proteins, synthetic mycobacterial cordfactor (CAF01), Lipid A mimetics, *Salmonella enterica serovar Typhimurium flagellin* (FliC), Montanide 720, Levamisole (LMS), Imiquimod, Diphtheria Toxin, IMP321, AS02A, AS01B, AS15-SB, Alhydrogel, Montanide ISA, Aluminum hydroxide, MF59, ISCOMATRIX, MLPA, MPL and other TLR-4 ligands, MDP and other TLR-2 ligands, CpG and TLR9 ligands, imiquimod and other TLR7 ligands, resiquimod and TLR8 ligands, AS02A, AS01B, Heat Liable Toxin LTK63 and LT-R192G. In some embodiments, poxviruses expressing B7-1, ICAM-1, and LFA-3, also known as TRICOM, are provided that induce activation of both $CD4^+$ and $CD8^+$ T cells. (U.S. Pat. No. 6,045,802; Hodge et al., J. Natl. Cancer Inst. 92: 1228-39 (2000); Hodge et al., Cancer Research 59: 5800-07 (1999)). OX40 is a primary co-stimulator of T cells that have encountered antigen, rather than naïve T cells, and promotes T-cell expansion after T cell tolerance is induced. (Bansal-Pakal et al., Nature Med. 7: 907-12 (2001)). OX40L plays a role during T cell activation by a) sustaining the long-term proliferation of $CD4^+$ and $CD8^+$ T cells, b) enhancing the production of Th1 cytokines such as IL-2, IGN-γ, and TNF-α from both $CD4^+$ and $CD8^+$ T cells without changing IL-4 expression, c) protecting T cells from apoptosis. In certain embodiments, the combination of B7-1, ICAM-1, LFA-3, and OX40L enhances initial activation and then further potentiates sustained activation of naïve and effector T cells.

Adjuvants can also be administered. In one embodiment, one administers a poxvirus vector containing B7, LFA-3 and ICAM-1 in conjunction with a tumor associated antigen. In a further embodiment, the poxvirus also contains OX40L. Other useful adjuvants that can be administered separately from the poxvirus are, for example, RIBI Detox (Ribi Immunochemical), QS21 (Aquila), incomplete Freund's adjuvant.

In some embodiments, the recombinant viruses are administered in the form of a composition including one or more other pharmaceutically acceptable carriers, including any suitable diluent or excipient. Preferably, the pharmaceutically acceptable carrier does not itself induce a physiological response, e.g., an immune response nor result in any adverse or undesired side effects and/or does not result in undue toxicity. Pharmaceutically acceptable carriers include, but are not limited to, saline, buffered saline, dextrose, water, glycerol, sterile isotonic aqueous buffer, and combinations thereof. Additional examples of pharmaceutically acceptable carriers, diluents, and excipients are provided in Remington's Pharmaceutical Sciences (Mack Pub. Co., N.J., current edition.

III. METHODS OF MAKING VACCINES

In general, the DNA donor vector contains the following elements: (i) a prokaryotic origin of replication, so that the vector may be amplified in a prokaryotic host; (ii) a gene encoding a marker which allows selection of prokaryotic host cells that contain the vector (e.g., a gene encoding antibiotic resistance); (iii) at least one gene encoding a desired protein located adjacent to a transcriptional promoter capable of directing the expression of the gene; and (iv) DNA sequences homologous to the region of the parent virus genome where the foreign gene(s) will be inserted, flanking the construct of element (iii).

A. Engineering of the Viral Vectors to Express Antigens

Genes encoding an antigen of interest can be amplified by cloning the gene into a bacterial host. For this purpose, various prokaryotic cloning vectors can be used. Examples are plasmids pBR322 and pEMBL. In general, the cloned genes can be excised from the prokaryotic cloning vector by restriction enzyme digestion. The DNA fragment carrying the cloned gene can be modified as needed, for example, to make the ends of the fragment compatible with the insertion sites of the poxvirus vectors, then purified prior to insertion into these vectors at restriction endonuclease cleavage sites (cloning sites). The basic techniques of inserting genes into viruses are known to the skilled artisan and involve, for example, recombination between the viral DNA sequences flanking a gene in a donor plasmid and homologous sequences present in the parental virus (Mackett, et al., Proc. Natl. Acad. Sci. USA 79:7415-7419 (1982)).

For example, the DNA gene sequence to be inserted into the virus can be placed into a plasmid, e.g., an *E. coli* plasmid construct, into which DNA homologous to a section of DNA such as that of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA which is the desired insertion region. The resulting plasmid construct is then amplified by growth within *E. coli* bacteria and isolated. Preferably, the plasmid also contains an origin of replication such as the *E. coli* origin of replication, and a marker such as an antibiotic resistance gene for selection and propagation in *E. coli*. The isolated plasmid containing the DNA gene sequence to be inserted is transfected into a cell culture, e.g., chick embryo fibroblasts, along with the poxvirus. Recombination between homologous pox DNA in the plasmid and the viral genome respectively results in a poxvirus modified by the presence of the promoter-gene construct in its genome, at a site which does not affect virus viability.

In some embodiments, the gene(s) IS inserted into a site or region (insertion region) in the virus which does not significantly affect viability of the resultant recombinant virus, e.g. intragenic regions between viral genes, preferably non-essential viral genes. The skilled artisan can readily identify such regions in a virus by, for example, testing segments of virus DNA for regions that allow recombinant formation without seriously affecting virus viability of the recombinant. One region that can readily be used and is present in many viruses, for example, is the thymidine kinase gene that has been found in all poxvirus genomes examined (leporipoxvirus: Upton, et al., J. Virology, 60:920 (1986) (shope fibroma virus); capripoxvirus: Gershon, et al., J. Gen. Virol., 70:525 (1989) (Kenya sheep-1); orthopoxvirus: Weir, et al., J. Virol., 46:530 (1983) (vaccinia); Esposito, et al., Virology, 135:561 (1984) (monkeypox and variola virus); Hruby, et al., PNAS, 80:3411 (1983) (vaccinia); Kilpatrick, et al., Virology, 143:399 (1985) (Yaba monkey tumor virus); avipoxvirus: Binns, et al., J. Gen. Virol. 69:1275 (1988) (fowlpox); Boyle et al., Virology, 156: 355 (1987) (fowlpox); Schnitzlein, et al., J. Virological Methods, 20:341 (1988) (fowlpox, quailpox); entomopox (Lytvyn, et al., J. Gen. Virol. 73:3235-3240 (1992)). In fowlpox, in addition to the TK region, other insertion regions include, for example, BamHI J (Jenkins, et al., AIDS Research and Human-Retroviruses 7:991-998 (1991)) the EcoRI-HindIII fragment, BamHI fragment, EcoRV-HindIII fragment, BamHI fragment and the HindIII fragment set forth in EPO Application No. 0 308 220 A1. (Calvert, et al., J. of Virol. 67:3069-3076 (1993); Taylor, et al., Vaccine 6:497-503 (1988); Spehner, et al., (1990) and Boursnell, et al., J. of Gen. Virol. 71:621-628 (1990)).

Methods for constructing donor plasmids for the introduction of multiple foreign genes into poxvirus are described, for example, in WO91/19803, the techniques of which are incorporated herein by reference. In general, all DNA fragments for construction of the donor vector, including fragments containing transcriptional promoters and fragments containing sequences homologous to the region of the parent virus genome into which foreign genes are to be inserted, can be obtained from genomic DNA or cloned DNA fragments. The donor plasmids can be mono-, di-, or multivalent (i.e., can contain one or more inserted foreign gene sequences).

The donor vector may contain an additional gene which encodes a marker which will allow identification of recombinant viruses containing inserted foreign DNA. Several types of marker genes can be used to permit the identification and isolation of recombinant viruses. These include, for example, genes that encode antibiotic or chemical resistance (e.g., see Spyropoulos et al., J. Virol., 62:1046 (1988); Falkner and Moss., J. Virol., 62:1849 (1988); Franke et al., Mol. Cell. Biol., 5:1918 (1985), as well as genes such as the *E. coli* lacZ gene, that permit identification of recombinant viral plaques by colorimetric assay (Panicali et al., Gene, 47:193 199 (1986)).

Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a poxvirus are chick embryo dermal (CED) cells, HuTK143 (human) cells, and CV-1 and BSC-40 (both monkey kidney) cells. Infection of cells with poxvirus and transfection of these cells with plasmid vectors is accomplished by techniques standard in the art (Panicali and Paoletti, U.S. Pat. No. 4,603,112, WO89/03429). Alternatively, the donor DNA can be directly ligated into the parental virus genome at a unique restriction site (Scheiflinger, et al. (1992) Proc. Natl. Acad. Sci. (USA) 89:9977 9981).

Following in vivo recombination or ligation, recombinant viral progeny can be identified by several techniques well known in the art. For example, if the DNA donor vector is designed to insert foreign genes into the parent virus thymidine kinase (TK) gene, viruses containing integrated DNA will be TK⁻ and can be selected on this basis (Mackett et al., Proc. Natl. Acad. Sci. USA, 79:7415 (1982)). Alternatively, co-integration of a gene encoding a marker or indicator gene with the foreign gene(s) of interest, as described above, can be used to identify recombinant progeny. One preferred indicator gene is the *E. coli* lacZ gene: recombinant viruses expressing β-galactosidase can be selected using a chromogenic substrate for the enzyme (Panicali et al., Gene, 47:193 (1986)).

B. Culturing of Viral Vector in Host Cells

Most viral vaccines such as attenuated or recombinant viruses are manufactured from cell culture systems. The cells used for virus/vaccine production may be cell lines, i.e. cells that grow continuously in vitro, either as single-cell suspension culture in bioreactors or as a monolayer on a cell-support surface of tissue culture flasks or roller-bottles. Primary animal cells may be used for the manufacture of vaccines. For example, chordopoxyirinae, in particular MVA are amplified in cell cultures of primary or secondary chicken embryo fibroblasts (CEF). The cells are obtained from embryos of chicken eggs that are incubated for 10 to 12 days. The cells of the embryos are then dissociated and purified. These primary CEF cells can either be used directly or after one further cell passage as secondary CEF cells. Subsequently, the primary or secondary CEF cells are infected with the MVA. For the amplification of MVA the infected cells are incubated for 2-3 days at 37° C. (see, e.g., Meyer, H. et al. 1991; J. of General Virology 72, 1031-1038; Sutter et al. 1994, Vaccine, Vol. 12, No. 11, 1032-1040). CEF cells are often used since many virus vaccines are made by attenuating the virulent disease-causing virus by serially passaging in CEF cells. Attenuated viruses, such as MVA are preferably not propagated on human cells since there is a concern that the viruses might become replication competent in cells of human origin. Viruses that have regained the ability to replicate in human cells represent a health risk if administered to humans, in particular if the individuals are immune compromised. For this reason, some attenuated viruses, such as MVA, are strictly manufactured from CEF cells, if intended for human use. Moreover, CEF cells are used for those viruses that grow only in these cells, for example avian viruses such as avipox viruses, canary pox virus, ALVAC, Fowl pox virus and NYVAC.

In certain embodiments, host cells, such as epidermal epithelial cells, fibroblasts, or dendritic cells, infected with the recombinant viruses express the antigen(s) and may additionally express the immunostimulatory molecule(s). In these embodiments, the antigen may be expressed at the cell surface of the infected host cell. The immunostimulatory molecule may be expressed at the cell surface or may be actively secreted by the host cell.

The expression of both the antigen and the immunostimulatory molecule may provide the necessary MHC restricted peptide to specific immunosurveilling T cells and the appropriate signal to the T cell in the skin to aid in antigen recognition and proliferation or clonal expansion of antigen specific T cells. The overall result may be an upregulation of the immune system. In certain embodiments the upregulation of the immune response is an increase in antigen specific T-helper lymphocytes and/or cytotoxic lymphocytes, including for example, Th1 or Th2 CD4⁺ T-helper cell-mediated or CD8⁺ cytotoxic T-lymphocytes, which are able to kill or inhibit the growth of a disease causing agent (such as a cancer cell) or a cell infected with a disease causing agent (such as a cell infected with a virus, a bacteria, a fungus, or a protozoa. In certain embodiments, the immune stimulation may also involve an antibody response comprising generations of one or more antibody classes, such as IgM, IgG, and/or IgA.

Once a recombinant virus has been identified, a variety of methods well known in the art can be used to assay the expression of the polypeptide encoded by the inserted gene. These methods include, for example, black plaque assay (an in situ enzyme immunoassay performed on viral plaques), Western blot analysis, radioimmunoprecipitation (RIPA), enzyme immunoassay (EIA), or functional assay such as CTL assay.

IV. METHODS OF TREATMENT

A. Individuals to be Vaccinated

A subject in need of treatment is a subject having or at risk of having cancer or a subject having or at risk of having an infection (e.g., a subject having or at risk of contracting a viral, bacterial, fungal or protozoal infection).

A subject having cancer is a subject that has detectable cancerous cells. "Cancer" as used herein refers to an uncontrolled growth of cells which interferes with the normal functioning of the bodily organs and systems. A subject at risk of developing a cancer is one who has a higher than normal probability of developing cancer. These subjects include, for instance, subjects having a genetic abnormality, the presence of which has been demonstrated to have a correlative relation to a higher likelihood of developing a cancer. These subjects also include subjects exposed to cancer causing agents (i.e., carcinogens) such as tobacco, asbestos, or other chemical toxins, or subjects who have previously been treated for cancer and are in apparent remission.

A subject having an infection is a subject that has been exposed to an infectious microorganism and has acute or chronic detectable levels of the microorganism in his/her body or has signs and symptoms of the infectious microorganism. Methods of assessing and detecting infections in a subject are known by those of ordinary skill in the art. A subject at risk of having an infection is a subject that may be expected to come in contact with an infectious microorganism. Examples of such subjects are medical workers or those traveling to parts of the world where the incidence of infection is high. In some embodiments, the subject is at an elevated risk of an infection because the subject has one or more risk factors to have an infection. Examples of risk factors to have an infection include, for example, immunosuppression, immunocompromise, age, trauma, burns (e.g., thermal burns), surgery, foreign bodies, cancer, newborns especially newborns born prematurely. The degree of risk of an infection depends on the multitude and the severity or the magnitude of the risk factors that the subject has. Risk charts and prediction algorithms are available for assessing the risk of an infection in a subject based on the presence and severity of risk factors. Other methods of assessing the risk of an infection in a subject are known by those of ordinary skill in the art. In some embodiments, the subject who is at an elevated risk of an infection may be an apparently healthy subject. An apparently healthy subject is a subject who has no signs or symptoms of disease.

Examples of viruses that can be treated by the methods described herein, or for which the methods described herein confer protection, include, but are not limited to, HIV, influenza, dengue, Hepatitis A virus, Hepatitis B virus, Hepatitis C virus, Human papilloma virus, Ebola, Marburg, Rabies, Hanta virus infection, West Nile virus, SARS-like Coronaviruses, Herpes simplex virus (HSV1 and HSV2), Varicella-zoster virus, Epstein-Barr virus, Human herpesvirus 8, Alpha viruses, St. Louis encephalitis.

Other viruses that may be treated or for which the methods described herein confer protection include, but are not limited to: enteroviruses (including, but not limited to, viruses that the family picornaviridae, such as polio virus, Coxsackie virus, echo virus), rotaviruses, adenovirus, and hepatitis virus, such as hepatitis A, B, C D and E. Specific examples of viruses that have been found in humans include, but are not limited to, Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., bunya viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); cytomegalovirus (CMV); Poxyiridae (variola viruses, vaccinia viruses, pox viruses); Iridoviridae (e.g., African swine fever virus); and other viruses acute laryngotracheobronchitis virus, Alphavirus, Kaposi's sarcoma-associated herpesvirus, Newcastle disease virus, Nipah virus, Norwalk virus, Papillomavirus, parainfluenza virus, and avian influenza.

Bacterial infections or diseases that can be treated or prevented are caused by bacteria including, but not limited to, *Mycobacterium tuberculosis, Salmonella typhi, Bacillus anthracis, Yersinia perstis, Francisella tularensis, Legionella, Chlamydia, Rickettsia typhi,* and *Treponema pallidum*. Other bacteria that may be treated or for which the methods described herein confer protection include, but are not limited to, *Pasteurella* species, *Staphylococci* species, and *Streptococcus* species. Gram negative bacteria include, but are not limited to, *Escherichia coli, Pseudomonas* species, and *Salmonella* species. Specific examples of infectious bacteria include, but are not limited to, *Helicobacter pyloris, Borelia burgdorferi, Mycobacteria* sps (e.g. *M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae,* pathogenic *Campylobacter* sp., *Enterococcus* sp., *Haemophilus influenzae, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pertenue, Leptospira,* and *Actinomyces israelli*.

Fungal diseases that can be treated or prevented using the poxviruses and methods described herein include, but are not limited to, *Coccidioides immitis, Blastomyces dermatitidis, Cryptococcus neoformans, Candida albicans, Aspergillus* species. Other fungi that may be treated or for which the methods described herein confer protection include, but are not limited to: *Histoplasma capsulatum, Coccidioides immitis,* and *Chlamydia trachomatis*.

Protozoal diseases or infections that can be treated or prevented unclude but are not limited to, Malaria (*Plasmodium falciparum, Plasmodium vivax, Plasmodium ovale, Plasmodium malariae), Leishmania* species, *Trypanosome* species (African and American), *cryptosporidiums, isospora* species, *Naegleria fowleri, Acanthamoeba* species, *Balamuthia mandrillaris, Toxoplasma gondii,* and *Pneumocystis carinii*.

Cancers or tumors which may be treated or prevented, but are not limited to, melanoma, cutaneous squamous cell carcinoma, basal cell carcinoma, breast cancer, prostate adenocarcinoma, prostatic intraepithelial neoplasia, squamous cell lung carcinoma, lung adenocarcinoma, small cell lung carcinoma, ovary cancer of epithelial origin, colorectal adenocarcinoma and leiomyosarcoma, stomach adenocarcinoma and leiomyosarcoma, hepatocellular carcinoma, cholangiocarcinoma, ductal adenocarcinomas of pancreas, endocrine pancreatic tumors, renal cell carcinoma, transitional cell carcinoma of kidney and bladder, bladder squamous cell carcinoma, papillary thyroid cancer, follicular thyroid cancer, brain cancers (astrocytoma, glioblastoma multiforme).

B. Routes of Administration

Modified, replication-deficient or non-replicating viral vectors expressing one or more exogenous T-cell antigens in an amount sufficient to elicit or stimulate the immune response against the antigen are administered to mechanically disrupted epidermal tissue of the subject.

Intranasal vaccine will generate a robust population of lung $T_{RM}$, but relatively few skin, liver, or GI tract $T_{RM}$. Intraperitoneal administration does not generate large populations of skin or lung $T_{RM}$. Intramuscular administration is ineffective at generating $T_{RM}$ in most tissues.

Human beings can live for 70 years or more, spending much of that time free of infectious diseases. The adaptive immune system, through the generation and maintenance of protective immunologic memory, permits people to live amongst a plethora of pathogens for many decades. The body has several epithelial surfaces that interface with the environment. The most accessible is skin, but continuous with skin is the oropharyngeal mucosal epithelium, the female reproductive epithelium, and the large and complex epithelial tissues that line the respiratory and gastrointestinal tracts. For pathogens to gain access to blood and internal tissues, they must infect and then breach one or more of these epithelial barriers. While each of these epithelial tissues is structurally different and employs different innate immune defenses, the adaptive immune system mediates lifelong protection against pathogen attack, through T cell memory and B cell antibody production.

As recently as five years ago, it was an article of faith that protective T cell memory was mediated by cells circulating in blood and through secondary lymphoid tissues. According to this view, while memory T cells could be readily mobilized from these compartments to peripheral epithelial tissues to captain the immunologic defense forces fighting infection, T cells were thought to return to blood and lymph nodes once the infection was resolved. Very recently, memory T cells have been found in peripheral tissues, in abundance, in both humans and mice. Because of its accessibility, the majority of human work has been done in skin. Seminal work in this area has demonstrated that twice as many T cells reside in normal, non-inflamed human skin as in blood, and there are more than 20-fold more of skin homing memory T cells in normal skin than in blood. These skin resident T cells ($T_{RM}$) have a diverse T cell receptor repertoire, can be readily activated through the TCR or by cytokines, and have great proliferative potential. Moreover, they are polyfunctional with regard to cytokine production, suggesting their authentic role as memory T cells that protect against infection. Similar populations of $T_{RM}$ exist in lung and GI tract, as well as reproductive mucosa. T cells are recruited to skin and other epithelial tissues after pathogen challenge, and then can persist there long term. At least two separate studies examining viral infection of skin have demonstrated that these $T_{RM}$, rather than antibody or $T_{CM}$ recruited from blood, provide principal protection against viral challenge, even many months after the initial infection (Liu et al. Nature Medicine. 2010 February; 16(2): 224-7. Epub 2010 Jan. 17). Similar populations of T cells have been identified in lung (Connor et al. Eur J. Immunol. 2010 September; 40(9):2482-92) and GI tract (Masopust et al. J Exp Med. 2010 Mar. 15; 207(3):553-64. Epub 2010 Feb. 15) after infection. These resident $T_{EM}/T_{RM}$ consist largely of T cells that were originally (as naïve T cells) activated in lymph nodes draining that tissue (Liu et al Immunity. 2006; 25(3):511-20), and thus represent a resident army of tissue specific T cells specific for tissue selective pathogens.

T cell recruitment into extranodal peripheral tissues is a highly regulated process controlled by the sequential interactions of adhesion molecules and chemokine receptors that are differentially expressed on various T cell subsets and their target. Human skin-homing T cells express cutaneous lymphocyte antigen (CLA) which binds to skin microvasculature-expressed E-selectin, typically in combination with CCR4 whose ligand CCL17 (TARC) is constitutively expressed on skin endothelium. Gut-homing T cells express $\alpha 4\beta 7$ integrin and chemokine receptor CCR9, to which the corresponding ligands MadCAM-1 and CCL25 (TECK) are expressed on the endothelium and epithelium of the small intestine Following VACV skin scarification, the skin homing molecules E- and P-selectin ligands (E-lig and P-lig, the functional murine equivalents of human CLA) are strongly upregulated on antigen-specific CD8 T cells between the $3^{rd}$ and $10^{th}$ cell divisions in the regional LN draining the scarified site. Subsets of proliferating VV specific CD8 T cells leave the draining inguinal node after as few as three cell divisions and migrate through blood to skin ($T_{EM}$), or to other LN ($T_{CM}$), respectively. In these distant LN, vaccinia-specific $T_{CM}$ cells continue to proliferate, in the absence of continued antigen receptor stimulation, and acquire homing receptors consistent with the regional drainage of the LN they have migrated to; e.g., $\alpha 4\beta 7$-integrin in mesenteric LN. Thus, generalized CD8 T cell mediated immunity to a local challenge is acquired by systemic dissemination of activated T cells from the local draining LN. The tissue homing properties of these cells then are imprinted in the respective LN environments to which they disseminate.

Modes of vaccine delivery play a critical role in the generation of $T_{RM}$. Different modes of vaccine delivery can generate similar levels of antibody and $T_{CM}$, but vastly different levels of $T_{RM}$. The presence or absence of $T_{RM}$ is reflected in resistance to infection, and demonstrates clearly that simply sampling blood for antibody titers and/or memory T cell abundance and function as a surrogate for protective immunity falls far short of this goal and may even be misleading. Skin scarification with VACV is far and away the most effective way of generating both optimal $T_{RM}$ populations as well as $T_{CM}$, not only in skin, but also in distant epithelial tissues. Mmimicking infection through an epithelial tissue is essential to generating the robust protective immunity that the vertebrate immune system has, over millions of years, evolved to generate. Skin scarification replicates how pathogens breach the barrier of skin to infect it. From this perspective, it seems particularly irrational to vaccinate through skeletal muscle. While epithelial tissues are rich in dendritic cells and stromal cells that modify immune response, and lymph nodes draining these tissues have been shown to be elite "training academies" for T cells, muscle is not physiologically exposed to pathogens (or danger signals), does not contain abundant dendritic cells, and is drained by deeper LN that are unable to instruct T cells to traffic to peripheral tissues. While a tried and true means of generating neutralizing antibody responses, intramuscular vaccination is a woefully ineffective means of generating $T_{RM}$.

Significant populations of $T_{RM}$ can be readily demonstrated in human skin. Normal skin of healthy adults contains approximately 20 billion memory T cells, nearly twice the number of T cells that are present in the entire circulation. Moreover, when the relevant skin homing T cell subset was considered, nearly 98% of $T_{EM}$ with a skin homing phenotype were found in skin rather than blood under normal, non-inflamed conditions. These skin homing/resident T cells are all CD45RO$^+$ memory cells, predominantly $\alpha\beta$ TCR$^+$, CLA$^+$ CCR4$^+$, and express significant levels of CCR6, somewhat less CCR8 and CXCR6, and a subset of about 15-20% express both CD62L and CCR7. Thus, skin $T_{RM}$ are 80% $T_{EM}$ and 20% $T_{CM}$. They contain significant numbers of TNF$\alpha$ and IL-17 producing T cells, as well as T cells that produce IFN-$\gamma$; relatively few cells that produce IL-4 are present. TCR V$\beta$ antibody FACS analysis indicates that these $T_{RM}$ are highly diverse, and all V$\beta$ families are represented. Nearly half of these $T_{RM}$ expressed the activation markers CD25 (at intermediate levels) and CD69. $T_{RM}$ are also much more responsive to stimulation than cells from the blood.

An analogous population of $T_{RM}$ resides in human lung. These tissue resident cells are also exclusively CD45RO$^+$, and do not bear either skin (CLA/CCR4 co expression) or gut ($\alpha 4\beta 7$ integrin) homing markers, but express integrin $\alpha 4\beta 7$. Their expression of CD69 (>50% positive) indicates that they are true tissue resident cells, and not simply cells that are trapped in the pulmonary vasculature (peripheral blood T cells are uniformly negative for CD69, while $T_{RM}$ in humans and mice express significant CD69)). Based on similar cell counting methodologies as used in skin, it has been calculated that there are roughly 10 billion $T_{RM}$ in lung, half as many as the total number of $T_{RM}$ in skin. Large resident T cell populations are also found in human large and small bowel.

Repetitive encounter with antigen through a peripheral tissue generates increasing numbers of $T_{RM}$ that accumulate in peripheral tissues over months, years, and decades in humans. The distribution of $T_{RM}$ after immunization can be modified by administering mediators that have been shown to alter the expression of T cell homing markers. For example, retinoic acid has been shown to enhance the expression of gut homing markers, while reducing skin homing markers.

Antigens from a pathogen encountered through infected skin are presented by skin-derived dendritic cells in lymph nodes draining skin, and activate naïve T cells to proliferate and force their differentiation into skin homing T cells as well as central memory T cells. These skin homing T cells rapidly traffic to skin, seeding both infected skin and normal skin. A subset of these T cells then takes up residence in skin for years to decades. This occurs repeatedly throughout childhood, adolescence, and adulthood. For antigens encountered multiple times over the years, an amplified population of central memory T cells can be activated in lymph node, and these in turn can differentiate into skin homing T cells and seed skin in even greater numbers. One expects that the skin contains polyfunctional CD45RO+/CLA+/CCR4+$T_{RM}$ enriched for common skin pathogens, such as *C. albicans, S. aureus, Trichophyton* species, *P. acnes, P. ovale*, HSV, as well as VACV and Yellow Fever (in vaccinated individuals), but not for common gut or lung pathogens. The frequency of $T_{RM}$ responsive to these microorganisms will vary from individual to individual, but should be significantly higher than the frequency of responsive $T_{CM}$ in peripheral blood, and even higher than the frequency of responsive naïve T cells.

The lung should contain polyfunctional CD45RO+/VLA-1+$T_{RM}$ enriched for common lung pathogens, for example, Influenza virus, M pneumonia, S. pneumonia, Adenovirus species, Rhinovirus species The gastrointestinal tract should contain polyfunctional CD45RO/$\alpha 4\beta 7$+$T_{RM}$ enriched for those specific for rotavirus, norovirus, *E. coli*, enteroviruses, *H. pylori*, calciviruses.

In contrast, the blood contains $T_{CM}$ and $T_{EM}$ specific for all antigens found in skin, lung, and colon, as well as endogenous viruses such as CMV and EBV. Most antigen reactive T cells will be non-polyfunctional TCM To maximize immune responses using the route of administration described herein, i.e., mechanical disruption of the epithelial tissue at the time of exposure to replication deficient virus expressing one or more exogenous antigen, vaccines to infectious diseases would have to be evaluated not based solely on their ability to generate a neutralizing antibody response, but rather their capacity to generate populations of antigen specific $T_{EM}$ and $T_{CM}$ that would migrate to relevant tissues and become $T_{RM}$.

Vaccines to prevent the emergence or recurrence of human cancers would have to be similarly be modified so as to generate optimal populations of $T_{RM}$ that would be deployed to the relevant tissue. For example, the HPV vaccine for cervical cancer might be modified to deliver $T_{RM}$ to reproductive mucosa.

Immunologically mediated diseases that involve peripheral tissues, including skin (e.g., psoriasis), lung (e.g. asthma), and gut (e.g., inflammatory bowel disease) would have to be studied to fully establish the role of $T_{RM}$ in these processes. The implication of $T_{RM}$ playing a major role in disease activity, or the tendency for these diseases to chronically recur, would lead to treatment strategies that might be very different from those currently employed.

C. Administration of Viral Vectors to the Epidermal Tissue

Modified poxviruses are preferably administered by mechanical disruption of the epidermis (e.g., by skin scarification, scratching, abrading or superficial cutting). Methods and devices for disrupting the skin and for depositing a substance into the epidermis of the skin are known in the art. Examples of devices for disrupting the skin include a scarification needle, a hypodermic needle, or an abrader. In one embodiment, the device is incorporated as part of a sterile vial containing lyophilized vaccine, which is rehydrated either from a separate source of diluent or by perforating a membrane separating the vaccine from the diluent.

The device mechanically disrupts the epidermis (e.g., abrader) by moving or rubbing over the epidermal tissue such as the skin. Alternatively, a chemical abrader is used, such as a surfactant to disrupt the mucosal layer in the lung, gastrointestinal tract or reproductive tract. It is preferred that the minimum amount of abrasion/mechanical disruption to produce the desired result be used. Determination of the appropriate amount of abrasion/mechanical disruption for a selected poxvirus and/or composition thereof is within the ordinary skill in the art. In another embodiment the viral vaccine may be applied in dry form to the abrading surface of the abrading device prior to application. In this embodiment, a reconstituting liquid is applied to the skin at the delivery site and the viral vaccine-coated abrading device is applied to the skin at the site of the reconstituting liquid. It is then moved or rubbed over the skin so that the poxvirus (composition) becomes dissolved in the reconstituting liquid on the surface of the skin and is delivered simultaneously with abrasion. Alternatively, a reconstituting liquid may be contained in the device (e.g., a scarification needle, a hypodermic needle, or an abrader) and released to dissolve the viral vaccine as the device is applied to the skin for mechanical disruption of the epidermis. Certain viral vaccines may also be coated on the device (e.g., abarding device) in the form of a gel.

The devices are preferably capable of disrupting the skin to penetrate the epidermis without penetrating the dermis. In some embodiments, the device penetrates the stratum corneum without penetrating the entire epidermis.

In certain embodiments, the viral vaccine to be administered using the methods described herein may be applied to the skin prior to abrading, simultaneous with abrading, or post-abrading.

In order to achieve the desired mechanical disruptions of the epidermis, the device should be moved across a subject's skin at least once. The subject's skin may be disrupted in alternating directions. The surface of the device may be coated with the viral vaccine. The length and thickness of the microprotrusions are selected based on the particular substance being administered and the thickness of the epidermis in the location where the device is to be applied. The microprotrusions penetrate the epidermis without piercing or passing through the entire dermis. In some embodiments, the protrusions penetrate the stratum corneum substantially without piercing or passing through the entire epidermis.

In some embodiments, the device is moved about 2 to 15 centimeters (cm). In some embodiments, the device is moved to produce a mechanically disrupted epidermal site having a surface area of about 4 cm² to about 300 cm². The extent of the mechanical disruption of the epidermis is dependent on the pressure applied during movement and the number of repetitions with the device.

In some embodiments, devices such as a scarification needle or an abrader for accurately targeting the epidermal space are provided. These devices may have solid or hollow microprotrusions. The microprotrusions can have a length up to about 1500 microns. In some embodiments, the microprotrusions have a length of about 200 to 1500 microns. In some embodiments, the microprotrusions have a length of about 300 to 1000 microns, or in the range of about 400 to 800 microns. Microneedle devices for administration of vaccine are available from BioSeren Tach Inc and described in U.S. Pat. No. 6,334,856. Skin patches are described in U.S. Pat. No. 6,706,693. These devices can be made of a biocompatible polymer or metal.

Any device known in the art for disruption of the epidermis by mechanical disruption can be used in the methods described herein. These include for example, microelectromechanical (MEMS) devices with arrays of short microneedles or microprotrusions, sandpaper-like devices, scrapers, and scarification needles.

D. Dosing

In some embodiments, an immune response to the antigen can be generated by administering between about 100-fold to about a 100-fold less pfu (plaque forming units) of the viral vector, when applied by mechanical disruption of the epidermis compared to conventional injection routes. In certain embodiments, a specific immune response to the antigen can be generated by administering between about 90-fold, 80-fold, 70-fold, 60-fold, 50-fold, 40-fold, 30-fold, 20-fold, 10-fold, 5-fold less pfu of the viral vaccine when applied by mechanical disruption of the epidermis compared to conventional injection routes. In some embodiments a single deposition of recombinantviral vaccine is required to elicit a long-lasting, potent antigen-specific immune response in the subject.

In some embodiments, the poxviruses and/or compositions thereof provided herein may also be administered on a dosage schedule, for example, an initial administration of a viral vaccine with subsequent booster administrations. In particular embodiments, a second dose of the viral vaccine is administered anywhere from two weeks to one year, preferably from one to six months, after the initial administration. Additionally, a third dose may be administered after the second dose and from three months to two years, or even longer, preferably 4 to 6 months, or 6 months to one year after the initial administration. The boosting antigen may be administered using the same viral vaccine, or as a whole protein, an immunogenic peptide fraction of the protein, another recombinant viral vector, or DNA encoding the protein or peptide. In some embodiments, different viral vaccines are used. For example, vaccinia may be followed by an avipox such as fowlpox, or vice versa. In some preferred embodiments, no booster immunization is required.

E. Viral Vector Kits for Administration

In one embodiment a kit is provided comprising, one or more containers filled with one or more of the following components: a live, modified, non-replicating or replication-impaired virus comprising an antigen and optionally comprising a co-stimulatory molecule, either in dried form (e.g. lyophilized), as a salt, or in a solution, optionally a second virus comprising a co-stimulatory molecule, either in dried form (e.g. lyophilized), as a salt, or in a solution, optionally a solution or gel to dissolve or admix the virus(es), and optionally an adjuvant. In some embodiments, the kits additionally contain a device for disrupting the epidermis. Associated with such a kit can be instructions on how to use the kit and optionally a notice in the form prescribed by a governmental agency regulating the manufacture, use or sale of pharmaceuticals or biological products, which notice reflects approval by the agency of manufacture, use or sale for human administration.

F. Methods for Determining Immune Responses

Methods for determining immune responses are known in the art. In some embodiments, viral lesions can be examined to determine the occurrence of an immune response to the virus and/or the antigen. In some embodiments, in vitro assays may be used to determine the occurrence of an immune response. Examples of such in vitro assays include ELISA assays and cytotoxic T cell (CTL) assays. In some embodiments, the immune response is measured by detecting and/or quantifying the relative amount of an antibody, which specifically recognizes an antigen in the sera of a subject who has been treated by administering the live, modified, non-replicating or replication-impaired poxvirus comprising the antigen, relative to the amount of the antibody in an untreated subject.

Techniques for the assaying antibodies and antibody filters in a sample are known in the art and include, for example, sandwich assays, ELISA and ELISpot. Polyclonal sera are relatively easily prepared by injection of a suitable laboratory animal with an effective amount of the immune effector, or antigenic part thereof, collecting serum from the animal and isolating specific sera by any of the known immunoadsorbent techniques. Antibodies produced by this method are utilizable in virtually any type of immunoassay.

The use of monoclonal antibodies in an immunoassay is preferred because of the ability to produce them in large quantities and the homogeneity of the product. The preparation of hybridoma cell lines for monoclonal antibody production derived by fusing an immortal cell line and lymphocytes sensitized against the immunogenic preparation can be achieved by techniques which are well known to those who are skilled in the art. In other embodiments, ELISA assays may be used to determine the level of isotype specific antibodies using methods known in the art.

CTL assays can be used to determine the lytic activity of CTLs, measuring specific lysis of target cells expressing a certain antigen Immune-assays may be used to measure the activation (e.g., degree of activation) of sample immune cells. Sample immune cells refer to immune cells contained in samples from any source, including from a human patient, human donor, animal, or tissue cultured cell line. The immune cell sample can be derived from peripheral blood, lymph nodes, bone marrow, thymus, any other tissue source including in situ or excised tumor, or from tissue or organ cultures. The sample may be fractionated or purified to generate or enrich a particular immune cell subset before analysis. The immune cells can be separated and isolated from their source by standard techniques.

Immune cells include both non-resting and resting cells, and cells of the immune system that may be assayed, including, but not limited to, B lymphocytes, T lymphocytes, natural killer (NK) cells, lymphokine-activated killer (LAK) cells, monocytes, macrophages, neutrophils, granulocytes, mast cells, platelets, Langerhans cells, stem cells, dendritic cells, and peripheral blood mononuclear cells.

Immune cell activity that may be measured include, but is not limited to (1) cell proliferation by measuring the cell or DNA replication; (2) enhanced cytokine production, including specific measurements for cytokines, such as γIFN, GM-CSF, or TNF-alpha, IFN-alpha, IL-6, IL-10, IL-12; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; (9) chemokine secretion such as IP-10; (10) expression of costimulatory molecules (e.g., CD80, CD 86) and maturation molecules (e.g., CD83), (12) upregulation of class II MHC expression; and (13) apoptosis, which refers to fragmentation of activated immune cells under certain circumstances, as an indication of abnormal activation.

Reporter molecules may be used for many of the immune assays described. A reporter molecule is a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic colour visually detectable with a light microscope. The fluorescent labeled antibody is allowed to bind to the first antibody-antigen complex. After washing off the unbound reagent, the remaining tertiary complex is then exposed to the light of the appropriate wavelength the fluorescence observed indicates the presence of the antigen of interest.

Examples of some common immune assays are:

Cell Proliferation Assay: Activated immune cell proliferation is intended to include increase in cell number, cell growth, cell division, or cell expansion, as measured by cell number, cell weight, or by incorporation of radiolabelled nucleic acids, amino acids, proteins, or other precursor molecules. As one example, DNA replication is measured by incorporation of radioisotope labels. In some embodiments, cultures of stimulated immune cells can be measured by DNA synthesis by pulse-labeling the cultures with tritiated thymidine ($^3$H-Tdr), a nucleoside precursor that is incorporated into newly synthesized DNA. Thymidine incorporation provides a quantitative measure of the rate of DNA synthesis, which is usually directly proportional to the rate of cell division. The amount of $^3$H-labeled thymidine incorporated into the replicating DNA of cultured cells is determined by scintillation counting in a liquid scintillation spectrophotometer. Scintillation counting yields data in counts per minute (cpm) which may then be used as a standard measure of immune cell responsiveness. The cpm in resting immune cell cultures may be either subtracted from or divided into cpm of the primed immune cells, which will yield a stimulation index ratio.

Flow cytometry can also be used to measure proliferation by measuring DNA with light scatter, Coulter volume and fluorescence, all of which are techniques that are well known in the art.

Enhanced Cytokine Production Assay: A measure of immune cell stimulation is the ability of the cells to secrete cytokines, lymphokines, or other growth factors. Cytokine production, including specific measurements for cytokines, such as γIFN, GM-CSF, or TNF-alpha, may be made by radioimmunoassay (RIA), enzyme-linked immunoabsorbent assay (ELISA), bioassay, or measurement of messenger RNA levels. In general, with these immunoassays, a monoclonal antibody to the cytokine to be measured is used to specifically bind to and thus identify the cytokine. Immunoassays are well known in the art and can include both competitive assays and immunometric assays, such as forward sandwich immunoassays, reverse sandwich immunoassays and simultaneous immunoassays.

In each of the above assays, the sample-containing cytokine is incubated with the cytokine-specific monoclonal antibody under conditions and for a period of time sufficient to allow the cytokines to bind to the monoclonal antibodies. In general, it is desirable to provide incubation conditions sufficient to bind as much cytokine and antibody as possible, since this will maximize the signal. Of course, the specific concentrations of antibodies, the temperature and time of incubation, as well as other such assay conditions, can be varied, depending upon various factors including the concentration of cytokine in the sample, the nature of the sample, and the like. Those skilled in the art will be able to determine operative and optimal assay conditions for each determination by employing routine experimentation.

Cell-Mediated Target Cell Lysis Assay: Another type of indicator for degree of immune cell activation is immune cell-mediated target cell lysis, which is meant to encompass any type of cell killing, including cytotoxic T lymphocyte activity, apoptosis, and the induction of target lysis by molecules secreted from non-resting immune cells stimulated to activity. Cell-mediated lympholysis techniques typically measure the ability of the stimulated immune cells to lyse $^{51}$Cr-labeled target cells. Cytotoxicity is measured as a percentage of $^{51}$Cr released in specific target cells compared to percentage of $^{51}$Cr released from control target cells. Cell killing may also be measured by counting the number of target cells, or by quantifying an inhibition of target cell growth.

Cell Differentiation Assay: Another indicator of immune cell activity is immune cell differentiation and maturation. Cell differentiation may be assessed in several different ways. One such method is by measuring cell phenotypes. The phenotypes of immune cells and any phenotypic changes can be evaluated by flow cytometry after immunofluorescent staining using monoclonal antibodies that will bind membrane proteins characteristic of various immune cell types.

A second means of assessing cell differentiation is by measuring cell function. This may be done biochemically, by measuring the expression of enzymes, mRNA's, genes, proteins, or other metabolites within the cell, or secreted from the cell. Bioassays may also be used to measure functional cell differentiation.

Immune cells express a variety of cell surface molecules which can be detected with either monoclonal antibodies or polyclonal antisera. Immune cells that have undergone differentiation or activation can also be enumerated by staining for the presence of characteristic cell surface proteins by direct immunofluorescence in fixed smears of cultured cells.

Mature B cells can be measured in immunoassays, for example, by cell surface antigens including CD19 and CD20 with monoclonal antibodies labeled with fluorochromes or enzymes may be used to these antigens. B cells that have differentiated into plasma cells can be enumerated by staining for intracellular immunoglobulins by direct immunofluorescence in fixed smears of cultured cells.

Immunoglobulin Production Assay: B cell activation results in small, but detectable, quantities of polyclonal immunoglobulins. Following several days of culture, these immunoglobulins may be measured by radioimmunoassay or by enzyme-linked immunosorbent assay (ELISA) methods.

B cells that produce immunoglobulins can also be quantified by the reversed hemolytic plaque assay. In this assay, erythrocytes are coated with goat or rabbit anti-human immunoglobulins. These immunoglobulins are mixed with the activated immunoglobulin-producing lymphocytes and semi-solid agar, and complement is added. The presence of hemolytic plaques indicates that there are immunoglobulin-producing cells.

Chemotactic Factor Assay: Chemotactic factors are molecules which induce or inhibit immune cell migration into or out of blood vessels, tissues or organs, including cell migration factors. The chemotactic factors of immune cells can be assayed by flow cytometry using labeled monoclonal antibodies to the chemotactic factor or factors being assayed. Chemotactic factors may also be assayed by ELISA or other immunoassays, bioassays, messenger RNA levels, and by direct measurements, such as cell counting, of immune cell movements in specialized migration chambers.

Addback Assays When added to fresh peripheral blood mononuclear cells, autologous ex vivo activated cells exhibit an enhanced response to a "recall" antigen, which is an antigen to which the peripheral blood mononuclear cells had previously been exposed. Primed or stimulated immune cells should enhance other immune cells response to a "recall" antigen when cultured together. These assays are termed "helper" or "addback" assays. In this assay, primed or stimulated immune cells are added to untreated, usually autologous immune cells to determine the response of the untreated cells. The added primed cells may be irradiated to prevent their proliferation, simplifying the measurement of the activity of the untreated cells. These assays may be particularly useful in evaluating cells for blood exposed to virus. The addback assays can measure proliferation, cytokine production, and target cell lysis as described herein.

The above-described methods and other additional methods to determine an immune response are well known in the art.

G. Additional Agents to Administer with Viral Vector

In some embodiments, the method(s) for treating or preventing cancer described herein may be used in combination with one or more anti-cancer agents. In some embodiments, the method(s) for treating or preventing infections (or diseases described herein may be used in combination with one or more anti-bacterial agents, anti-viral agents, anti-fungal agents, or anti-protozoal agents.

The present invention is further illustrated by the following non-limiting examples. The entire contents of all of the references (including literature references, issued patents, published patent applications, and co-pending patent applications) cited throughout this application are hereby expressly incorporated by reference.

EXAMPLES

Example 1

Epidermal VV Immunization Via Skin Scarification Generates Significantly Stronger Cellular and Humoral Immunity than the Conventional Injection Routes A mouse model of VV skin scarification was developed. The acute epidermal pox reaction developed in scarified mice closely resembles that of human smallpox vaccines. Using this model, a rigorous comparison of the primary and memory adaptive immune response following vaccinia virus (VV) immunization via skin scarification (s.s.), subcutaneous (s.c.), intradermal (i.d.) and intramuscular (i.m.) injection was undertaken. The highly immunogenic intraperitoneal (i.p.) injection route, although not used for immunization clinically, was included as positive control for VV-specific immune responses.

VV skin scarification induced significantly stronger primary and memory T cell response, as well as higher serum VV-specific IgG levels, compared to the conventional injection routes (s.c., i.d., and i.m.). Long-term T cell memory and serum IgG levels were comparable in VV scarified mice and i.p. immunized mice. FIGS. 1A-1D. Thus, localized epidermal VV immunization via skin scarification achieves comparable immunogenicity compared to i.p. infection which establishes systemic viral infection, according to IFN-$\gamma$ response and serum IgG level.

Example 2

Figure 2:
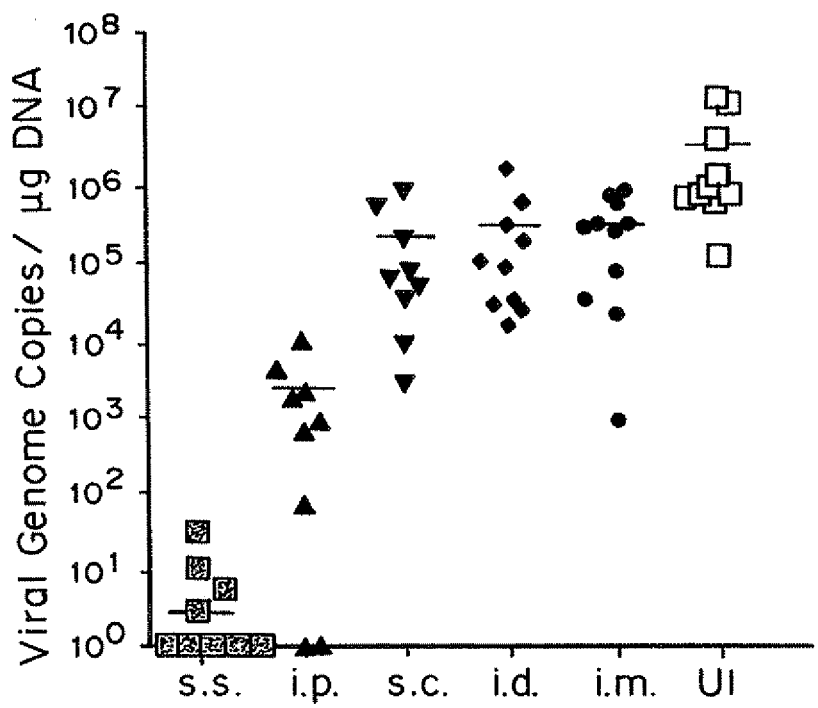
FIG. 2. VV skin scarification led to superior protection against secondary cutaneous virus challenge compared to other routes of immunization. B6 mice were immunized with VV via various routes as indicated. Eight weeks following immunization, the immune mice were challenged with secondary cutaneous VV infection. Six days after challenge, viral load at the challenged site was measured by real-time PCR. Unimmunized mice were included as control.

VV Skin Scarification Provides Superior Protection Against Secondary Antigenic Challenge It was determined whether VV skin scarification could provide better protection against secondary challenge using three different models. The first challenge model was cutaneous poxvirus infection (via skin infection). This model was chosen for two reasons. First, clinically, the protection efficacy of smallpox vaccine candidates is evaluated by challenging vaccinated individuals with Dryvax skin scarification. Second, natural poxvirus infection can be acquired via cutaneous exposure to the viruses, especially at injured skin area. Following skin challenge, viral load in skin was determined by VV-specific real-time PCR (FIG. 2). Compared to unimmunized control mice, mice immunized by s.c., i.d., and i.m. injection all demonstrated partial protection, with 15, 9.5 and 3-fold reduction in viral load, respectively. 3-log reduction in viral load was achieved in i.p. immunized mice. Strikingly, all the mice previously immunized via skin scarification completely cleared the virus by this time point. Therefore, skin scarification provided superior protection against secondary cutaneous poxvirus challenge compared to the injection routes, including the highly immunogenic i.p. route.

Figure 3A:
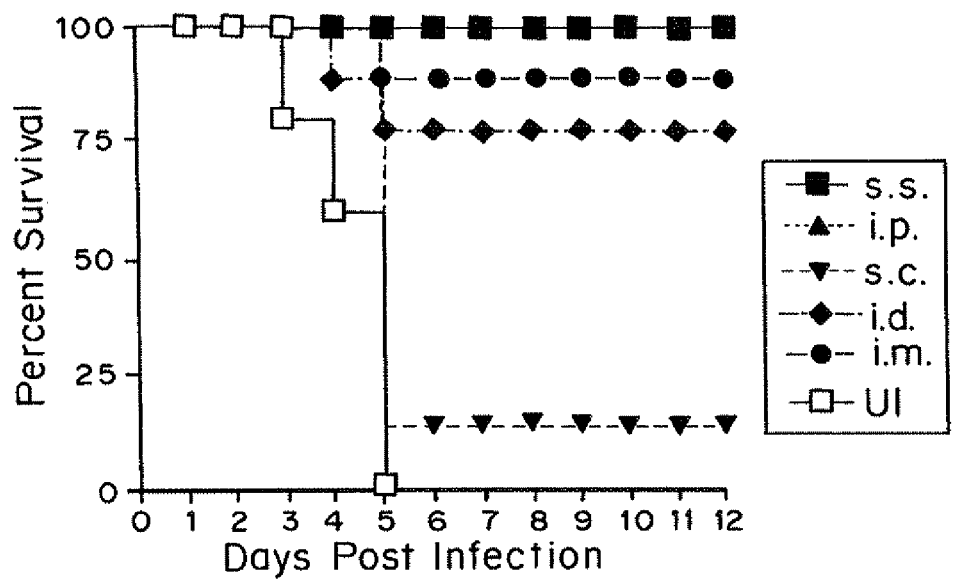
FIG. 3A-D. Skin scarification provided superior protection against secondary intranasal viral challenge.
Figure 3B:
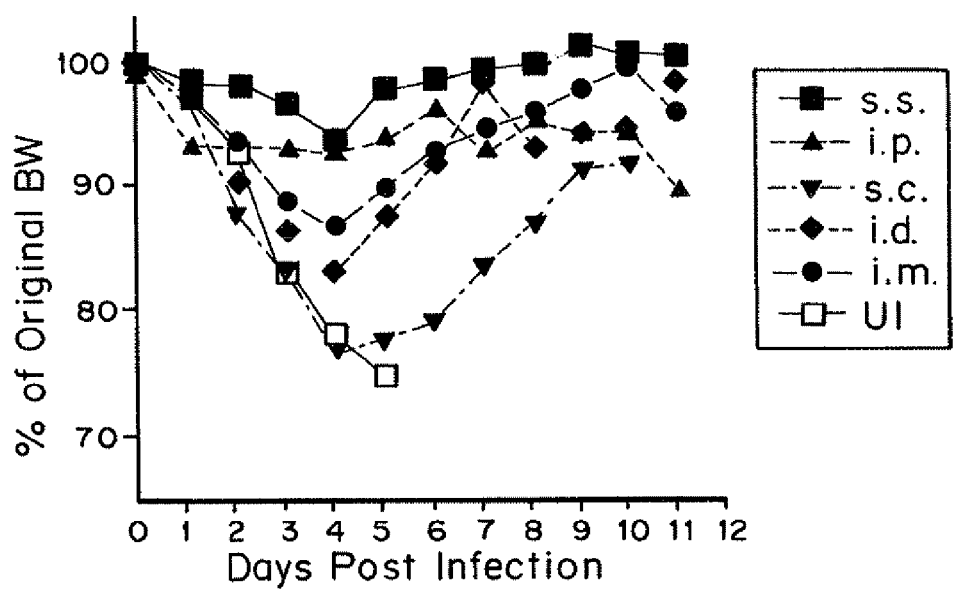
Figure 3C:
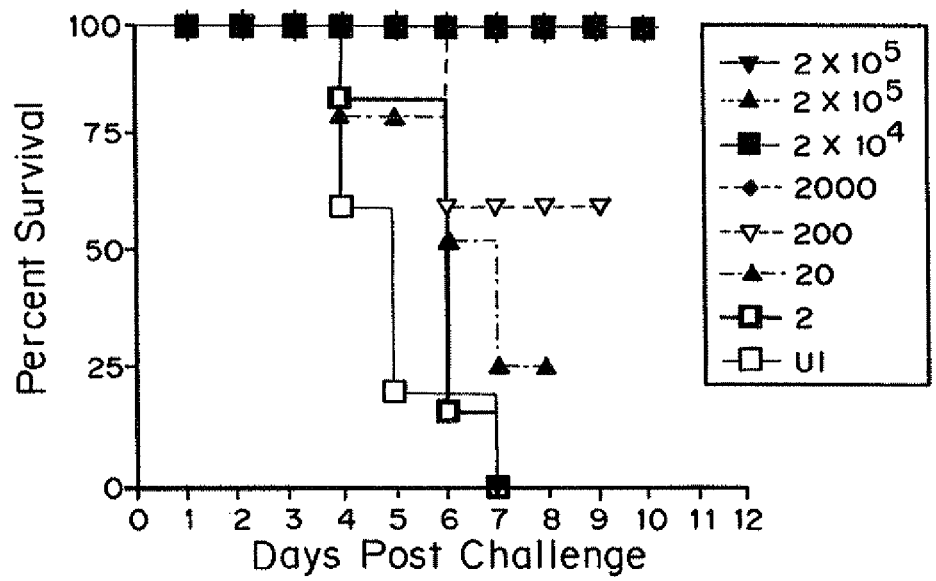
Figure 3D:
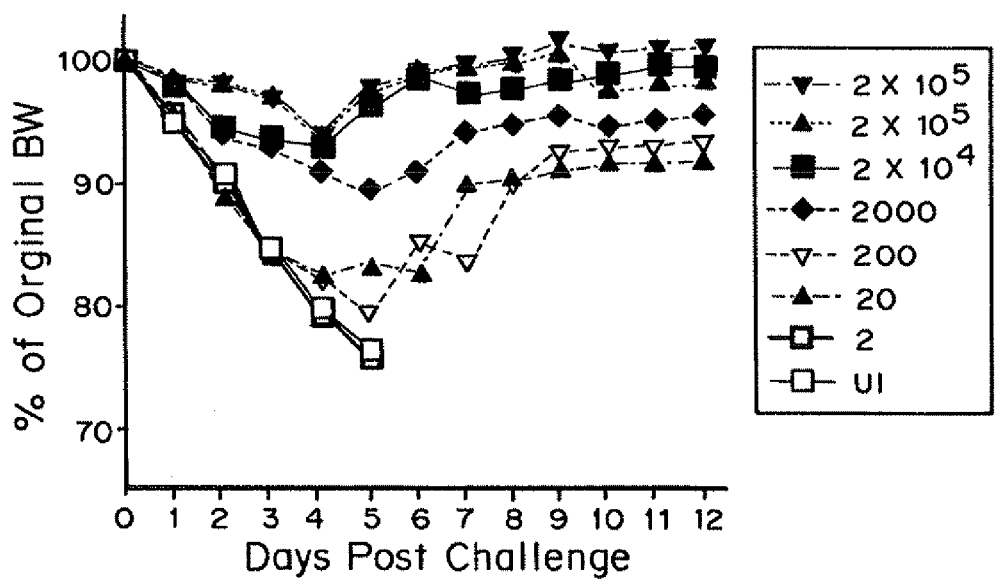

Natural poxvirus infection is primarily transmitted by respiratory aerosol. Therefore, the protection efficacy of various immunization routes against lethal intranasal infection by pathogenic Western Reserve vaccinia virus (WR-VV) was evaluated. As shown in FIG. 3A,3B, mice immunized via s.c., i.d. and i.m. injection routes (at $2\times10^6$ pfu dose) developed apparent clinical illness (manifested by the significant loss of body weight, BW), and were only partially protected from mortality. In contrast, mice immunized via s.s. and i.p. routes were completely protected with 100% survival and minimal BW changes. In fact, skin scarification route achieved better protection efficacy than s.c., i.d. and i.m. routes even at a 1000× lower dose (FIG. 3C,3D). Thus, VV immunization via skin scarification protected respiratory mucosa more effectively than the conventional immunization routes.

Figure 4:
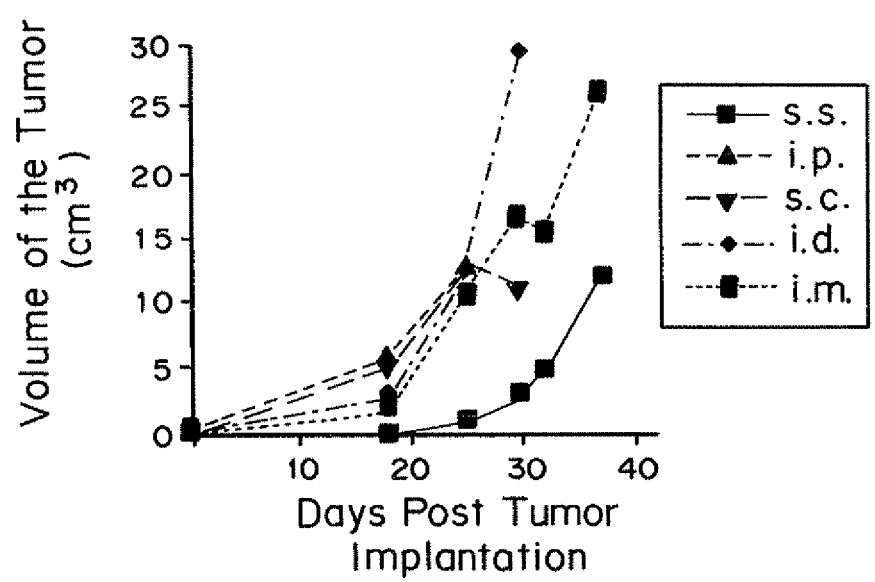
FIG. 4 Immunization via VV skin scarification provides superior protection against intradermal melanoma challenge. B6 mice were immunized with rVV-ova via the indicated routes. The immune mice were challenged 4 weeks later with intradermal injection of B16-ova melanoma cells. Tumor growth was monitored in the challenged mice for up to 40 days and plotted as tumor volume over days post tumor implantation.

It was then investigated whether the superior protection associated with VV skin scarification can be extended to non-viral challenge model. C57B1/6 mice were immunized with recombinant vaccinia virus (rVV) expressing ovalbumine (OVA) $K^b$ epitope $Ova_{257-264}$ via different routes, and challenged with B16 melanoma cells expressing OVA intradermally 5 weeks following immunization. By 18 days after tumor implantation, all the mice immunized via the injection routes (s.c., i.d., i.m., and i.p.) developed large cutaneous melanoma mass. Remarkably, no visible or palpable tumor was detected on any of the skin scarified mice. Although eventually tumor developed in all the B16-OVA challenged mice, the tumor growth was significantly delayed (FIG. 4) and survival was greatly improved in the scarification group compared to other groups. Given the vaccine and tumor cells only share a single CD8 T cell epitope, and mice were only given a single dose VV skin scarification, these results are remarkably promising and of broad clinical implication. It is highly possible that over time, the OVA expression is lost from the B16 tumor cells under the immune selection, rendering $Ova_{257-264}$-specific $CD8^+$ T cell memory response ineffective to suppress tumor growth.

Example 3

Memory T Cells but not Ab are Required for VV Skin Scarification-Associated Protection Against Secondary Challenge To investigate the mechanism underlying the superior protective efficacy following poxvirus skin scarification, the relative contribution of humoral and cellular response in skin scarification-associated immune protection was studied. Wild type (wt) and B cell-deficient μMT mice were immunized with VV by skin scarification or i.p. injection, the two most immunogenic routes in this study. The memory mice were then challenged by secondary cutaneous or intranasal poxvirus infection.

Figure 5A:
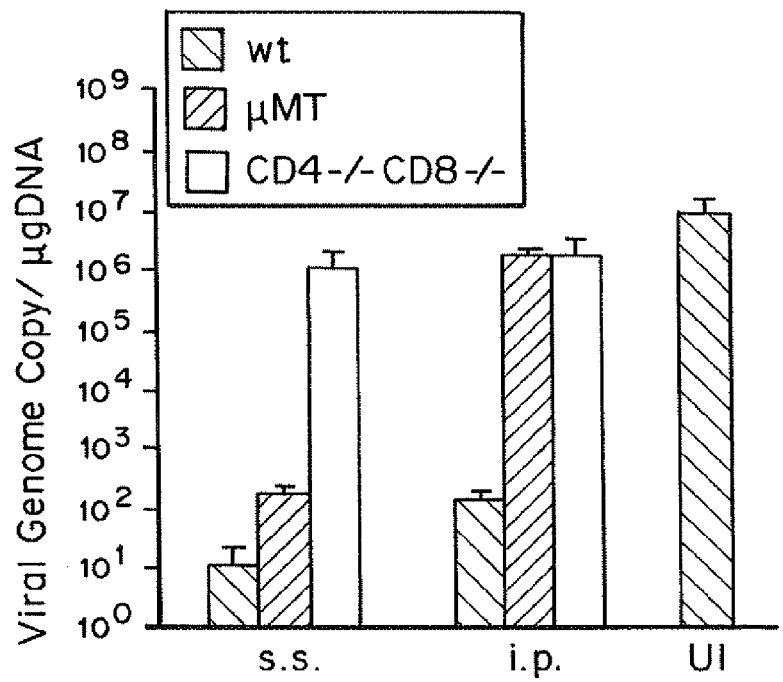
FIG. 5A-C. T-cell mediated immune response was required for the superior protection against secondary cutaneous challenge following VV skin scarification. WT or B cell deficient mMT mice were immunized with VV via skin scarification or i.p. injection. Mice were then challenged by secondary VV cutaneous infection at 6 weeks p.i.
Figure 5B:
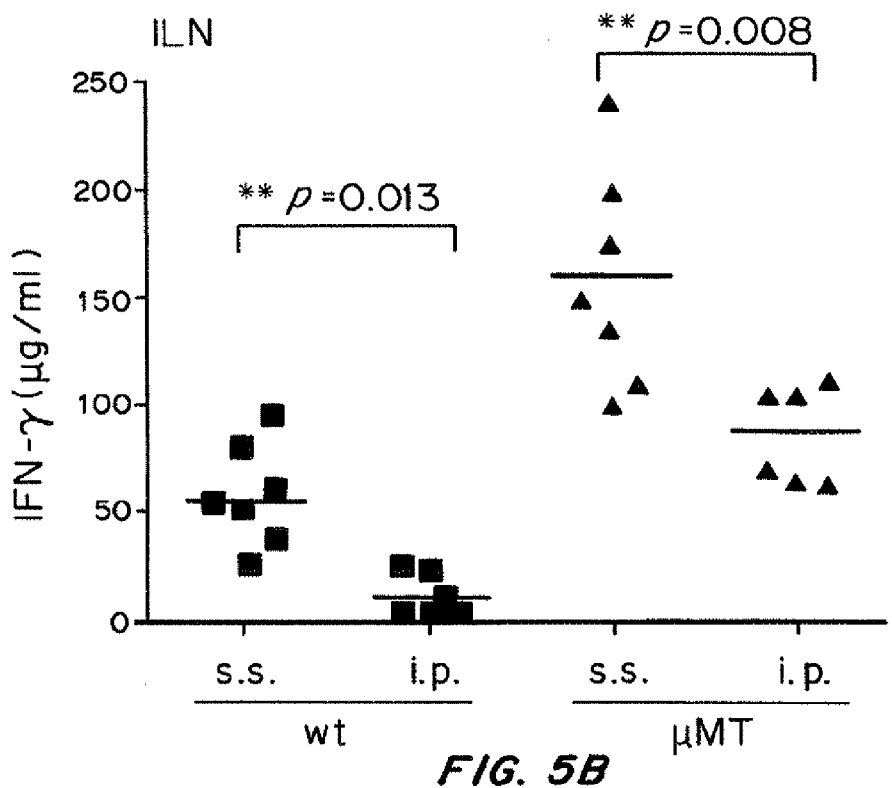
Figure 5C:
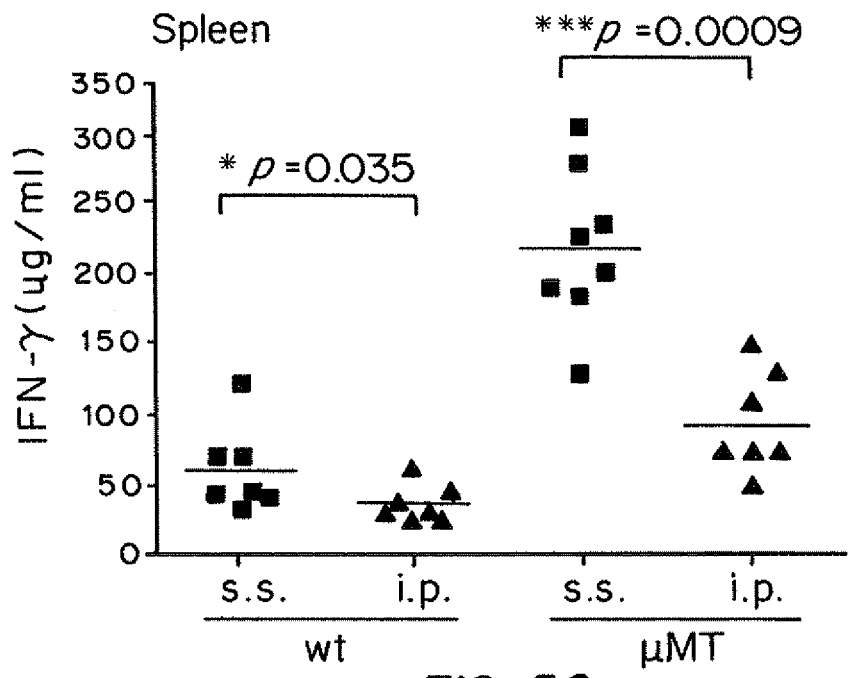

As shown in FIG. 5A, when challenged with VV on skin, the i.p. immunized μMT mice had a viral load 4-log higher than that of the i.p. immunized wt mice. μMT mice immunized via s.s. route still demonstrated strong protection against cutaneous challenge, with a viral load comparable to that of the wt mice immunized via skin scarification. However, when T cells were depleted from the wt memory mice before and during challenge (by large dose treatment with anti-CD4 and anti-CD8 mAbs), the immune protection was completely abrogated in both s.s. and i p immunization groups. This data indicate that while both T cell and Ab are required for the protection against cutaneous challenge following i p immunization, T cell memory response alone following VV skin scarification is strong enough to effectively control cutaneous challenge. Indeed, secondary T cell response in both spleen and lymph node (LN) draining the challenged skin was significantly stronger in scarified immune mice than in i.p. immunized mice (FIG. 5B, C). The difference between the immunization groups was even more striking in μMT mice.

Challenged skin tissues from different groups of mice were further examined microscopically for the presence of T cells. Secondary T cell response in challenged wt and mMt immune mice was assessed in skin-draining inguinal lymph nodes and spleen on day 6 following challenged. Skin samples were harvested from the challenged site at 4 days after challenge. Skin-infiltrating $CD3^+$ T cells were identified by immunohistochemistry. Strikingly, massive $CD3^+$ T cell infiltration was observed in the basal epidermis and dermis of mice immunized via s.s. route, while only a few T cells were scattered in the skin harvested from all other immunization groups. Collectively, these data indicate that VV skin scarification is uniquely potent in generating large number of skin-homing $T_{cm}$ that are highly protective against secondary cutaneous antigenic challenge.

Figure 6A:
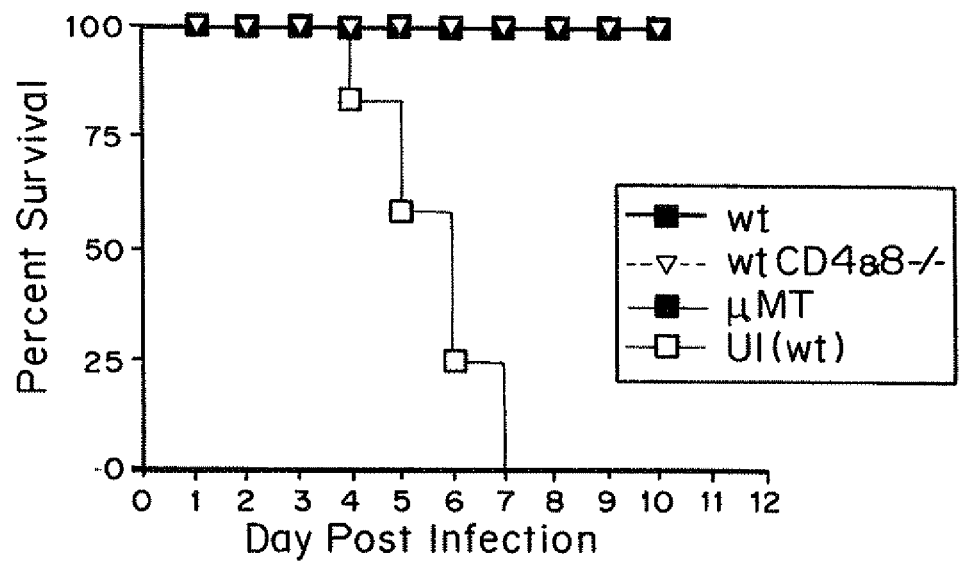
FIG. 6A-D. T cells but not Ab were important for the prevention of illness, although neither T cells nor B cells were required for survival after lethal intranasal WR-VV challenge. Wild type (wt) or B cell deficient μMT mice were immunized with VV via skin scarification (FIG. 6A-6B) or i.p. injection (FIG. 6C-6D). Mice were then challenged by lethal WR-VV intranasal infection at 6 weeks p.i. In some groups of wt mice, both CD4$^+$ and CD8$^+$ T cells were depleted before and during challenge by large doses of anti-CD4 and anti-CD8 mAb treatment. Mice survival (FIG. 6A, 6C) and change of BW (FIG. 6B,6Dd) were monitored daily after the challenge.
Figure 6B:
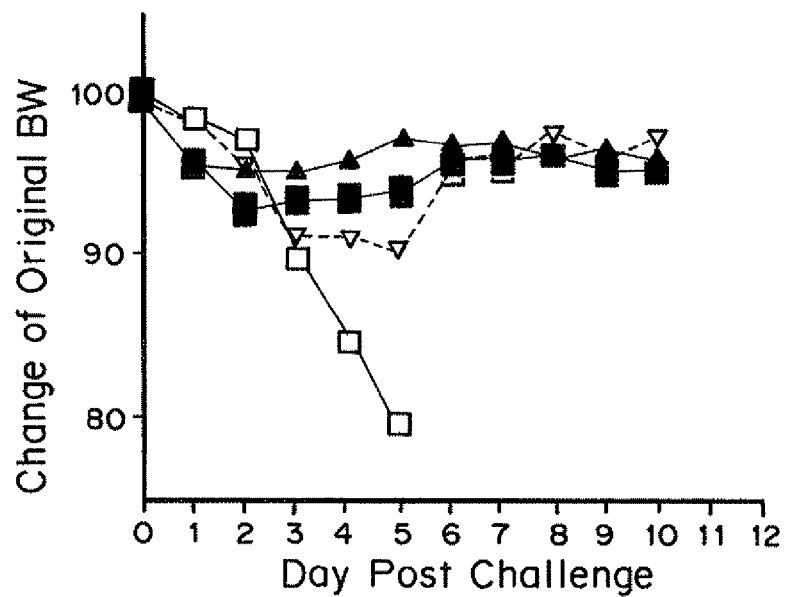
Figure 6C:
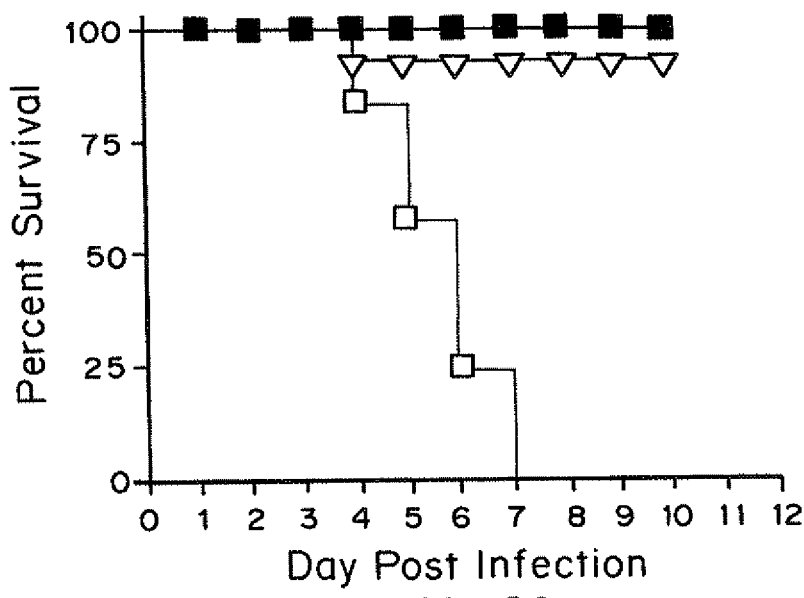
Figure 6D:
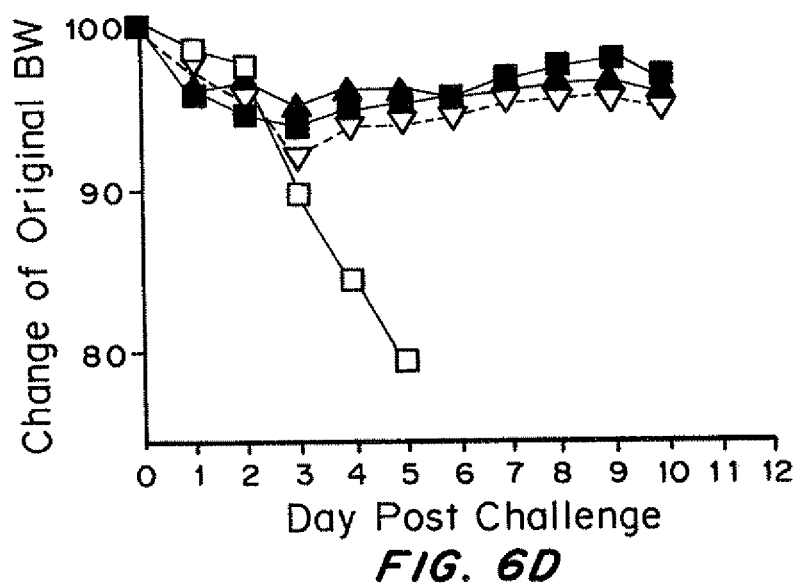

Similarly, T cell memory seemed to be more important than Ab response for the complete protection against intranasal challenge. Wt and μMT mice were immunized with VV via skin scarification and lethally challenged with WR-VV via intranasal infection. Both strains of mice were completely protected against mortality (FIG. 6A) with minimal change of BW (FIG. 6B). However, depletion of T cells from wt memory mice led to more pronounced BW loss (FIG. 6D), although all the T cell-depleted immune mice survived the challenge (FIG. 6C). This data indicate protective $T_{cm}$ either residing in or able to rapidly migrate into respiratory epithelial lining are generated by epicutaneous VV immunization via skin scarification, along with the skin-homing $T_{cm}$. These cells play an important role in the immune surveillance against aerosol-transmitted pathogens.

Example 4

VV Skin Scarification Generates Large Number of Skin-Homing $T_{eff}/T_{cm}$, as well as T Cells with Highly Versatile Homing Ability by Primary and Secondary Tissue Homing Imprinting Programs in Regional LN How antigen-specific T cells develop the highly versatile homing ability to provide systemic immune protection following a local VV infection restricted to skin was investigated by adoptively transferring naïve CFSE-labeled $Thy1.1^+$ $Ova_{257-264}$-specific OT-I T cells into $Thy1.2^+$ wt mice and subsequently tracking their in vivo activation, proliferation and migration following skin scarification or i.p. infection with $rVV$-$Ova_{257-264}$.

Figure 7A:
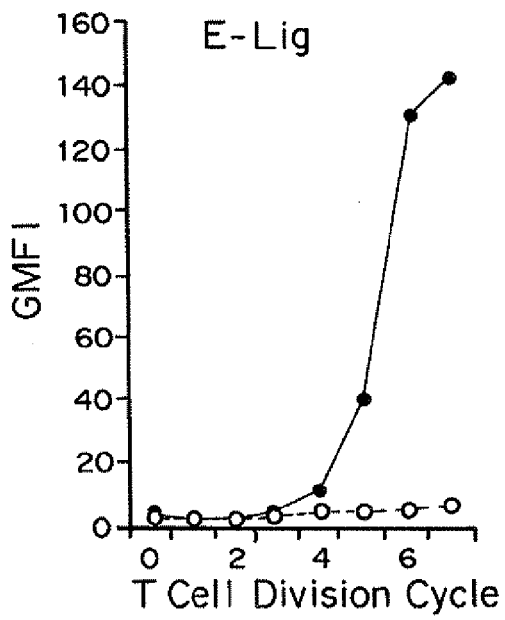
FIG. 7A-7D. The LN of T cell activation imprints differential expression of skin or gut-homing molecules on CD8$^+$ T cells as early as 60 h after infection. CFSE-labeled Thy1.1$^+$ OT-1 cells were adoptively transferred into Thy1.2$^+$ B6 mice. Recipient mice were then infected with rVV-ova by either skin scarification or i.p. injection.
Figure 7B:
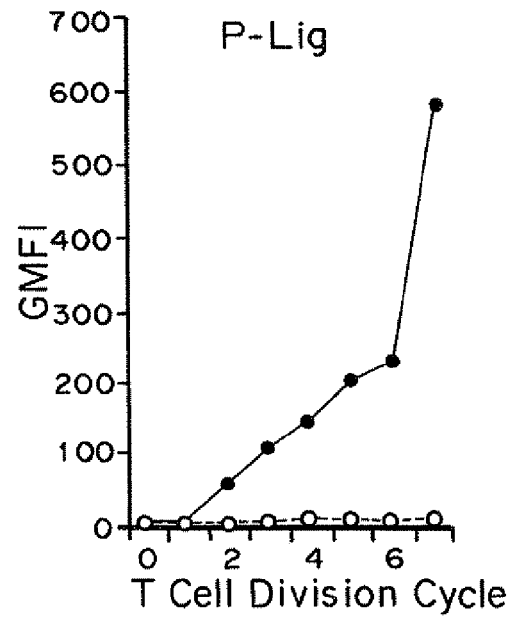
Figure 7C:
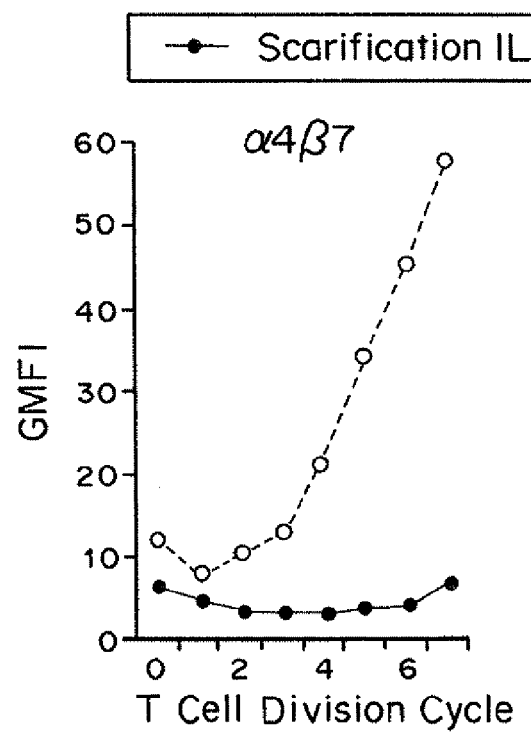
Figure 7D:
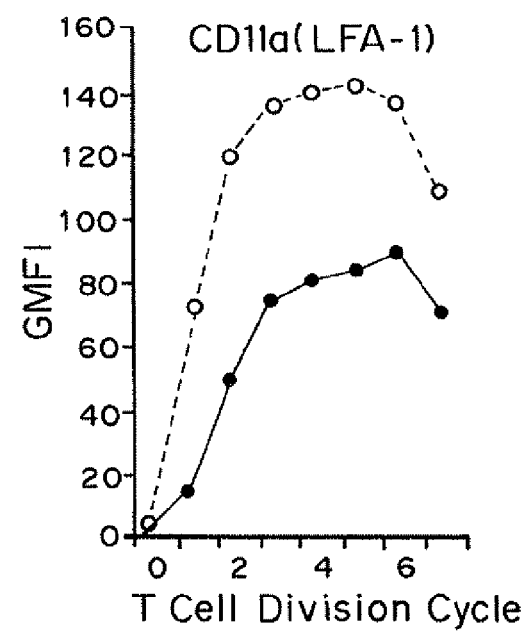

OT-I cells proliferated extensively within skin-draining inguinal LN (ILN) as early as 60 h following skin scarification, while similar proliferation was seen in the gut-draining mesenteric LN (MLN) after i.p. infection. These OT-I cells significantly down-regulated LN-homing molecule CD62L, which is highly expressed on naïve and $T_{cm}$ T cells circulating among secondary lymphoid tissues. Concurrently, there was a robust up-regulation of skin-homing molecule E-Lig (FIG. 7A) and P-Lig (P-selectin ligands) (FIG. 7B) on OT-I cells activated within ILN, and gut-homing molecule $\alpha 4\beta 7$ (FIG. 7C) on OT-I cells activated within MLN. The expression of the tissue-homing molecules was upregulated after 3 cell divisions and continued to increase as a function of cell division (FIG. 7D).

Thus, early upon activation, antigen-specific T cells are imprinted with tissue-specific homing phenotype within regional LN where priming occurs (primary homing imprinting). This enabled the activated T cells to migrate specifically to the infected tissues as early as day 3 after VV skin scarification. This surprisingly rapid T cell recruitment into skin after primary VV skin scarification had not been previously appreciated.

Five days after VV skin scarification, T cells activated in skin-draining ILN migrated throughout secondary lymphoid tissues without virus or viral antigen dissemination. Lymphocytes were prepared from the indicated tissues 5 days after rVV-ova skin scarification. The proliferation of OT-1 cells was analyzed by flow cytometry. RNA samples were prepared from the indicated tissues at day 5 after VV scarification. VV infection was measured by real-time RT-PCT. Data represent the averages±s.d. of 4 independent experiments with three mice per group. Antigen presenting cells were purified with anti-MHC Class II magnetic beads from ILN, MLN and spleen of B6 mice 4 days following skin scarification with rVV-ova. The cells were co-cultured with CFSE-labeled Thy1.1$^+$ OT-1 cells for 60 h. OT-1 cell activation and proliferation was monitored by flow cytometer. The histograms were gated on Thy1.1$^+$ population.

Figure 8:
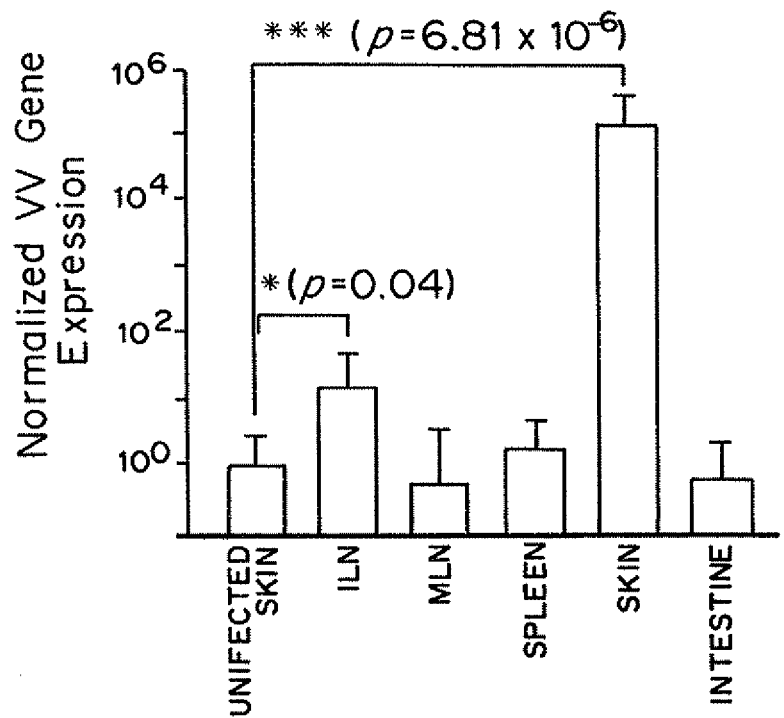
FIG. 8. Five days after VV skin scarification, T cells activated in skin-draining ILN migrated throughout secondary lymphoid tissues without virus or viral antigen dissemination. RNA samples were prepared from the indicated tissues at day 5 after VV scarification. VV infection was measured by real-time RT-PCT. Data represent the averages±s.d. of 4 independent experiments with three mice per group.

Several additional unanticipated findings were made. In contrast to the highly specific tissue trafficking at 60 h following infection, activated OT-I cells had disseminated into non-draining LN by 5 days after rVV-ova skin scarification. This was not accompanied by systemic dissemination of VV or VV antigen-bearing antigen presenting cells (APC), since vaccinia gene expression was not detected outside skin or skin-draining LN by the highly sensitive real time RT-PCR, and APC isolated from MLN and spleen failed to activate OT-I cells in vitro. FIG. 8. Therefore, a subset of ILN-activated OT-I cells disseminate throughout lymphoid tissues and continued to divide in the absence of continued antigen stimulation. Unexpectedly, they also expressed additional tissue-specific homing molecules.

Figure 9A:
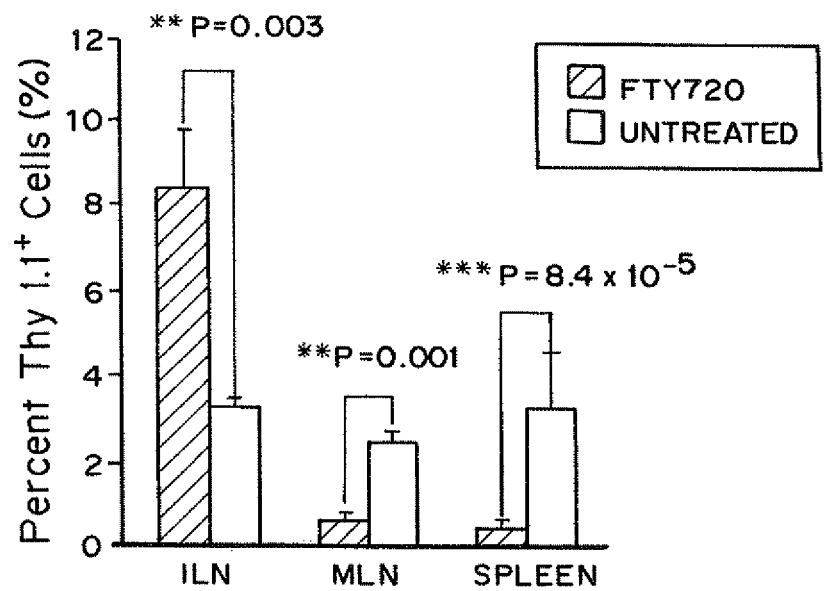
FIG. 9A-9C. At day 5 after skin scarification with rVV-ova, the gut-homing molecule α4β7 was upregulated on disseminated OT-1 CD8+ cells by secondary homing imprinting. ILN and MLN were harvested at day 5 after scarification with rVV-ova. The expression of the indicated homing markers on Thy1.1$^+$ OT-1 cells was determined by flow cytometry. Dot plots were gated on Thy1.1$^+$ cells. B6 mice that had received Thy1.1$^+$ OT-1 cells were given daily injections of FTY720 starting 24 h before scarification with rVV-ova. On day 5 after infection, lymphocytes from the indicated tissues were harvested and analyzed by flow cytometry. The percentages of Thy1.1$^+$ cells in total lymphocytes.
Figure 9B:
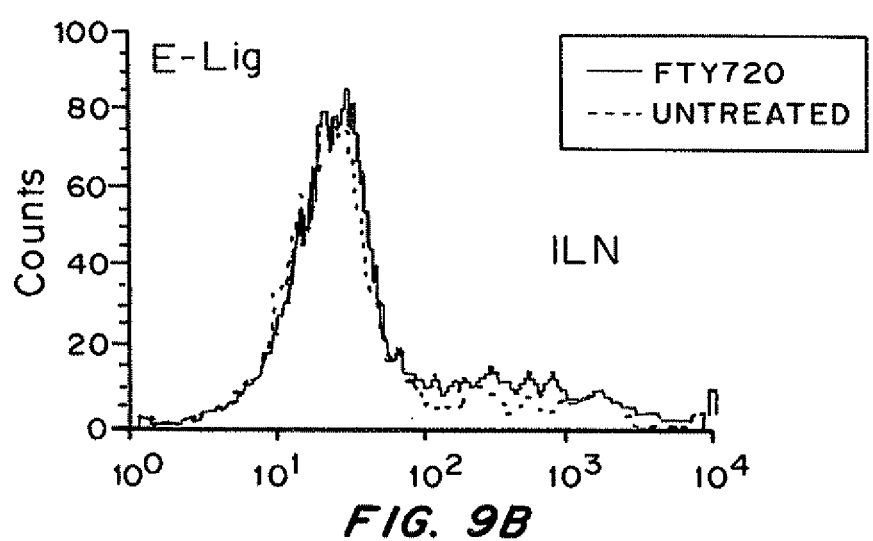
Figure 9C:
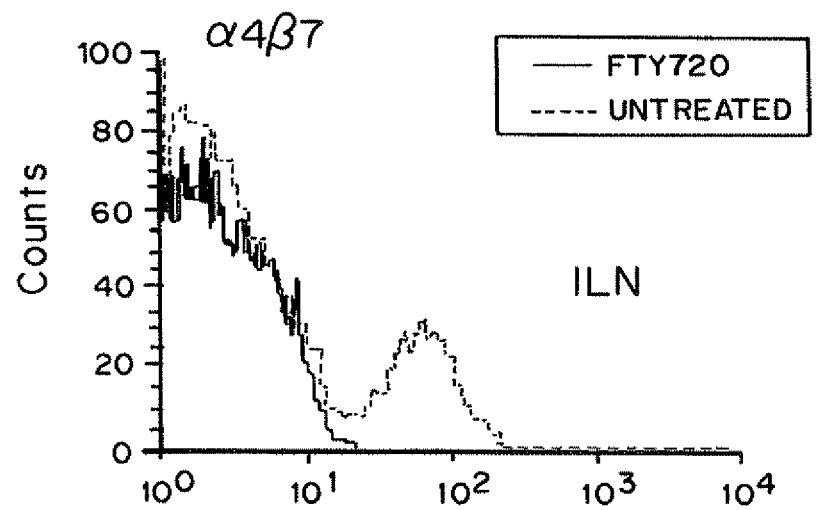

Gut-homing $\alpha 4\beta 7$ was upregulated on the proliferating OT-I cells. When the egress of OT-I cells from ILN after their activation was blocked using FTY720, a functional antagonist of sphingosine 1-phosphate that regulates lymphocyte egress from lymphoid tissues (FIG. 9A), the expression of E-Lig on OT-I cells was unaffected (FIG. 9B), however, $\alpha 4\beta 7$ on OT-I cells was abrogated (FIG. 9C). This data strongly indicate the upregulation of gut homing molecules occurred subsequent to OT-I migration into MLN (secondary tissue homing imprinting). A similar process may happen in other non-draining LN where putative lung and mucosal trafficking molecules are expressed.

Figure 10:
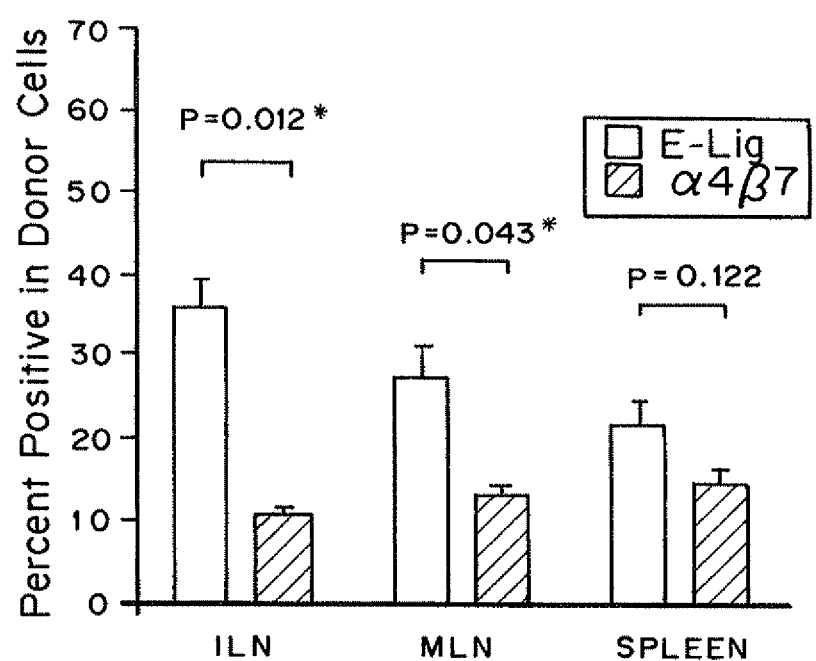
FIG. 10. The primary and secondary imprint of tissue-specific homing molecule during acute viral infection was maintained during the memory phase. Lymphocytes were harvested from the indicated tissues on day 30 after rVV-ova skin scarification. The percentages of E-Lig$^+$ or α4β7$^+$ cells in Thy1.1$^+$ OT-1 cells were analyzed by flow cytometry. Data represent the average ± s.d. of 6 mice.

When T cells were examined at 30 days after infection, both primary (skin-specific E-Lig) and secondary (gut-specific $\alpha 4\beta 7$) homing molecules persisted on memory OT-I cells (FIG. 10). These data collectively indicate a mechanism by which localized VV immunization via skin scarification generates protective T cell response for both immediate skin-specific immune control at the virus entry site, and a more flexible systemic protection against potential viral dissemination or secondary challenge at a distinct anatomic location, such as respiratory epithelium.

Example 5

MVA Skin Scarification Represents a Immunization Strategy that is Superior, Safe and Effective The highly attenuated replication-defective VV strain MVA has been actively explored as a promising live viral vaccine vector because of its impressive safety and immunogenicity profile in both preclinical and clinical studies. MVA vaccines have been administered exclusively via injection routes, and never via skin scarification. This may due to the intuitive assumption that viral replication in epidermis is required for the development of pox lesion and the subsequent strong protection against challenge.

Figure 11A:
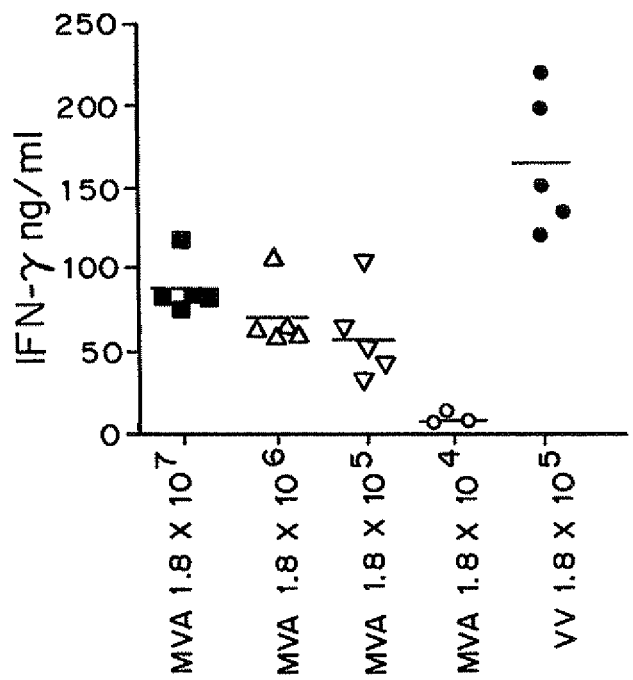
FIG. 11A-D. MVA immunization via skin scarification (s.s.) elicits dose-dependent immune response. B6 mice were immunized via s.s. with different doses of MVA (from left to right: 1.8×10$^7$, 1.8×10$^6$, 1.8×10$^5$ and 1.8×10$^4$ pfu). At day 7 post-immunization, pox lesions were observed in a dose-dependent manner.
Figure 11B:
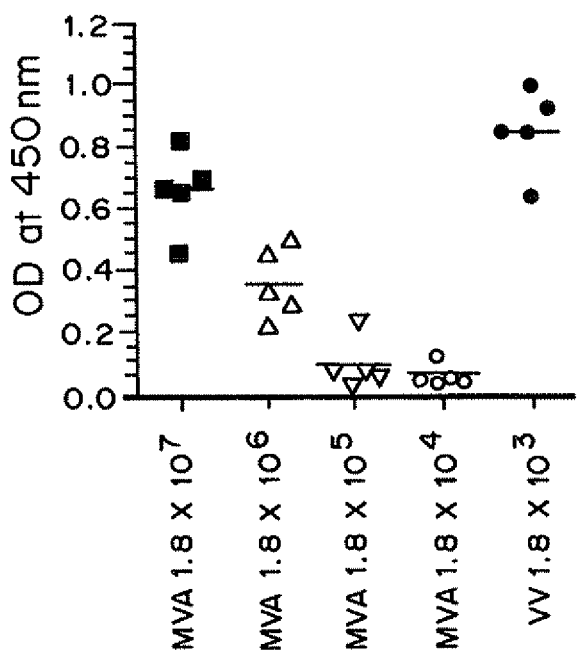
Figure 11C:
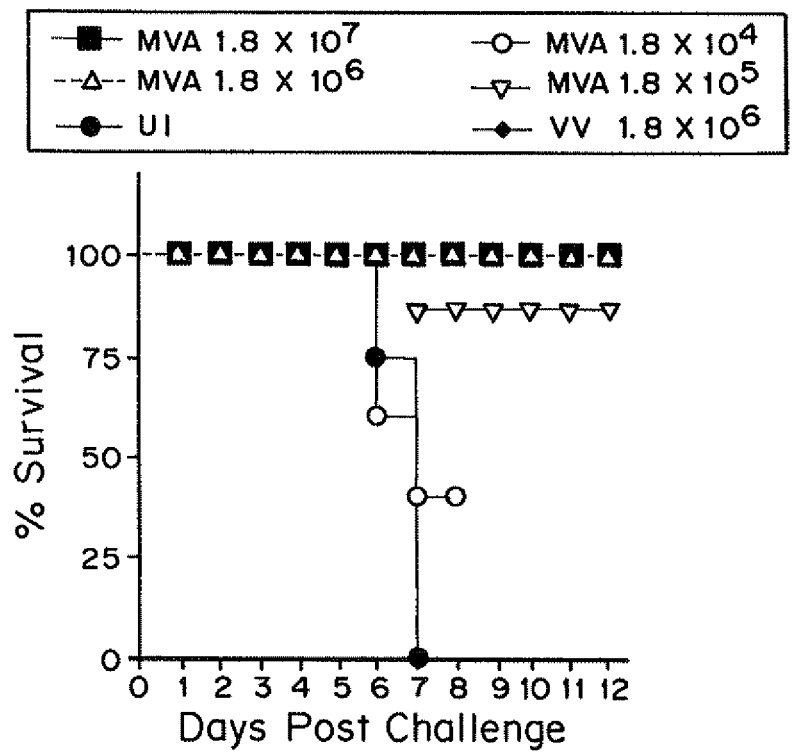
Figure 11D:
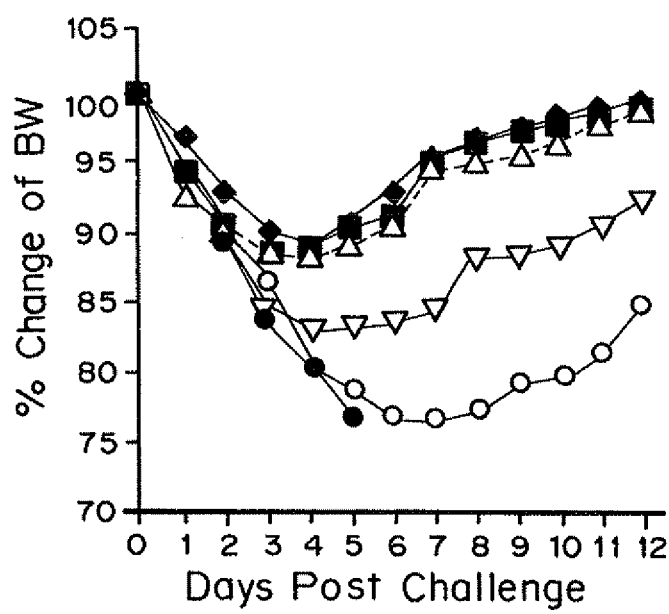

Nevertheless, mice with MVA were immunized via skin scarification. Surprisingly, MVA skin scarification induced characteristic pox lesions in a dose-dependent manner, and generated dose-dependent cellular (FIG. 11B) and humoral (FIG. 11A) immune responses against VV antigens. Importantly, when lethally challenged with intranasal WR-VV infection, MVA skin scarification provided complete protection against mortality (FIG. 11C) and illness (FIG. 11D) at $1.8 \times 10^6$ pfu, a dose at which replicative VV immunization via the conventional injection routes failed to protect mice from the lethal challenge (FIG. 3A,3B).

Figure 12A:
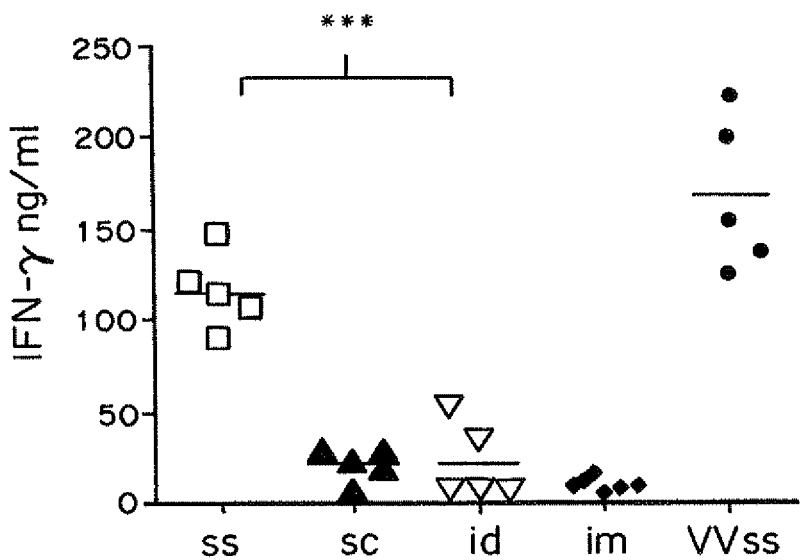
FIG. 12A-12F. Skin scarification with MVA offers superior immune response and protection efficacy compared to the injection routes. B6 mice were immunized with 2×10$^6$ pfu MVA by the indicated routes.
Figure 12B:
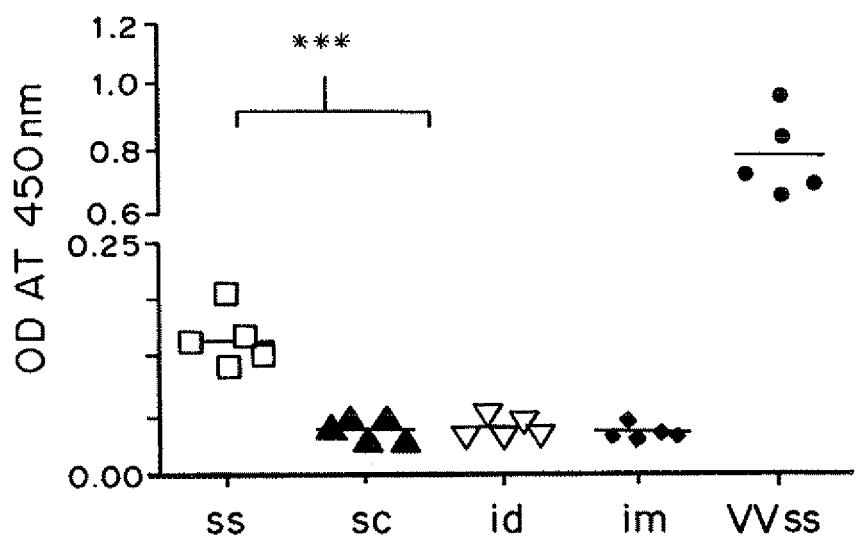
Figure 12C:
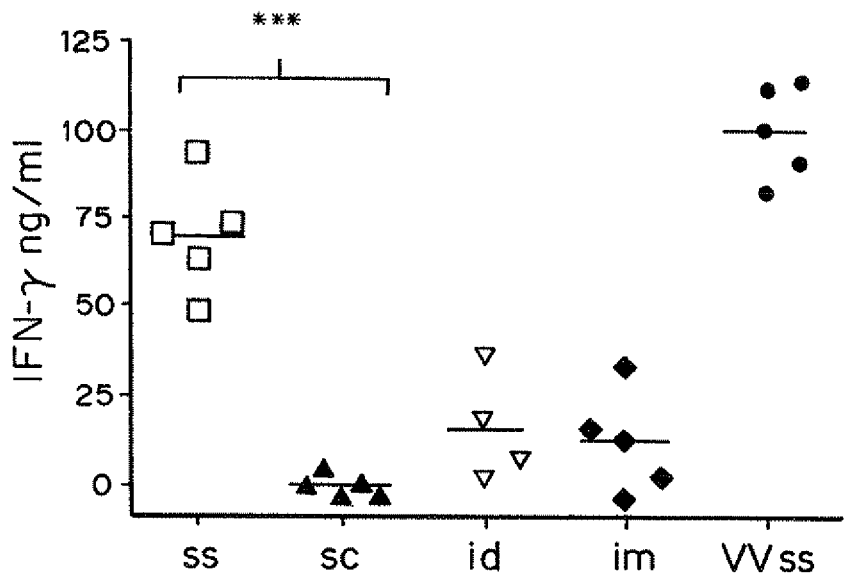
Figure 12D:
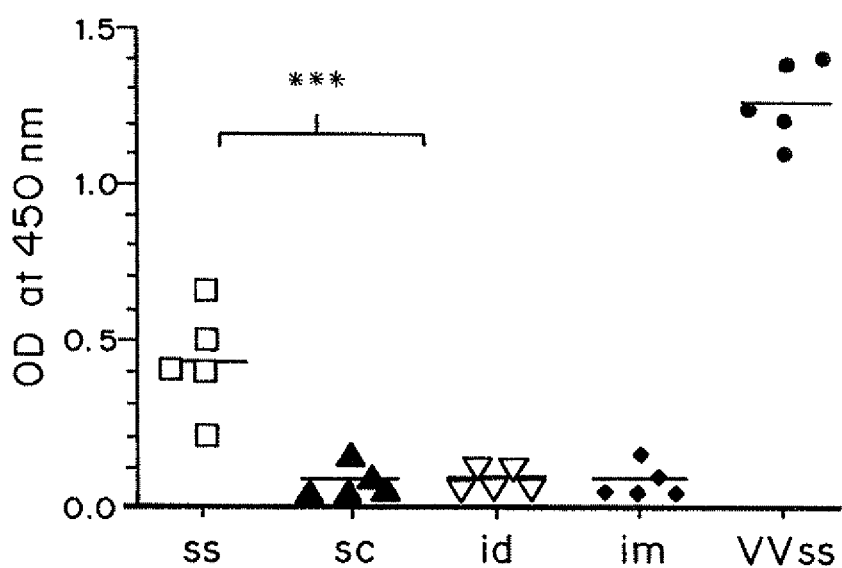
Figure 12E:
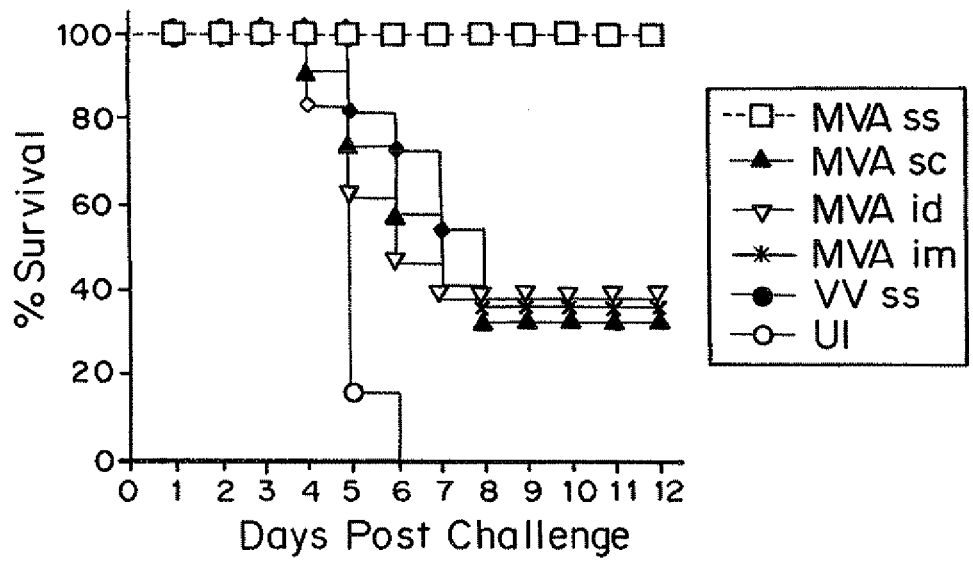
Figure 12F:
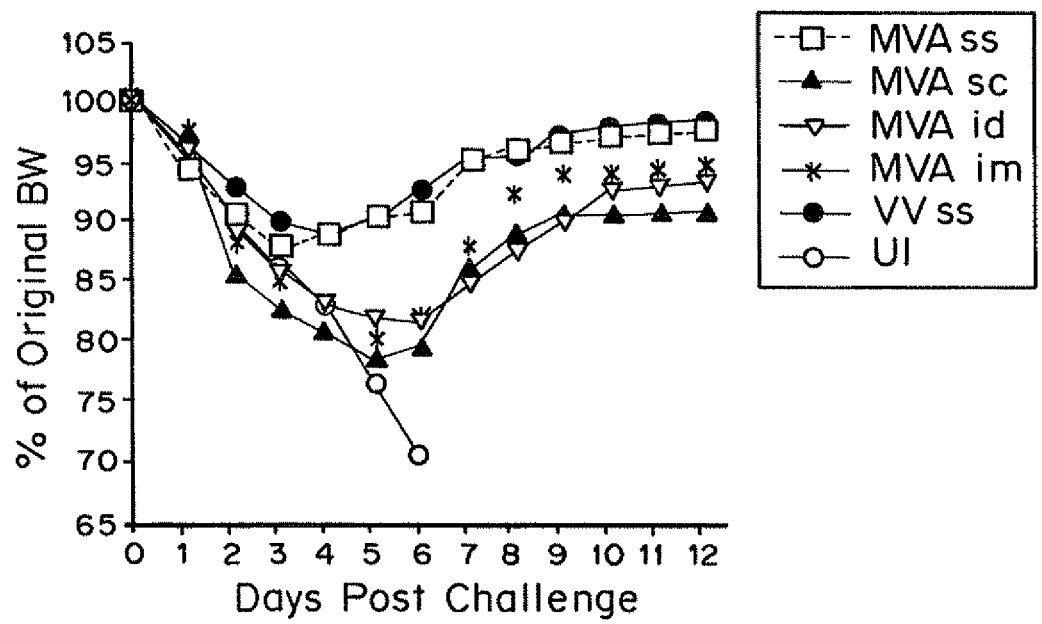

At a comparable dose ($2 \times 10^6$ pfu) of MVA immunization, the conventional injection routes only elicited weakly detectable T cell (FIG. 12A) and Ab responses (FIG. 12B), even after secondary viral challenge (FIG. 12C, 12D), and offered poor protection against the WR-VV i.n. challenge (FIG. 12E, 12Ff), whereas strong immune protection was afforded by skin scarification with either MVA or VV.

Therefore, the superior immunogenicity and protection efficacy associated with skin scarification is extended to the highly attenuated MVA vaccine.

Figure 13A:
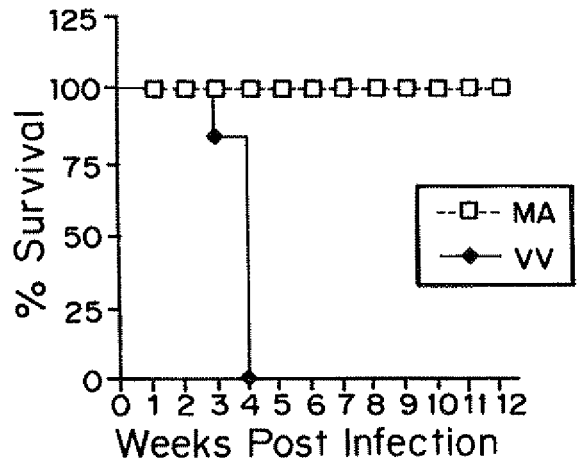
FIG. 13A-13C. MVA skin scarification is safe even for immunodeficient hosts. Rag−/− mice were immunized with 2×10$^6$ pfu MVA or VV by skin scarification. Survival (FIG. 13A) and BW change (FIG. 13B) were monitored weekly. Viral load harvested from Rag 1−/− mice at 3 months after MVA scarification was determined by real-time PCR (FIG. 13C). Naïve skin and day 7 VV-scarified wt mice skin were used as controls.
Figure 13B:
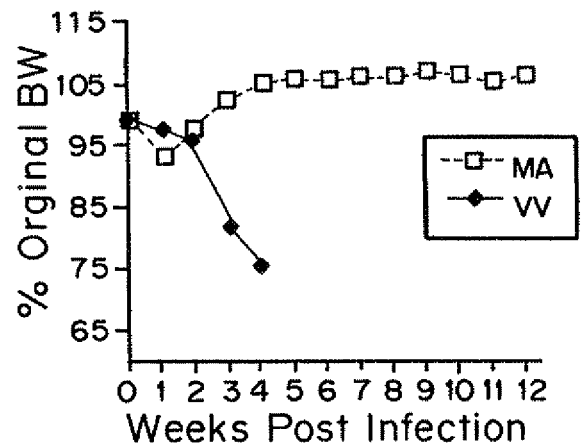
Figure 13C:
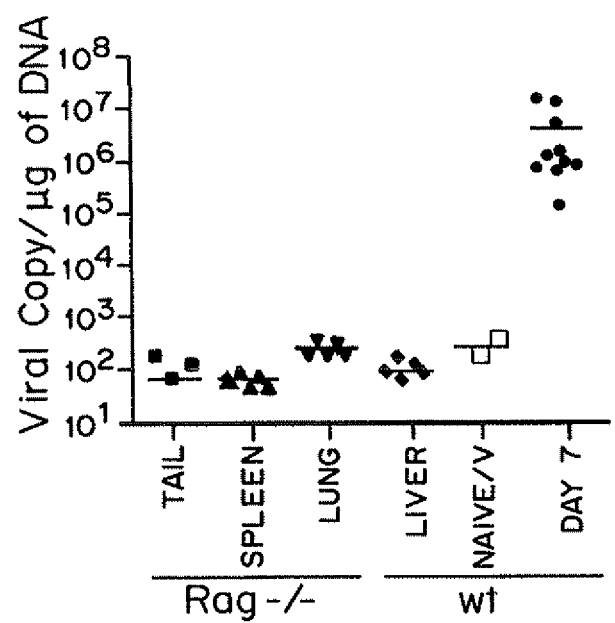

The safety of MVA skin scarification for immunocompromised hosts was confirmed in Rag-/- mice lacking both T cells and B cells. MVA scarified Rag-/- mice developed small pox lesion that was confined to the site of inoculation, and survived long-term without losing any BW (FIG. 13A, 13B) or detectable viremia (FIG. 13C). In sharp contrast, VV scarified Rag-/- mice developed deteriorating skin erosion and necrosis and succumbed around 4 weeks after infection.

The observation that MVA skin scarification is highly effective in generating protective immunity indicates productive viral infection in epidermis is not required to achieve strong protection efficacy. However, infection of epidermis with metabolically active live virus seems to be necessary for rigorous immune response to develop. This was indicated by, first, the failure of heat-inactivated VV to induce strong immune response when administered via skin scarification even at a high dose; second, the inability of simultaneous skin "scarification" with saline to enhance the immune responses in mice infected with VV by injection (data not shown). Unique aspects of innate cutaneous responses to VV infection in epidermis may serve as natural adjuvant to optimize the subsequent adaptive response. In support of this idea, it was found that primary human keratinocytes, but not dermal fibroblasts or dermal microvascular endothelial cells, are able to limit VV replication in vitro in the absence of host adaptive immune responses. Furthermore, transgenic overexpression of innate cytokine in keratinocytes led to further enhancement of in vivo adaptive immune responses following VV skin scarification.

In summary, these observations demonstrate that the route of immunization is an important consideration for the design of vaccination strategy. Epidermal immunization with live viral vaccines, including the non-replicating viruses, generates far better immune responses and stronger protection compared to the injection routes routinely used in clinic, particularly concerning MVA.

As demonstrated by the examples, after scarification of skin with VACV$_{ova}$, naïve OT-1 T cells proliferate in response to antigen, and a subset is imprinted with tissue homing molecules to migrate to infected skin as well as normal skin (at a lower level). Another subset leaves the draining LN after three or so cell divisions and migrates to all other LN, where these cells are secondarily imprinted with other tissue homing molecules. These cells in turn populate lung, liver, and gut. The result is that OT-1 $T_{EM}$ cells have been deployed to all epithelial interfaces with the environment, and these cells have effectively become $T_{RM}$. These $T_{RM}$ are most abundant near the site of scarification, next most abundant in normal skin, and then detectable (albeit less abundant) in other epithelial peripheral tissues, where they can be detected for many months after skin scarification. Most importantly, these $T_{RM}$ are not simply present—they are functional and protective, as measured by their capacity to clear infectious virus from skin. Both previously immunized skin and never immunized skin in the same mouse can rapidly mount a protective immune response to re-infection in MT antibody-deficient mice, even when mobilization of central memory T cells has been blocked by the SIP-1 inhibitor FK506.

While protection is most efficient in the previously immunized skin, never immunized skin still clears VACV with an efficiency that is orders of magnitude better than the skin of either an i.p. immunized mouse or a naïve mouse. Thus, the OT-1 cells that become $T_{RM}$ after ss-immunization in distant skin are protective at this environmental interface. Clearly, $T_{RM}$ are highly effective at mediating protective immunity. Patients with hypogammaglobulinemia, susceptible to recurrent bacterial infections, tolerate immunization with VACV normally and develop protective immunity. In contrast, those with congenital T cell defects developed severe and usually fatal complications from VACV vaccination. Moreover, immunization with inactivated VACV generated high antibody titers, but did not generate protective immunity to VACV or smallpox (Boulter, 1969). The results also indicate that scarification with heat inactivated VACV generated antibody but no IFN-gamma responses in splenic T cells, and no protection from skin challenge with VACV.

Example 6

Skin Resident Memory T Cells Accumulate Throughout Skin After Repetitive Antigenic Challenges and Provide Potent Recall Responses Human skin contains a large population of resident memory T cells ($T_{RM}$). To address their migration patterns in vivo, vaccinia virus (VACV) encoding the ovalubumin peptide $OVA_{257-264}$, was used to immunize mice previously loaded with OT-I cells via skin scarification. 30 days later, immunized mice were surgically joined with normal mice to create parabiotic mice. Parabiotic mice allow study of the recirculation of T cells in a fashion that cannot be duplicated by other experimental modalities. Parabiotic mice are surgically joined at flank skin, and their circulatory systems undergo anastomosis, followed by free exchange of circulating blood cells as early as one week after joining.

Mice loaded with OT-1 cells, then ss immunized with $VACV_{ova}$, were parabiotically joined to naïve partners 30 days after immunization. They were then separated after 2, 4, 8, 12, and 24 weeks of parabiosis. This allowed exploration of the potential recirculation of antigen specific $T_{CM}$ and $T_{RM}$.

$2 \times 10^6$ Thy1.1+ OT-I cells were intravenously transferred into Thy1.2+ recipient C57BL/6 mice 1 day prior to $2 \times 10^6$ PFU VACV-OVA skin scarification (s.s.). 30 days post infection (PI), some of OT-1-bearing mice were joined surgically with naïve normal Thy1.2+ C57BL/6 mice to create OT-I: normal parabiotic mice. The left OT-I-bearing mice were set as control (ctl). At indicated time points post surgery (PS), parabiotic mice were separated surgically to harvest lymphoid tissues and skin to examine Thy1.1+ OT-I cells.

B-cell-deficient μMT mice were used to create OT-I: normal parabiotic mice, which were separated surgically 8 weeks PS. 2 weeks after separation, they were then challenged with $2 \times 10^6$ PFU VACV-OVA on the previously infected skin, with or without daily i.p. injection of 1 mg/kg FTY720. 6 days after challenge, virus titers in the skin were examined Immunized OT-1-bearing or naïve μMT mice were used as controls. **: P<0.01. Data are representative of two independent experiments.

$2 \times 10^6$ Thy1.1+ OT-I cells were intravenously transferred into Thy1.2+ recipient C57BL/6 mice 1 day prior to infection with $2 \times 10^6$ PFU VACV-OVA by s.s. route. At indicated time points post-infection (PI), Thy1.1+ OT-I cells in both infected and uninfected skin were examined by flow cytometry. These experiments were repeated three times with similar data.

1 day after adoptive transfer of $2 \times 10^6$ Thy1.1+ OT-I cells, the receipt mice were infected with $2 \times 10^6$ PFU VACV-OVA only on the left ears. 20 and 30 days later, some of mice were challenged with $2 \times 10^6$ PFU VACV-OVA on the tail and flank skin, respectively. All infection routes are s.s. 30 days after challenge, Thy1.1+ OT-I cells were examined by analyzing their percentages (B) and absolute numbers (C) in uninfected right ears. Group 1: only Thy1.1+ OT-I cells. Group 2: Thy1.10T-I cells+left ear infection. Group 3: OT-I cells+left ear/tail/flank infections. n=5 per group. **: P<0.01. Results are representative of three independent experiments.

B-cell-deficient μMT mice were infected with $2 \times 10^6$ PFU VACV by s.s. on the left ears or i.p. injection route. 7 or 30 days later, the immunized mice were challenged with $2 \times 10^6$ PFU VACV on both ears by s.s. route. Meanwhile, 1 mg/kg FTY720 were intraperitoneally injected each day. 6 days after challenge, virus titers in both ears were examined n=5 per group. **: P<0.01. Results are representative of two independent experiments.

Mice were then separated at these time points, and then 2 weeks later were examined for the distribution of OT-1 $T_{CM}$ and $T_{RM}$. The results show that resting central memory T cells ($T_{CM}$) re-circulate freely to all secondary lymphoid tissues, while skin $T_{RM}$ remain in place long term and become a non-migratory population. These skin $T_{RM}$ were more efficient than $T_{CM}$ in eradiating recall antigen. It was believed that these $T_{RM}$ were recruited to skin over the lifetime of the individual in response to antigens encountered through skin, with the immune response in the draining lymph node engendering skin homing memory T cells. To further explore this hypothesis, OT-I-bearing mice were immunized on the left ear. The accumulation of OT-I cells was then assessed in the infected (left) and uninfected (right) ears.

OT-I cells were first detectable in the left ear at day 3, and also appeared in the uninfected ear, although they were less abundant. Peak recruitment to the infected and uninfected ear skin occurred at day 7, with roughly 10-fold more OT-I cells in infected than uninfected skin. These $T_{RM}$ persisted in both ears for many months, though their numbers diminished. It was then determined if multiple subsequent infections would lead to an increase in the number of OT-I $T_{RM}$ in never infected skin. Mice that were infected (as before) only on the left ear, were compared to another group of mice infected first on the left ear, but then 20 days later on the tail, and 30 days later on the flank. In both groups, the number of OT-I cells in the originally infected ear was compared to the uninfected ear.

Figure 14A:
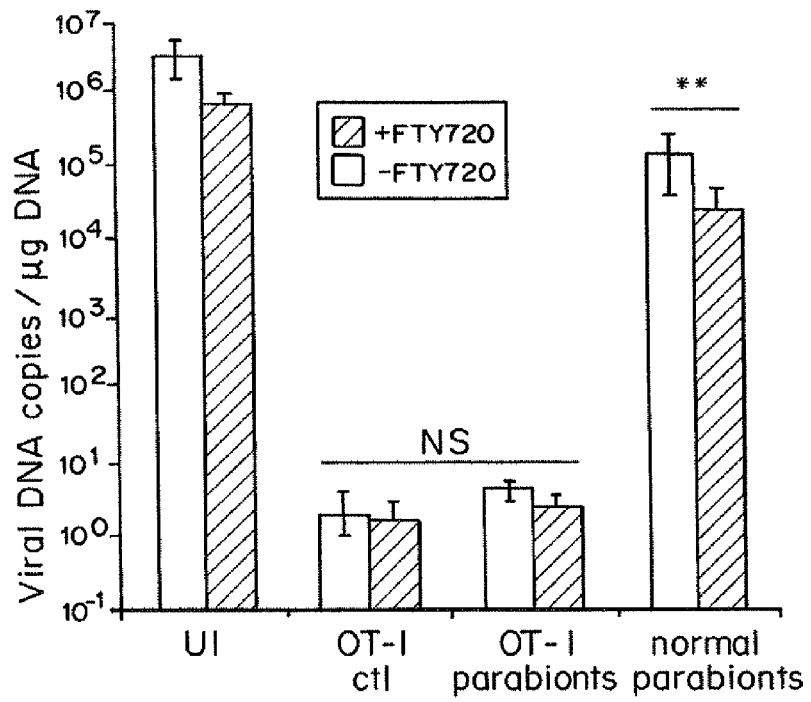
FIG. 14A is a graph of B-cell-deficient μMT mice used to create OT-I:normal parabiotic mice, which were separated surgically 8 weeks PS. 2 weeks after separation, they were then challenged with 2×10$^6$ PFU VACV-OVA on the previously infected skin, with or without daily i.p. injection of 1 mg/kg FTY720. 6 days after challenge, virus titers in the skin were examined and graphed. Immunized OT-1-bearing or naïve μMT mice were used as controls. **: P<0.01. Data are representative of two independent experiments.
Figure 14B:
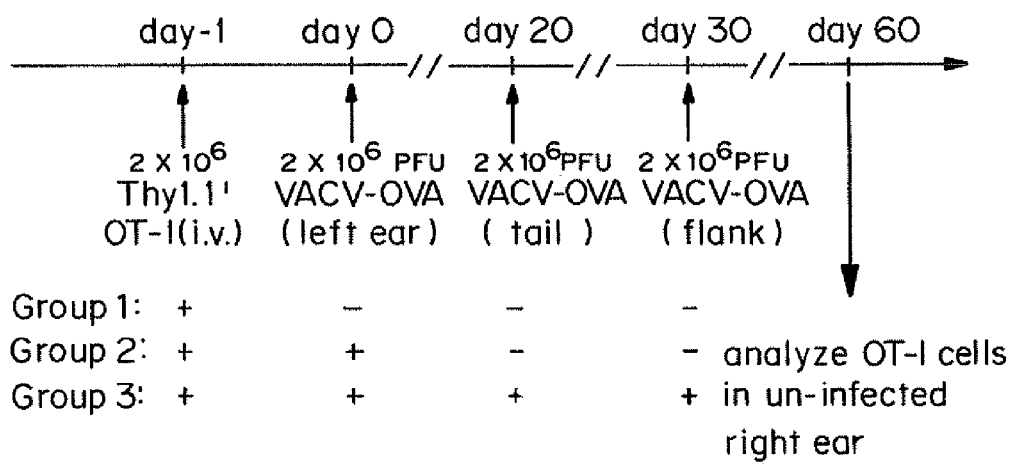
FIG. 14B is a schematic showing the methodology: 1 day after adoptive transfer of 2×10$^6$ Thy1.1+ OT-I cells, the receipt mice were infected with 2×10$^6$ PFU VACV-OVA only on the left ears. 20 and 30 days later, some of mice were challenged with 2×10$^6$ PFU VACV-OVA on the tail and flank skin, respectively.

There was a greater than three fold increase in the number of OT-I $T_{RM}$ cells in the uninfected ear of the repetitively infected mice, indicating that multiple encounters with antigen at any site increase antigen specific $T_{RM}$ throughout the skin. Finally, it was demonstrated that $T_{RM}$ in never infected skin were highly effective in clearing virus after skin infection with VACV. These experiments support the hypothesis that skin $T_{RM}$ accumulate over time, and represent an antigen experienced population of memory T cells that arises in response to antigen challenges through skin As is clear from FIG. 14A-14C, $T_{CM}$ rapidly (e.g., 2 weeks) equilibrated between the parabiotic pair in all secondary lymphoid tissues. In contrast, $T_{RM}$ remained in the skin of the scarified mouse and did not appear in the naïve parabiotic partner's skin, even after 24 weeks as a parabiotic pair. At 24 weeks, OT-1 cells are >10% of CD8+ $T_{RM}$ in immunized skin. In the unimmunized parabiotic mouse, there are no OT-1 $T_{RM}$ despite the presence of other CD8+ $T_{RM}$.

To assess the function of these $T_{RM}$ and $T_{CM}$ in parabiotic mice, rechallenge with $VACV_{ova}$ by ss. When these parabiotic mice are surgically separated (after 12 weeks) and then challenged by infection via ss, and treated daily with FTY720, the never-infected parabiont mouse cannot clear virus from skin any more efficiently than a naïve mouse (FIG. 14C), confirming the absence of functional $T_{RM}$ in the skin of the never-infected parabiont, in spite of abundant circulating $T_{CM}$. In contrast, the originally infected mouse (even if originally infected >100 days earlier) readily clears the infectious challenge from skin, even when mobilization of $T_{CM}$ is blocked by FTY-720. See FIGS. 15A and 15B. Thus, $T_{RM}$ alone, without contribution from $T_{CM}$ or circulating antibody, can provide highly effective first line protection against viral infection.

To summarize, ss immunization generates populations of T cells than can rapidly home to skin (infected skin>uninfected skin) and become skin $T_{RM}$. In addition ss immunization generates $T_{CM}$ that migrate to LN throughout the body while still activated, and at least some of these still activated $T_{CM}$ are secondarily imprinted with lung, gut, and liver homing capabilities, and migrate to these peripheral tissues taking up residence there as $T_{RM}$. After the acute infection/immunization, the remainder of the now-resting $T_{CM}$ continue to re-circulate between blood and LN, and in the absence of subsequent challenge they do not differentiate and migrate into peripheral tissues. In contrast, skin $T_{RM}$ remain in place for many months, diminishing slightly in numbers, but retaining their protective capacity against viral challenge. Not only immunized skin, but even skin remote from the site of ss immunization is protected by these $T_{RM}$, which populate the entire skin surface.

Based on these observations, that skin accumulates $T_{RM}$ as a function of being exposed to immunogenic antigens (including pathogens) through skin. At the first encounter with antigen, naïve T cells are converted to skin homing $T_{EM}$ in lymph nodes draining the site of antigen introduction/infection, and these $T_{EM}$ are most efficiently recruited to the site of infection, since their extravasation is enhanced in inflamed skin. After the $T_{EM}$ deal with the acute process, a subset remain in situ long term as $T_{RM}$. However, the results also indicate that the entire skin surface area is seeded by $T_{EM}$ which enter normal skin via low level expression of E selectin, CCR4 ligands, and ICAM-1 expressed in normal dermal microvasculature. These $T_{EM}$ remain in situ, becoming $T_{RM}$. These $T_{RM}$ can rapidly respond to a second encounter with pathogen. In addition, second encounters with pathogen will also cause differentiation of $T_{CM}$ in draining lymph node into more skin homing $T_{EM}$, which enter skin and become $T_{RM}$, amplifying this process. Thus, after a single encounter with antigen through skin, all skin is seeded with T cells, some of which become $T_{RM}$ for that antigen. After multiple encounters, the number of $T_{RM}$ for that antigen can be expected to increase significantly through accumulation over time. Most importantly, these $T_{RM}$ provide immediate front line adaptive immune protection against the offending antigen/pathogen. As skin pathogens are likely to be encountered again through the skin, this is an economical use of immunologic resources. The accumulation of $T_{RM}$ after ss immunization in other epithelial tissues occurs, but likely less efficiently when the antigen is repeatedly introduced through skin. By analogy, a first encounter of antigen through lung, or GI tract, will generate a population of $T_{EM}$ that homes to the entire lung, or segment of GI tract, most efficiently exiting vessels at sites of inflammation, but also populating normal un-inflamed lung and gut. As antigens are encountered repetitively through the same epithelial interface by the host, the number of $T_{RM}$ in that tissue would be expected to increase, provide better and more effective rapid protection against pathogens.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

We claim:

1. A method for inducing or stimulating a T cell mediated immune response to an exogenous T cell antigen in human epithelial tissues selected from the group consisting of: skin, lung, oral mucosa, gastrointestinal tract, and reproductive mucosa comprising administering to mechanically disrupted human epithelial tissue a live, modified poxvirus expressing the antigen to cause a local infection in the epithelial tissue in an amount sufficient to cause the infected cells to express viral proteins, the exogenous T cell antigen and inflammatory factors and stimulate a T cell immune response in the lymph nodes to the exogenous T cell antigen, wherein all of the virus is 100% replication deficient in normal primary human cells.

2. The method of claim 1, wherein the virus is selected from the group consisting of: orthopox, suipox, avipox, capripox, leporipox, parapoxvirus, molluscpoxvirus, and yatapoxvirus.

3. The method of claim 2, wherein the orthopox virus is a vaccinia virus.

4. The method of claim 3, wherein the non-replicating vaccinia virus is derived by natural or artificial modification of a virus selected from the group consisting of: WR strain, Wyeth strain, ACAM2000, Lister strain, LC16m8, Elstree-BNm, Copenhagen strain, and Tiantan strain.

5. The method of claim 1, wherein the epithelial tissue is epidermis which is mechanically disrupted by a scarification needle or an abrader.

6. The method of claim 1, wherein the epidermis is mechanically disrupted essentially at the same time as or before the administration of the virus.

7. The method of claim 1, wherein the subject has or is at risk of developing cancer and the antigen is a tumor-associated antigen (TAA), a tumor-specific antigen (TSA), or a tissue-specific antigen.

8. The method of claim 7, wherein the cancer is in or derived from the skin, oral mucosa, esophagus, reproductive and urogenital mucosa.

9. The method of claim 7, wherein the cancer is selected from the group consisting of melanoma, squamous cell carcinoma, basal cell carcinoma, Merkel cell carcinoma, adenexal carcinoma, cutaneous T or B cell lymphoma, sarcomas, adenocarcinoma, prostate adenocarcinoma, prostatic intraepithelial neoplasia, squamous cell lung carcinoma, lung adenocarcinoma, small cell lung carcinoma, ovarian cancer of epithelial origin, colorectal adenocarcinoma and leiomyosarcoma, stomach adenocarcinoma and leiomyosarcoma, hepatocellular carcinoma, cholangiocarcinoma, ductal adenocarcinomas of pancreas, endocrine pancreatic tumors, renal cell carcinoma, transitional cell carcinoma of kidney and bladder, and bladder squamous cell carcinoma.

10. The method of claim 1, wherein the subject has or is at risk of developing a viral, bacterial, fungal, or protozoal infection and the antigen is a viral, bacterial, fungal or protozoal antigen.

11. The method of claim 10, wherein the viral infection is selected from the group consisting of: HIV, influenza, dengue, Hepatitis A virus, Hepatitis B virus, Hepatitis C virus, human papilloma virus, Ebola, Marburg, Rabies, Hanta virus infection, West Nile virus, SARS-like Coronaviruses, Herpes simplex virus, Varicella-zoster virus, Epstein-Barr virus, Human herpesvirus 8, Alpha viruses, and St. Louis encephalitis, the bacterial infection is selected from the group consisting of: *Mycobacterium tuberculosis, Salmonella typhi, Bacillus anthracis, Yersinia perstis, Francisella tularensis, Legionella, Chlamydia, Rickettsia typhi*, and *Treponema pallidum*, the fungal infection is selected from the group consisting of: *Coccidioides immitis, Blastomyces dermatitidis, Cryptococcus neoformans, Candida albicans*, and *Aspergillus* species, and the protozoal infection is selected from the group consisting of: *Malaria Leishmania* species, *Trypanosome, cryptosporidiums, isospora* species, *Naegleria fowleri, Acanthamoeba* species, *Balamuthia mandrillaris, Toxoplasma gondii*, and *Pneumocystis carinii*.

12. The method of claim 1, further comprising administering or co-expressing a co-stimulatory molecule, a growth factor, an adjuvant and/or a cytokine, before, at the same time, or after the antigen, at the same or a distant site.

13. The method of claim 12, wherein the co-expressed co-stimulatory molecule is selected from the group consisting of: IL-1, IL-2, IL-7, IL-12, IL-15, IL-18, IL-23, IL-27, B7-2, B7-H3, CD40, CD40L, ICOS-ligand, OX-40L, 4-1BBL, GM-CSF, SCF, FGF, Flt3-ligand, CCR4.

14. A kit for immunization by mechanical disruption of an epidermal tissue consisting essentially of
 a device comprising scarification needles or an abrader, or a device comprising microneedles or microprotrusions, wherein the device is suitable for mechanically disrupting a human subject's epidermal tissue and
 a dosage unit of a live, modified, poxvirus expressing an antigen in an effective amount for inducing or stimulating a T cell mediated immune response to an exogenous T cell antigen in human epithelial tissues selected from the group consisting of: skin, lung, oral mucosa, gastrointestinal tract, and reproductive mucosa, wherein all of the virus is 100% replication deficient in normal primary human cells.

* * * * *